United States Patent [19]
Aurias et al.

[11] Patent Number: 5,968,734
[45] Date of Patent: Oct. 19, 1999

[54] NUCLEIC ACID CORRESPONDING TO A GENE OF CHROMOSOME 22 INVOLVED IN RECURRENT CHROMOSOMAL TRANSLOCATIONS ASSOCIATED WITH THE DEVELOPMENT OF CANCEROUS TUMORS, AND NUCLEIC ACIDS OF FUSION RESULTING FROM SAID TRANSLOCATIONS

[75] Inventors: Alain Aurias, Besancon; Olivier Delattre, Paris; Chantal Desmaze, Chevilly-La-Rue; Thomas Melot, Brunoy; Martine Peter, Noisy-Le-Grand; Béatrice Ploougastel; Gilles Thomas, both of Paris; Jessica Zucman, Clichy, all of France

[73] Assignee: (CNRS Centre National de la Recherche Scientifique, Paris, France

[21] Appl. No.: 08/343,443

[22] PCT Filed: May 19, 1993

[86] PCT No.: PCT/FR93/00494

§ 371 Date: Jan. 18, 1995

§ 102(e) Date: Jan. 18, 1995

[87] PCT Pub. No.: WO93/23549

PCT Pub. Date: Nov. 25, 1993

[30] Foreign Application Priority Data

May 20, 1992 [FR] France .................................. 92 06123

[51] Int. Cl.[6] ............................ C12Q 1/68; C07K 14/00; C07K 16/00; C07H 21/04
[52] U.S. Cl. ........................... 435/6; 530/402; 530/387.1; 530/350; 530/388.1; 536/23.5
[58] Field of Search ...................... 435/6, 91, 2, 7.1–7.9; 536/23.1, 24.3–24.33, 24.5; 530/388.1; 424/88; 514/44

[56] References Cited

FOREIGN PATENT DOCUMENTS

WO9113172  9/1991  WIPO.

OTHER PUBLICATIONS

Gura, Science 570: 575–577, 1995.
James, Antiviral Chemistry and Chemostherapy 2: 191–214, 1991.
Gura Science 270: 575–577, 1995.
James, Antiviral Chemistry and Chemotherapy, 2(4) 191–214, 1991.
Guterriez, The Lancet, 339: 715–721, 1992.
Talmadge, Advanced Drug Delivery Reviews, 10 : 247–299, 1993.
Goldberg et al. Clinical Chemistry 39: 2360–2374, 1993.
Freeman, Adv. Drug Delivery Reviews, 12: 169–18, 1993.
Proceedings of the American Association for Cancer Research, vol. 33, Mar. 1992, pp. 604–605—Delattre et al.
Genes & Development, Erythroleukemia induction by Friend murine leukemia virus: insertional activation of a new member of the ets gene family, Fly–1 closely, . . . etc., Ben–David et al, vol. 5, No. 6, pp. 897–1114, Jun. 1991.
Genomics, The Neuroepithelioma Breakpoint on Chromosome 22 Is Proximal to the Meningioma Locus, Zhang et al, vol. 6, No. 1, Jan. 1990.
Nature, Gene Fusion with an ETS DNA–binding domain caused by chromosome translocation in human tumours, Delattre et al, vol. 359, Sep. 10, 1992.

*Primary Examiner*—Lisa B. Arthur
*Attorney, Agent, or Firm*—Weiser and Associates, P.C.

[57] ABSTRACT

Translocations of chromosome 22 are associated with various cancers. Hybrid DNA sequences, having a portion of the Ews gene of chromosome 22 and a portion of either the Hum-Fli-1 gene of chromosome 11, the Erg gene of chromosome 21, or the Atf-1 gene of chromosome 12, are disclosed. Proteins encoded by these hybrid DNAs are disclosed. Diagnosis of specific cancers based on detection of the translocations is disclosed.

40 Claims, 27 Drawing Sheets

FIG. 1A  FIG. 1B  FIG. 1C

```
  1                                                                                gagaacgaggaggaaggagagaaa 1  M  A  S  T  D  Y  S  T  Y  S  Q  A  A  A  Q  Q  G  Y  S  A  Y  T  A  Q  P  T  Q  G  Y  A  Q  T  T  Q  A  Y  G  Q  Q  S
 25 ATGGCGTCCACGGATTACAGTACCTATAGCCAAGCTGCAGCGCAGCAGGGCTACAGTGCTTACACCGCCCAGCCCACTCAAGGATATGCACACACCACCCAGGCATATGGGCAACAAAGC 40  Y  G  T  Y  G  Q  P  T  D  V  S  Y  T  Q  A  Q  T  T  A  T  Y  G  Q  T  A  Y  A  T  S  Y  G  Q  P  P  T  G  Y  T  T  P
145 TATGGAACCTATGGACAGCCCACTGATGTCAGCTATACCCAGGCTCAGACCACTGCAACCTATGGGCAGACCGCCTATGCAACTTCTTATGGACAGCCTCCCACTGGTTATACTACTCCA 80  T  A  P  Q  A  Y  S  Q  P  V  Q  G  Y  G  T  G  A  Y  D  T  T  T  A  T  V  T  T  Q  A  S  Y  A  A  Q  S  A  Y  G  T
265 ACTGCCCCCCAGGCATACAGCCAGCCTGTCCAGGGGTATGGCACTGGTGCTTATGATACCACCACTGCTACAGTCACCACCACCCAGGCCTCCTATGCAGCTCAGTCTGCATATGGCACT 120  Q  P  A  Y  P  A  Y  G  Q  Q  P  A  A  T  A  P  T  R  P  Q  D  G  N  K  P  T  E  T  S  Q  P  Q  S  S  T  G  G  Y  N  Q
385 CAGCCTGCTTATCCAGCCTATGGGCAGCAGCCAGCAGCCACTGCACCTACAAGACCGCAGGATGGAAACAAGCCCACTGAGACTACTCAACCTCAATCTAGCACAGGGGGTTACAACCAG 160  P  S  L  G  Y  G  Q  S  N  Y  S  Y  P  Q  V  P  G  S  Y  P  M  Q  P  V  T  A  P  P  S  Y  P  P  T  S  Y  S  S  T  Q  P
505 CCCAGCCTAGGATATGGACAGAGTAACTACAGTTATCCCCAGGTACCTGGGACCTACCCCATGCAGCCAGTCACTGCACCTCCATCCTACCCTCCTACCAGCTATTCCTCTACACAGCCG 200  T  S  Y  D  Q  S  S  Y  S  Q  Q  N  T  Y  G  Q  P  S  S  Y  G  Q  Q  S  S  Y  G  Q  Q  S  S  Y  G  Q  Q  P  P  T  S  Y
625 ACTAGTTATGATCAGACCAGTTACTCTCAGCAGAACACCTATGGGCAACCGAGCAGCTATGGACAGCAGAGTAGCTATGGTCAACAAAGCAGCTATGGGCAGCAGCCTCCCACTAGTTAC 240  P  P  Q  T  G  S  Y  S  Q  A  P  S  Q  Y  S  Q  Q  S  S  S  Y  G  Q  Q  S  S  F  R  Q  D  H  P  S  S  M  G  V  Y  G  Q
745 CCACCCCAAACTGGATCCTACAGCCAAGCTCCAAGTCAATATAGCCAACAGAGCAGCAGCTACGGGCAGCAGAGTTCATTCCGACAGGACCACCCCAGTAGCATGGGTGTTTATGGGCAG 280  E  S  G  G  F  S  G  P  G  E  N  R  S  M  S  G  P  D  N  R  G  R  G  R  G  G  F  D  R  G  G  M  S  R  G  G  R  G  C  G
865 GAGTCTGGAGGATTTTCCGGACCAGGAGAGAACCGGAGCATGAGTGGCCCTCATAACCGGGGCAGGGGAAGAGGGGGATTTGATCGTGGAGGCATGAGCAGAGGTGGGCGGGGAGGAGGA 320  R  G  G  M  G  S  A  G  E  R  G  G  F  N  K  P  G  G  P  M  D  E  G  P  D  L  D  L  G  P  P  V  D  P  D  E  D  S  D  N
985 CGCGGTGGAATGGGCAGCGCTGGACAGCGAGGTGGCTTCAATAAGCCTCCTGCACCCATGGATGAAGGACCAGATCTTGATCTAGGCCCTCCTGTACATCCAGATGAAGACTCTGACAAC 360  S  A  I  Y  V  Q  G  L  N  D  S  V  T  L  D  D  L  A  D  F  F  K  Q  C  G  V  V  K  M  N  K  R  T  G  Q  P  M  I  H  I
1105 AGTGCAATTTATGTACAAGGATTAAATGACAGTGTGACTCTACATCATCTGGCAGACTTCTTTAAGCAGTGTGGGGTTGTTAAGATGAACAAGAGAACTGGGCAACCCATGATCCACATC
```

FIG. 6

400 Y L D K E T G K P K G D A T V S Y E D P P T A K A A V E W F D G K D F Q G S K L
1225 TACCTGGACAAGGAAACAGGAAAGCCCAAAGGCGATGCCACAGTGTCCTATGAAGACCCACCCACTGCCAAGGCTGCCGTGGAATGGTTTGATGGGAAAGATTTTCAAGGGAGCAAACTT

440 K V S L A R K K P P M N S M R G G L P P R E G R G M P P P L R G G P G G P G G P
1345 AAAGTCTCCCTTGCTCGGAAGAAGCCTCCAATGAACAGTATGCGGGGTGGTCTGCCACCCCGTGAGGGCAGAGGCATGCCACCACCACTCCGTGGACCTCCAGGAGGCCCAGGAGGTCCT

480 G G P M G R M G G R G G D R G G F P P R G P R G S R G N P S G G G N V Q H R A G
1465 GGGGGACCCATGGGTCGCATGGGAGGCCGTGGAGGAGATAGAGGAGGCTTCCCTCCAAGAGGACCCCGGGGTTCCCGAGGGAACCCCTCTGGAGGAGGAAACGTCCAGCACCGAGCTGGA

520 D W Q C P N P G C G N Q N F A V R T E C N Q C K A P K P E G F L P P P F P P P G
1585 GACTGGCAGTGTCCCAATCCGGGTTGTGGAAACCAGAACTTCGCCTGGAGAACAGAGTGCAACCAGTGTAAGGCCCCAAAGCCTGAAGGCTTCCTCCCGCCACCCTTTCCGCCCCCGGGT

560 G D R G R G G P V G M R G G R G G L M D R G G P G G M F R G G R G G D R G G F R
1705 GGTGATCGTGGCAGAGGTGGCCCTGGTGGCATGCCCCCAGGAAGAGGTGGCCTCATGGATCGTGGTGGTCCCGGTGGAATGTTCAGAGGTGGCCGTGGTGGAGACAGAGGTGGCTTCCGT

600 G G R G M D R G G F G G G R R G G P G G P P G P L M E Q M G G R R G G R G G P G
1825 GGTGGCCGGGGCATGGACCGAGGTGGCTTTGGTGGAGGAAGACGAGGTGGCCCTGGGGGCCCCCTGGACCTTTGATGGAACAGATGGGAGGAAGAAGAGGAGGACGTGGAGGACCTGGA

640 K M D K G E H R Q E R R D R P Y •
1945 AAAATGGATAAAGGCGAGCACCGTCAGGAGCGCAGAGATCGGCCCTACTAGatgcagagacccgcagagctgcattgactaccagatttattttttaaaccagaaaatgttttaaattt 2065 ataattccatatttataatgttggccacaacattatgattattccttgtctgtactttagtattttcaccatttgtgaagaaacattaaaacaagttaaatggtagtgtgcggagtttt 2185 tttttcttccttcttttaaaaatggttgtttaagactttaacaatgggaaccccttgtgagcatgctcagtatcattgtggagaaccaagagggcctcttaactgtaacaatgttcatgg 2305 ttgtgatgtttttttttttttttaaaataaaattccaaatgtttaataaaaaaaaaaaaaaaaaaa 2372

FIG. 6A

```
                                                                    -143  ggagggcgctcgcagggggcac -121
gcagggagggcccagggcgccagggaggccgcgccgggctaatccgaaggggctgcgaggtcaggctgtaaccgggtcaatgtgtggaatattgggggggctcggctgcagacttggccaa  -1

M  D  G  T  I  K  E  A  L  S  V  V  S  D  D  S  L  F  D  S  A  Y  G  A  A  A  H  L  P  K  A  D  M  T  A  S  G  S  P      40
      ATGGACGGGACTATTAAGGAGGCTCTGTCGGTGGTGAGCGACGACCAGTCCCTCTTTGACTCAGCGTACGGAGCGGCAGCCCATCTCCCCAAGGCCGACATGACTGCCTCGGGGAGTCCT  120

D  Y  G  Q  P  H  K  I  N  P  L  P  P  D  D  E  V  I  N  Q  P  V  R  V  N  V  K  R  E  Y  D  H  M  N  G  S  R  E  S  P
      GACTACGGGCAGCCCCACAAGATCAACCCCCTCCCACCACAGCAGGAGTGGATCAATCAGCCAGTGAGGGTCAACGTCAAGCGGGAGTATGACCACATGAATGGATCCAGGGAGTCTCCG  240

V  D  C  S  V  S  K  C  S  K  L  V  G  G  G  E  S  N  P  M  N  Y  N  S  Y  M  D  E  K  N  G  P  P  P  P  N  M  T  T  N    120
      GTGGACTGCAGCGTTAGCAAATGCAGCAAGCTGGTGGGCGGAGGCGAGTCCAACCCCATGAACTACAACAGCTATATGGACGAGAAGAATGGCCCCCCTCCTCCCAACATGACCACCAAC  360

E  R  R  V  I  V  P  A  D  P  T  L  V  T  D  E  H  V  R  D  V  L  E  V  A  I  K  E  Y  S  L  M  E  I  D  T  S  F  F  D    160
      GAGAGGAGAGTCATCGTCCCCGCAGACCCCACACTGTGGACACAGGAGCATGTGAGGCAATGGCTGGAGTGGGCCATAAAGGAGTATAGCTTGATGGAGATCGACACATCCTTTTTCCAG  480

N  M  D  G  K  E  L  C  K  M  N  K  E  D  F  L  R  A  T  T  L  Y  N  T  E  V  L  L  S  H  L  S  Y  L  R  E  S  S  L  L    200
      AACATGGATGGCAAGGAACTGTGTAAAATGAACAAGGAGGACTTCCTCCGCGCCACCACCCTCTACAACACGGAAGTGCTGTTGTCACACCTCAGTTACCTCAGGGAAAGTTCACTGCTG  600

A  Y  N  T  T  S  H  T  D  D  S  S  R  L  S  V  K  E  D  P  S  Y  D  S  V  R  R  G  A  V  G  N  N  M  N  S  G  L  N  K    240
      GCCTATAATACAACCTCCCACACCGACCAATCCTCACGATTGAGTGTCAAAGAAGACCCTTCTTATGACTCAGTCAGAAGAGGAGCATGGGCAATAACATGAATTCTGGCCTCAACAAA  720

S  P  P  L  G  G  A  D  T  I  S  K  N  T  E  D  R  P  D  P  D  P  Y  D  I  L  G  P  T  S  S  R  L  A  N  P  G  S  G  D    280
      AGTCCTCCCCTTGGAGGGGCACAAACGATCAGTAAGAATACAGAGCAACGGCCCCAGCCAGATCCGTATCAGATCCTGGGCCCGACCAGCAGTCGCCTAGCCAACCCTGGAAGCGGGCAG  840

I  D  L  V  D  F  L  L  E  L  L  S  D  S  A  N  A  S  C  I  T  V  E  G  T  N  G  E  F  K  M  T  D  P  D  E  V  A  R  R    320
      ATCCAGCTGTGGCAATTCCTCCTGGAGCTGCTCTCCGACAGCGCCAACGCCAGCTGTATCACCTGGGAGGGGACCAACGGGGAGTTCAAAATGACGGACCCCGATGAGGTGGCCAGGCGC  960
```

FIG. 7

```
    W G E R K S K P N M N Y D K L S R A L R Y Y Y D K N I M T K V H G K R Y A Y K F   360
TGGGGCGAGCGGAAAAGCAAGCCCAACATGAATTACGACAAGCTGAGCCGGGCCCTCCGTTATTACTATGATAAAAACATTATGACCAAAGTGCACGGCAAAAGATATGCTTACAAATTT  1080

D F H G I A D A L D P H P T E S S M Y K Y P S D I S Y M P S Y H A H D D K V N F   400
GACTTCCACGGCATTGCCCAGGCTCTGCAGCCACATCCGACCGAGTCGTCCATGTACAAGTACCCTTCTGACATCTCCTACATGCCTTCCTACCATGCCCACCAGCAGAAGGTGAACTTT  1200

V P P H P S S M P V T S S S F F G A A S D Y W T S P T G G I Y P N P N V P R H P   440
GTCCCTCCCCATCCATCCTCCATGCCTGTCACTTCCTCCAGCTTCTTTGGAGCCGCATCACAATACTGGACCTCCCCCACGGGGGGAATCTACCCCAACCCCAACGTCCCCGCCATCCT  1320

N T H V P S H L G S Y Y *  452
AACACCCACGTGCCTTCACACTTAGGCAGCTACTACTAGaagcttactcatcagtggccttctagctgaagcccatcctgcacacttactggatgctttggactcaacaggacatatgtg  1440 gccttgaagggaagacaaaactggatgttctttcttgttggatagaaccttgtatttgttcttaaaaacattttttttaatgttggtaacttttgcttcctctacctgaacaaagaga  1560 tgaataattccatgggccagtatgccagtttgaattctcagtctcctagcatcttgtgagttgcatattaagattactggaatggttaagtcatggttctgagaaagaagctgtacgttt  1680 tctttatgttttatgaccaaagcagtttcttgtcaatacacggggttcagtatgacacagaatcatggacttaacccgtcatgttctggtttgagatttagtgacaaatagaggtggga  1800 agcttataatctaattttaggaggaccaaattcagtggatggcaactggaacattgattgtaaggccagtgaagttttcacccaactggaatttgatggaaagaaggtttgtgtgtttaa  1920 gacgccaagggcattgcagaatccctctcagtggacagtatgcactcagctgaccactctctctagaaatagtcaagatatgaactaagaaattttaatgcaaatacatacattcctgaa  2040 agacggggaattaaattactaatttttttttttttttaaatgatgacagtggtcccagaacttggaaaagttgtagggatttctaaactcaagcagattcgcaagtgctgtgcgcttgtc  2160 agaccatcagaccagggccaaccaatcagaaggcaacttactgtataaattatgcagagttattttcctatatctcacagtattaaaaataaataattaaaaattaagaatgaaataaacg  2280 agttgacctcggtcacaaaagcagttttactatcgaatcaatcgctgttattttttttaatgtaatttgtacatctttttttcaatctgtacatttgggctgtctgtatgttttatagct  2400 ggttttttaaaaagcataatatgcctatagctgaaaaggaaacagggctgtttaagtcactgacttatgagaaagcaaagcactggtacagttatttaacaggcatacacaagcagggaaa  2520 gataatccatttagatctttaatgctttggaaatgcgtgtaacagtactgcaataatcacagctctggggaaaaacaacgaaactttcccttgtggagaggagggatttcctgctctata  2640 taagcaacatattttagacattaaaatatatataattttgcaggtaattgttgacttttttaactatattaagcgttaagctgacaactgtcaaagaagaccatgttgtaaaataatttt  2760 gactaaataaatggttccttctctcaaaaaaaaaaa  2796
```

FIG. 7A

```
         Exs                                              Hum-Fli-1
 S Y S Q  A P S Q Y S Q Q S S S Y G Q Q   N P S Y D S V R R G A W G N N M N S G L N
TCCTACAGCCAAGCTCCAAGTCAATATAGCCAACAGAGAGCAGCTACGGGCAGCAGAACCCTTCTTATGACTCAGTCAGTCAGAAGAGGAGCTTGGGCAATAACATGAATTCTGGCCTCAAC
 K S P P L G G A Q T I S K N T E Q R P Q D P Y Q I L G P T S S R L A N P G S G
AAAAGTCCTCCCCTTGGAGGGGCACAAACGATCAGTAAGAATACAGAGCAACGGCCCCAGCCAGATCCGTATCCGGCCCGACCAGCAGTGCCTAGCCAACCCTGGAAGCGGG
 Q I Q L W Q F L L E L L S D S A N A S C I T W E G T N G E
CAGATCCAGCTGTGGCAATTCCTCCTGGAGCTGCTCTCCGACAGCGCCAACGCGCCAAGCTGTATCACCTGGGAGGGGACCAACGGGGAGT
```

FIG. 8

```
                                        EXON 1
                                      MetAlaSerThrA
                        GAGAACGAGGAGGAAGGAGAGAAA ATGGCGTCCACGG gtgagtatggtggaactgcggtcgcgccgg
                                       EXON 2 (37bp)
                                   spTyrSerThr..... AlaGlnGlnGl
acactattttttcctccttgttttcctctag    ATTACAGTACC..... GCGCAGCAGGG gtaagtcagtcttttataaccgtattttgt
                                       EXON 3 (52bp)
                                   yTyrSerAla....... ThrThrGln
ttcaagttattgcatttaattcttttgcag     CTACAGTGCT....... ACCACCCAG gtaatctttaaaataattacatgtagctgc
                                       EXON 4 (124bp)
                                   AlaTyrGly....... ProProThrG
gttcttgcattcggtttttttttggagcag     GCATATGGG....... CCTCCCACTG gtaaggcctgccttggagagattttgggt
                                       EXON 5 (187bp)
                                   lyTyrThrThr..... AlaProThrAr
gaaatctgatgcagctcccctttggtctag     GTTATACTACT..... GCACCTACAAG gtaaggccatggtgtccttaatgcgtcagt
                                       EXON 6 (168bp)
                                   gProGlnAsp...... ProProThrSe
tttaattttatttattatttctcctcttag     ACCGCAGGAT...... CCTCCTACCAG gtcagtctactttttgtggcaaaacaaaaa
                                       EXON 7 (212bp)
                                   rTyrSerSer....... GlyGlnGlnS
tttttttttttctccttcctctctctttcag    CTATTCCTCT....... GGGCAGCAGA gtgagttgctaagagagaaaaccaaataag
                                       EXON 8 (181bp)
                                   erSerPheArg........ GlyMetGl
catggcttacagatgtgactctttcctcag     GTTCATTCCGA........ GGAATGGG gtaagagcaaaccttttctccttttaccta
                                       EXON 9 (38bp)
                                   ySerAlaGly....... LysProGlyG
aaggccttcatttctcgtttatccccccag     CAGCGCTGGA....... AAGCCTGGTG gtaagttttgagtattaccatagatagtg
                                       EXON 10 (33bp)
                                   lyProMetAsp...... LeuAspLeuG
atattttatatgatctttcctggttggcag     GACCCATGGAT...... CTTGATCTAG gtaagttgaattcctagttgtgccttccat
                                       EXON 11 (119bp)
                                   lyProProVal.... GlyValValLys
ataattctcctgtcttgttgtctctgaaag     GCCCACCTGTA.... GGGGTTGTTAAG gtcagtaaaagcataaccaggtcatctggc
                                       EXON 12 (130bp)
                                   MetAsnLysArg.. GluTrpPheAspG
tcatgcctaactatgctattctttgtctag     ATGAACAAGAGA.. GAATGGTTTGATG gtgagatgtactcactggcattcttaatct
                                       EXON 13 (123bp)
                                   lyLysAspPhe... ProLeuArgGlyG
agtaattgatgttctgttgtcttgttccag     GGAAAGATTTT... CCACTCCGTGGAG gtactttactgagctcctatgttgcatta
```

| FIG. 12A |
|----------|
| FIG. 12B |

```
                                    EXON 14 (163bp)
                              lyProGlyGlyPro.....ProAsnPr
atttgctgtttcttgttgttcttgttgtag  GTCCAGGAGGCCCA.....CCCAATCC gtatgtacttgtctgggaaaattgataccc
                                    EXON 15 (98bp)
                              oGlyCysGlyAsn.......ProProG
tgatttctgctgtgatgtaattgtatgcag  GGGTTGTGGAAAC.......CCCCCGG gtaggtgcaggtttcatgagtgtcccctca
                                    EXON 16 (253BP)
                              lyGlyAspArg........MetAspLy
actgctttcgccctgctattctcaccttag  GTGGTGATCGT........ATGGATAA gtaagtgctggtgaaaagcagctgtgggcc
                                    EXON 17 (365bp)
                              sGlyGluHisArgGlnGluArgArgAspArgProTyr***
tctaaccgaagggccctctttaccttgcag  AGGCGAGCACCGTCAGGAGCGCAGAGATCGGCCCTACTAGATGCAGAGACCCCGCAGA
GCTGCATTGACTACCAGATTTATTTTTTAAAACCAGAAAATGTTTTAAATTTATAATTCCATATTTATAATGTTGGCCACAACATTATGAT
TATTCCTTGTCTGTACTTTAGTATTTTTCACCATTTGTGAAGAAACATTAAAACAAGTTAAATGGTAGTGTGCGGAGTTTTTTTTTCTTC
CTTCTTTTAAAAATGGTTGTTTAAGACTTTAACAATGGGAACCCCTTGTGAGCATGCTCAGTATCATTGTGGAGAACCAAGAGGGCCTCT
TAACTGTAACAATGTTCATGGTTGTGATGTTTTTTTTTTTTTTTAAATAAAATTCCAAATGTTTAT
```

FIG. 12B

```
                                    EXON 1
                                    MetAspGlyThrIleLys
            ctcggctgcagacttggccaa   ATGGACGGGACTATTAAG   gtaagcggcggggcaacggacgcgggcggc EXON 2
                                    GluAlaLeuSer......AsnGlySer..
   acccggggatcctctagagtcgacctgcag   GAGGCTCTGTCG.....GAATGGATCCAG   gtaagctcaccaggcctgtgcaggattggg EXON 3
                                    .GluSerPro........ValProAla.
   ccttgggcttttgccccctcctcactttag   GGAGTCTCCGGT.....TCGTCCCCGCAG   gtaagtcgagaaccaggctgcctgggcgcc EXON 4
                                    ..ProThrLeu........LeuArgGlu.
   tccttgctaacaacgtcttctcctctgcag   ACCCCACACTGT.....ACCTCAGGGAAA   gtaagtgccgcccaagtacccagggctggg EXON 5
                                    ..SerLeuLeu........ValLysGlu.
   gttataacctgtttatgttttgcctctcag   GTTCACTGCTGG.....GTGTCAAAGAAG   gtaagtttgttcttttgtgcacttaaaatt EXON 6
                                    ..ProSerTyr........LeuAsnLys.
   aatgtaccccctatttgttattgttcattag  ACCCTTCTTATG.....GCCTCAACAAAA   gtaagtaaatgttttatagttctttggagg EXON 7
                                    ..ProProLeu........ProGlnPro.
   ctcactgcatttctttccctcttgccacag   GTCCTCCCCTTG.....GGCCCCAGCCAG   gtacctgcccaggatatgtaatctctcctt EXON 8
                                    ..ProTyrGln........AlaAsnPro.
   tgaagcaaatttcctttttttatttccttag  ATCCGTATCAGA.....TAGCCAACCCTG   gtgagtttaccttggcctgcaagccttttt EXON 9
                                    ..SerGlyGln......SerTyrTyr***
   tgttctctcccgtttcctcacggcgtgcag   GAAGCGGGCAGA.....AGCTACTACTAG   aagcttactcatcagtggccttctagctga
```

FIG. 13

```
CTGCAGAGCGCGCCCAGGCAACCCCGAAAGGCCGGTCGGGGACCCCGGCTGGGAGTCAGG -533

ACTCTAGCTCCCGGGCGCGACCCGAGAACCCTGAATCCATTCCGCGCACACCCGGCACGC -473

GTGACCCCTGCCGACCGGCTGGCGCGCCACCCATTCCCCGCGGCCCGCGGATTAGTCAGC -413

AGTTGTTCTAGTCCGGGTCCCTTCCCCCAGCCCTCCCGCCGATCTCCGTCTCCCTGCAGG -353

GCCGACTCTTCAGCGACCGTCCCTAGAGCCAGCGGACGGAACCATTCCAAACAGCCTAGT -293

CTCGTGCTGAGAGCCTCTCCGGTTTCACGCTGAGACCCGCTCACCCCCGCTCTGGCCCCT -233

TAGATGCTATTTTGGCCCGAGTGTCACGTCGGGCGCTCTTTAGAGAGGACTGGGACAAGA -173

GTTGCGGACGCGAAGAACGAGTAAGCGGTGGTTCATCCCTCCTGACCCCACCCCCGTGGC -113

CTGGCCCGATGGTCGCGCCCGGGGTTGCGAGATTTGCGCCTGCGCAGTGCGGCGCCTAGA  -53

GGGAAAGCGAGAGGGAGACGGACGTTGAGAGAACGAGGAGGAAGGAGAGAAAATGGCGTC    8
                                                  MetAlaSe
CACGGgtgagtatggtggaactgcggtcgcgccggcggtagccggaacgcccaaactggg   68
RThrA
ggtcgttcgtctctgggcttggctgggaagactgagtggagttgccgagaggggggttgag 128 gcacccgccgcggcccgacgagctcggggatccgcattcctctcccctcccccaaccggg  188 cgggccggttctggaatcttcccgcgccctcgcgcgcgggggctttgctttt           241
```

```
                                    EX 8                              EX 9                         EX 10
                         G  R  G  G  M  G         S  A  G    K  P  G    G  P  M  D
EWS                  ...GGACGCGGGTGGAATGGG|CAGCCGCTGGA...AAGCCTGGT|GGACCCATGGAT...
CHR 22

G  R  G  G  M  G         K  I  L  K
EWS/ATF-1            ...GGACGCGGGTGGAATGGG|AAAAATTTGAAA...
der (22)

R  R  P  S  Y  R         K  I  L  K
ATF-1                ...CGGCGCCCCATCTTACAG|AAAAATTTGAAA...
CHR 22

R  R  P  S  Y  R    T  H  G  *
ATF-1/EWS            ...CGGCGCCCCATCTTACAG|GACCCATGGATGA...
der (12)
```

FIG. 23

NUCLEIC ACID CORRESPONDING TO A GENE OF CHROMOSOME 22 INVOLVED IN RECURRENT CHROMOSOMAL TRANSLOCATIONS ASSOCIATED WITH THE DEVELOPMENT OF CANCEROUS TUMORS, AND NUCLEIC ACIDS OF FUSION RESULTING FROM SAID TRANSLOCATIONS

This application was filed under 35 U.S.C. 371 PCT/FR93/00494, filed May 19, 1993.

The present invention relates to a nucleic acid including all or part of the nucleic sequence of a gene of chromosome 22 involved in the recurrent chromosomal translocations associated with the development of cancerous tumors. The subject of the invention is also hybrid nucleic acids corresponding to the products of fusion resulting from the chromosomal translocations in which this gene of chromosome 22 is involved.

The invention relates more particularly to a nucleic acid including all or part of the nucleic sequence of the gene of chromosome 22 involved in the recurrent chromosomal translocations t(11;22), t(21;22) and t(12;22), as well as the hybrid nucleic acids resulting from the fusion of this gene of chromosome 22 with the genes of chromosomes 11, 21 and 12, respectively, which are involved in these translocations. The invention also relates to the mRNAs originating in the DNA of the gene of chromosome 22 and the fusions DNAs as well as the cDNAs that can derive from them, as well as the proteins for which they code.

The invention also relates to the detection of the gene of chromosome 22 involved in the chromosomal translocations, as well as the fusion genes resulting from these translocations, with the aid of probes prepared on the basis of precursor nucleic acids, with a view to diagnosing Ewing's sarcoma and related tumors in subjects suffering from "small round cell", or small cell, tumors or primitive peripheral neurectodermic tumors, or malignant melanoma of the soft tissues; the invention also relates to the detection, for the same purposes, of products for which these genes code, and the products and reagents for implementing these methods.

Recurrent chromosomal translocations represent a mechanism of oncogene activation and hence are implicated in the appearance of numerous pathogenic tumors (E. Solomon, J. Barrow, A. D. Goddard, Science 254, 1153–1160 (1991)). Among them, those known as small cell tumors represent a group of heterogeneous cancers. Precise diagnosis of these tumors is essential so that the therapeutic protocol to be used to treat them can be chosen correctly. A subset of these tumors involves a chromosomal translocation t(11;22)(q24;12) and is sensitive to the same therapeutic protocol.

Ewing's sarcoma represents the most frequent secondary bone tumor in the child. Despite the lack of a morphological marker, Ewing's sarcoma cells occasionally express antigens or can cause the expression of characteristic morphological traits of neural differentiation (M. Lipinski, K. Braham, I. Philip et al., Cancer Res. 47, 183–187 (1987); A. O. Cavazzana, J. S. Miser, J. Jefferson, T. J. Triche, Am. J. Pathol. 127, 507–518 (1987)). Thus techniques for diagnosing small cell tumors use the conventional methods of anatomopathology and cytology, and hence represent a diagnosis by exclusion, which is not entirely reliable. Demonstrating the presence of a chromosomal translocation t(11;22) in a small cell tumor can be done by a karyotype study; this study requires the cells to arrive at the laboratory alive, which is often difficult to achieve and results in an elevated failure rate; furthermore, there are difficulties in interpretation.

Ewing's sarcoma (ES) has been connected with a subtype of peripheral primitive neurectodermic tumors (PNET) called peripheral neuroepithelioma (PN). This relationship is also supported by the highly specific expression of the MIC2 antigen both in Ewing's sarcoma (ES) and in peripheral neuroepithelioma (PN), while in the majority of other human tumors this antigen is not expressed (I. M. Ambros, P. F. Ambros, S. Strehl et al., Cancer 67, 1886–1893 (1991); P. Garin-Chesa, E. J. Fellinger, A. G. Huvos et al., Am. J. Pathol. 139, 275–286 (1991)). With other rare subtypes of primitive neurectodermic tumors (J. Whang-Peng, C. E. Freter, T. Knutson, J. J. Nanfro, A. Gazdar, Cancer Genet. Cytogenet. 29, 155–258 (1987); J. P. Chadarevian, M. Vekemans, T. A. Seemayer, N. Engl. J. Med. 311, 1702–1703 (1984); A. O. Cavazzana, S. Navarro, R. Noguera et al., Adv. Neuroblastoma Res. 2, 463–473 (1988); N. V. Vigfusson, L. J. Allen, J. H. Philip, T. Alschibaja, W. G. Riches, Cancer Genet. Cytogenet. 22, 211–218 (186)), Ewing's sarcoma and peripheral neuroepithelioma share a highly specific and cytogenetically identical chromosomal translocation t(11;22)(q24;q12) (A. Aurias, C. Rimbaut, C. Buffe, J. Dubousset, A. Mazabraud, N. Engl. J. Med. 309, 496–497 (1983); C. Turc-Carel, I. Philip, M. P. Berger, T. Philip, G. M. Lenoir, N. Engl. J. Med. 309, 497–498 (1983); J. Whang-Peng, T. J. Triche, T. Knutsen, J. Miser, E. C. Douglass, M. A. Israel, N. Engl. J. Med. 311, 584–585 (1984)). This translocation has been observed in 83% of cases of Ewing's sarcoma. More complex variants of this translocation or translocations have been observed in 9% of other cases and consistently involve the 22q12 band (C. TurcCarel, A. Aurias, F. Mugneret et al., Cancer Genet. Cytogenet. 32, 229–238 (1988)). The region 22q12 thus appears to be one of the main sites where recurrent chromosomal alterations encountered in a defined group of human tumors appear.

The research work done on the physical mapping of the long arm of chromosome 22 (F. Zhang, O. Delattre, G. Rouleau, J. Couturier, D. Lefrancois, G. Thomas, A. Aurias, Genomics 6, 174–177 (1990); F. R. Zhang, A. Aurias, O. Delattre, M. H. Stern, J. Benitez, G. Rouleau, G. Thomas, Genomics 7, 319–324 (1990); O. Delattre, C. J. Azambuja, A. Aurias, J. Zucman, M. Peter, F. Zhang, M. C. Hors-Cayla, G. Rouleau, G. Thomas, Genomics 9, 721–727 (1991)), and isolation of probes in proximity with the chromosomal breakpoint (J. Zucman, O. Delattre, C. Desmaze, C. Azambuja, G. Rouleau, P. De Jong, A. Aurias, G. Thomas, Genomics, in press) have led the present inventors to determine that the translocation t(11;22)(q24;q12) fuses a gene carried on chromosome 22 and a gene carried on chromosome 11; this fusion leads to the formation of a hybrid gene associated with the pathology. These two genes have been characterized, and it has been possible to define the products of their fusion.

The gene of chromosome 22 involved in the translocation t(11;22), called Ews, has been isolated and its cDNA has been sequenced; the sequence of the protein for which it codes was deduced from the cDNA sequence; the Ews gene includes a region called EWSR1 of approximately 7 Kb at the level of which the breakpoint of chromosome 22 is located.

The gene of chromosome 11 involved in the translocation t(11;22), called Hum-Fli-1, has been isolated and its cDNA has been sequenced; the sequence of the protein for which it codes was deduced from the cDNA sequence; the Hum- Fli-1 gene includes a region called EWSR2 of approximately 40 Kb at the level of which the breakpoint of chromosome 11 is located. Furthermore, the inventors have confirmed the strong homology of the Hum-Fli-1 gene with the genes of the Ets family and more particularly with the murine Fli-1 gene (V. Baud et al., Genomics, Vo. 11, 223–224, 1991; Y. Ben-David et al., Genes & Development, Vol. 5, No. 6, 1991).

The inventors have also demonstrated that in approximately 12% of cases of Ewing's sarcoma, the Ews gene of chromosome 22 fuses with the Erg carried on chromosome 21. This Erg gene is also a member of the family of transcription factors Ets.

Furthermore, the research work done by the inventors on recurrent chromosomal translocations in which the Ews gene is involved has lead them to determine that the recurrent chromosomal translocation t(12;22)(q13;12) associated with soft tissue malignant melanoma (STMM) fuses the Ews gene with the Atf-1 gene carried in chromosome 12. The link between the translocation t(12;22) and soft tissue malignant melanoma has been described, (particularly by J. A. Bridge et al. (J. A. Bridge, D. A. Borek, J. R. Neff, M. Huntrakoon, Am. J. Clin. Pathol. 93, 26–31, 1986) and G. Stenman et al. (G. Stenman, L.-G. Kindblom, L. Angervall, Genes Chrom. Cancer 4, 122–127, 1992).

Soft tissue malignant melanoma is a grave tumor that most often develops in the tendons and aponeuroses in subjects aged 15–35 (E. B. Chung, F. M. Enzinger, Am. J. Surg. Pathol. 7, 405–413, 1983; L. Epstein, A. O. Martin, R. Kempson, Cancer Res. 44, 1265–1274, 1984). Although STMM shares several common phenotype figures with cutaneous malignant melanomas, the translocation t(12;22) (q13;12) is specific to this type of tumor (F. Mitelman, Catalog of Chromosome Aberrations in Cancer, New York: Alan R. Liss, 1988). Because the breakpoint of chromosome 22 in the translocation t(12;22)(q13;12) cannot be cytogenetically distinguished from that of the translocation t(11;22), the inventors have studied the rearrangement of the Ews gene in the translocation t(12;22).

SUMMARY OF THE INVENTION

The invention consequently relates to a nucleic acid including all or part of the nucleotide sequence of the Ews gene of chromosome 22, located at the level of the breakpoint of this chromosome in various recurrent chromosomal translocations associated with the development of cancerous tumors.

The invention also relates to the hybrid DNAs relating from the fusion of the Ews gene with other genes at the time of recurrent chromosomal translocations involving chromosome 22, essentially constituted by part of the nucleotide sequence of the Ews gene and by part of the nucleotide sequence of the gene located at the level of the breakpoint of the other chromosome involved in the translocation.

More particularly, the invention relates to the hybrid DNAs essentially including the part of the nucleotide sequence of the Ews gene up to the 7 Kb region at the level of which the breakpoint of chromosome 22 is located.

Among these hybrid DNAs including the part of the nucleotide sequence of the Ews gene from its origin up to the 7 Kb region at the level of which the breakpoint of chromosome 22 is located, the invention relates more particularly to those resulting from the following chromosomal translocations:

t(11;22)(q24;q12), associated with at least 80% of cases of Ewing's sarcoma or related tumors;

t(11;22), associated with at least 10% of cases of Ewing's sarcoma or related tumors;

t(12;22), associated with soft tissue malignant melanoma.

The invention also relates to the mRNAs originating in the DNA of the gene of chromosome 22 and the fusion DNAs, as well as the cDNAs that can derive from them, as well as the proteins for which they code.

Accordingly, the subject of the invention is the hybrid DNAs resulting from the translocation t(11;22)(q24;q12) essentially constituted by the fusion of a part of the nucleotide sequence of the Ews gene and the part of the nucleotide sequence of the Hum-Fli-1 gene located at the level of the breakpoint of chromosome 11 in said translocation. More precisely, the invention relates to the hybrid DNAs including the part of the nucleotide sequence of the Hum-Fli-1 gene from the 40 Kb region EWSR2 at the level of which the breakpoint of chromosome 11 is located in this translocation, up to its 3' end.

The inventors have studied in detail the mechanisms that give rise to the various fusion genes of the translocation t(11;22).

The exon structures of the Ews and Hum-Fli-1 genes have been determined. It appears that the precise positions of the breakpoints located at the level of the regions EWSR1 and EWSR2 are most often located, and can exclusively be within, the introns of the two genes, so that by the set of splices that occur in the course of the maturation of the primary transcript, an open reading frame can be restored. The position of the exons with respect to the restriction sites has been defined for the Ews and Hum-Fli-1 genes.

The open reading frames are divided, and each intron between two coding exons interrupts the reading frames; the determination of the majority of the intron-exon junctions has been done for both the Ews and the Hum-Fli-1 genes.

Based on this work, it has been possible to deduce the approximate size of the introns, sites of the chromosomal breakpoints, and to contemplate a great number of possible fusion products. Furthermore, the promoter sequence of the EWS gene has been determined.

Advantageously, the hybrid DNAs according to the invention corresponding to the fusion products relating from the recurrent chromosomal translocation t(11;22) are essentially constituted by a part of the nucleotide sequence of the cDNA of the Ews gene, and more precisely the nucleotide sequence of a cDNA resulting from the fusion of the Ews and Hum-Fli-1 genes.

Nucleotide probes or their homologues, capable of hybridizing with all or part of the nucleotide sequence of the Ews or Hum-Fli-1 genes or with the cDNA of one of these genes, have been prepared. Among them, probes capable of hybridizing specifically with a part of the Ews gene or a part of the Hum-Fli-1 gene have been selected.

Probes that are complementary to all or part of the hybrid DNAs, in particular corresponding to the part of the Ews and Hum-Fli-1 genes altered by the translocation t(11;22), or with the mRNA or cDNA of the fusion genes, have also been obtained with a view to detecting, by hybridization, the possible presence of a translocation t(11;22) in the tumor cells of a subject.

Synthetic oligonucleotides have been prepared from the nucleotide sequences of the Ews, Hum-Fli-1 genes and the products resulting from the fusion of these two genes, in order to prepare the cDNA corresponding to the fusion zone by reverse transcription of mRNA originating in a specimen to be analyzed. In vitro gene amplification of this cDNA by PCR, with the aid of oligonucleotide primers, enables the analysis of the amplified products by simple radioactive methods or colorimetric methods of the gel electrophoresis and ethidium bromide coloration type, or by immunological or fluorographic detection.

Consequently, the invention relates to the nucleotide sequences, or their analogs, that constitute genetic probes capable of hybridizing with the nucleotide sequence of the Ews gene, or the hybrid DNAs resulting from the fusion of the Ews and Hum-Fli-1 genes, or their mRNAs and cDNAs, as well as the oligonucleotides originating in these sequences and constituting primers for performing reverse RNA transcription or the implementation of a PCR gene amplification process.

The chromosomal translocation t(11;22) observed in neurectodermic tumors gives rise to hybrid fusion genes capable of coding for the chimera proteins that have preserved the N-terminal part of the EWS protein coded by the Ews gene and the C-terminal part of the HUM-FLI-1 protein coded by the Hum-Fli-1 gene.

Thorough study of the Ews gene shows that it codes for a protein with 656 amino acids with two domains of different structure. The C-terminal part is characterized by three regions rich in glycine and arginine residues and one region of 85 amino acid homologous to the RNA fixation consensus domain; this strongly suggests that the C-terminal part of the EWS protein could interact with single-strand nucleic acids, and more particularly with RNA. The N-terminal portion of the EWS protein (NTD-EWS) includes a repeated and degenerated polypeptide that has a consensus sequence SYGQQS which has weak homology with CTD-PolII.

The amino acid sequence of the chimera proteins can be deduced from the fusion cDNAs resulting from the translocation t(11;22); several of these proteins have been produced in vitro, in order in particular to prepare polyclonal or monoclonal antibodies capable of fusing with the cells that produce these proteins, and consequently that exhibit the translocation t(11;22). The invention accordingly also relates to the chimera proteins resulting from the chromosomal translocation t(11;22), as well as the antibodies for immunological detection of the presence of these proteins, and more particularly a chimera protein, in a biological specimen taken from a subject likely to carry a chromosomal translocation t(11;22).

The invention also relates to the methods of detecting a fusion gene resulting from the chromosomal translocation t(11;22).

BRIEF DESCRIPTION OF THE FIGURES

Figures 1A, 1B, 1C:
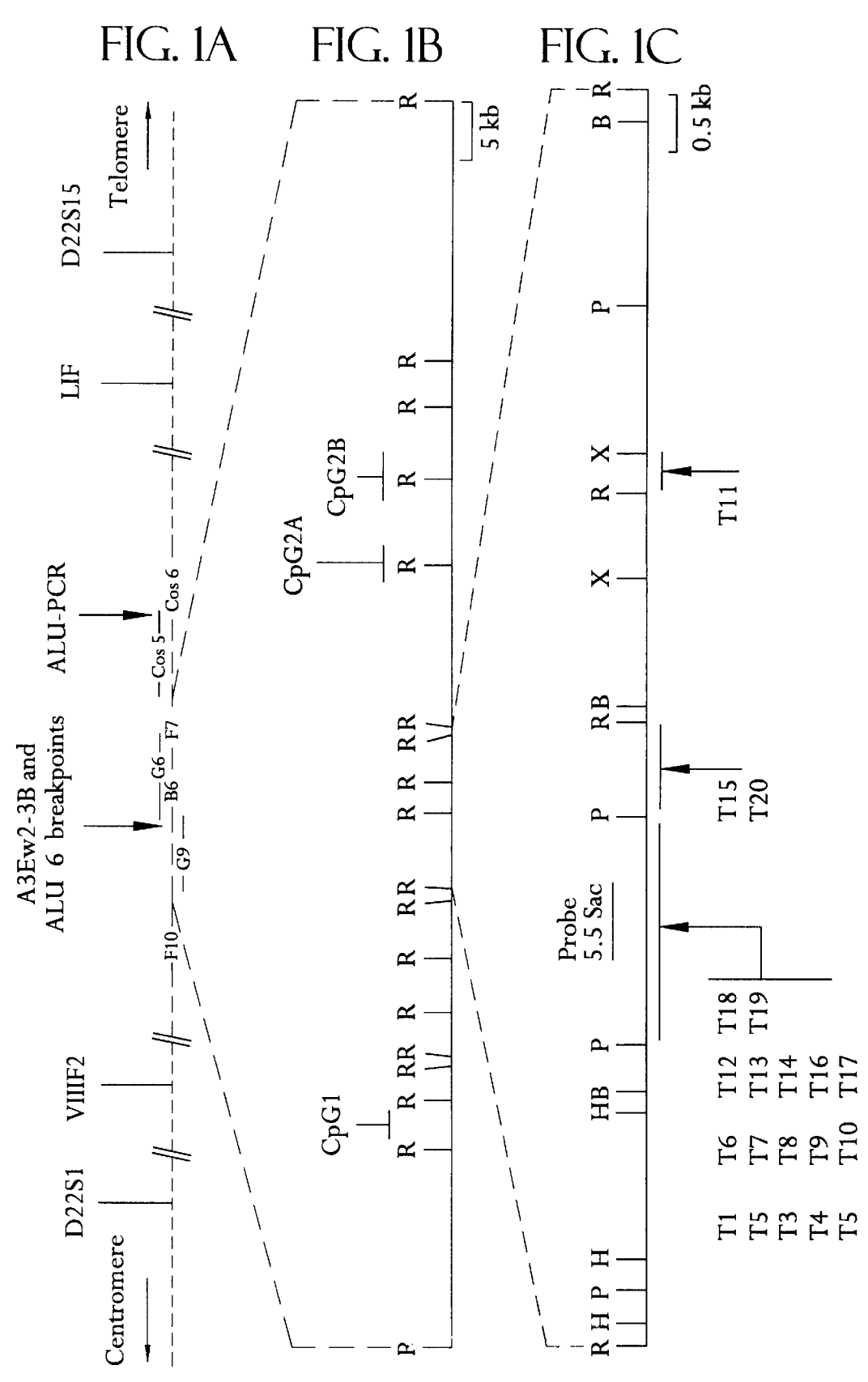

FIG. 1 shows a map of the region EWSR1 on chromosome 22.

FIG. 6 shows the DNA sequence of the gene Ews (SEQ ID NO:1) and the amino acid sequence (SEQ ID NO:2) encoded by the DNA sequence.

FIG. 7 shows the DNA sequence of the gene Hum-Fli-1 (SEQ ID NO:3) and the amino acid sequence (SEQ ID NO:4) encoded by the DNA sequence.

FIG. 8 shows the nucleotide sequence of the fusion cDNA of the Ews gene (SEQ ID NO:5) and the Hum-Fli-1 gene (SEQ ID NO:6).

FIG. 12 shows the exon structure of the Ews gene, including Exon 1 (SEQ ID NO:14), Exon 2 (SEQ ID NO:15, SEQ ID NO:16), Exon 3 (SEQ ID NO:17, SEQ ID NO:18), Exon 4 (SEQ ID NO:19, SEQ ID NO:20), Exon 5 (SEQ ID NO:21, SEQ ID NO:22), Exon 6 (SEQ ID NO:23, SEQ ID NO:24), Exon 7 (SEQ ID NO:25, SEQ ID NO:26), Exon 8 (SEQ ID NO:27, SEQ ID NO:28), Exon 9 (SEQ ID NO:29, SEQ ID NO:30), Exon 10, (SEQ ID NO:31, SEQ ID NO:32), Exon 11 (SEQ ID NO:33, SEQ ID NO:34), Exon 12 (SEQ ID NO:35, SEQ ID NO:36), Exon 13, (SEQ ID NO:37, SEQ ID NO:38), Exon 14 (SEQ ID NO:39, SEQ ID NO:40), Exon 15 (SEQ ID NO:41, SEQ ID NO:42), Exon 16 (SEQ ID NO:43, SEQ ID NO:44) and Exon 17 (SEQ ID NO:45).

FIG. 13 shows the exon structure of the Hum-Fli-1 gene, including Exon 1 (SEQ ID NO:46), Exon 2 (SEQ ID NO:47, SEQ ID NO:48), Exon 3 (SEQ ID NO:49, SEQ ID NO:50), Exon 4 (SEQ ID NO:51, SEQ ID NO:52), Exon 5 (SEQ ID NO:53, SEQ ID NO:54), Exon 6 (SEQ ID NO:55, SEQ ID NO:56), Exon 7 (SEQ ID NO:57, SEQ ID NO:58), Exon 8 (SEQ ID NO:59, SEQ ID NO:60), and Exon 9 (SEQ ID NO:61, SEQ ID NO:62).

FIG. 17 shows the DNA sequence of the promoter region of the Ews gene (SEQ ID NO:97).

FIG. 22 (SEQ ID NO:106) shows the DNA sequence of a fusion gene of Ews and Atf-1 and the amino acid sequence (SEQ ID NO:107) encoded by the DNA.

FIG. 23 shows the partial sequence of the cDNA of the Ews and Atf-1 genes (SEQ ID NO:111/SEQ ID NO:112, SEQ ID NO:113/SEQ ID NO:114, SEQ ID NO:115/SEQ ID NO:116) and of hybrid DNA of the Ews and Atf-1 genes (SEQ ID NO:108 and SEQ ID NO:109/SEQ ID NO:110) in the junction region.

Figure 2:
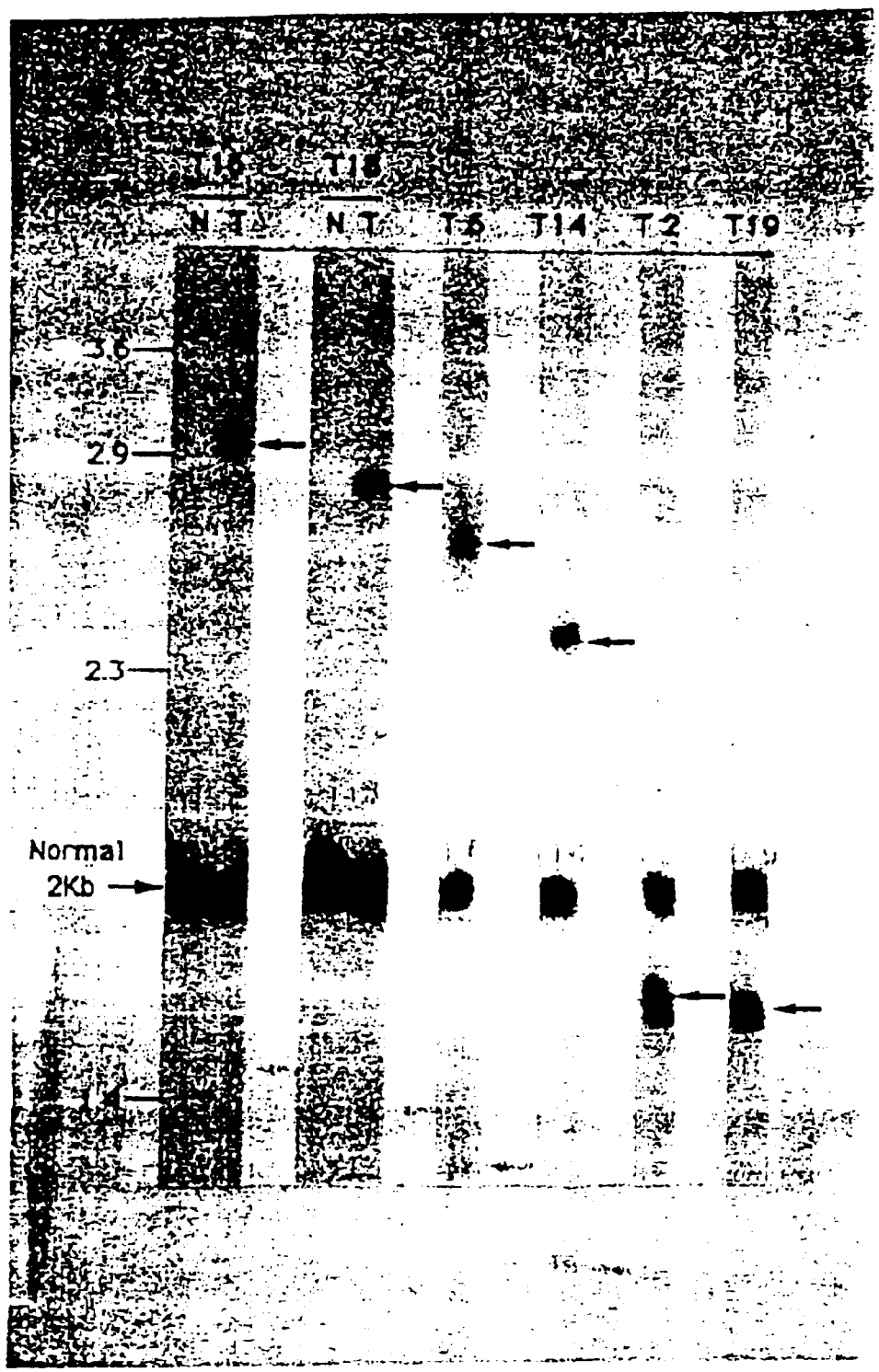
FIG. 2 shows the detection of abnormal genome fragments in six tumors.

In a first embodiment, a method for detecting such a gene includes the following steps:

the treatment of a biological specimen derived from tumor cells of a patient that are likely to have a chromosomal translocation t(11;22), in such a way as to render the nucleic acids that it contains capable of hybridizing with a probe;

putting at least one probe of the invention specific to either part of the nucleotide sequence of the Ews gene or the nucleotide sequence of a fusion gene resulting from the translocation t(11;22) into contact with the biological specimen, under conditions enabling the formation of hybridization complexes between the probe or probes and the target DNA or RNA contained in the specimen;

the determination by any suitable means of the hybrids possibly formed.

This method may be employed in tests on a membrane or a slide or any other suitable substrate, by the dot blot or Southern blot methods or by filtration methods.

A second embodiment of such a method seeks to detect the transcript of a fusion gene resulting from the translocation t(11;22); this method consists of performing reverse transcription with the aid of an appropriate synthetic oligonucleotide to obtain a corresponding cDNA from the mRNA extracted from a biological specimen taken from tumor cells of a patient likely to have a chromosomal translocation t(11;22); then amplifying this cDNA, with the aid of DNA polymerase and appropriate primers, by an enzymatic amplification process known as PCR that consists of repeating the cycles of DNA denaturation, hybridizing the primers and extending from the primers, a sufficient number of times to increase the quantity of the starting sequence in an exponential proportion relative to the number of cycles implemented. The amplification products are analyzed, for example by electrophoresis, to detect the presence of a product corresponding to one or the other of the genes involved in the translocation t(11;22), or a fusion gene. Methods of detecting the amplified products by adsorption on microslides are also possible.

The invention also relates to the detection of a chimera protein coded by a fusion gene resulting from the translocation t(11;22). Such a method includes the following steps:

the treatment of a biological specimen deriving from a patent whose tumor cells are likely to have a translocation t(11;22), in such a way as to render the proteins that it contains accessible to antibodies;

putting the biological specimen into contact with at least one antibody of the invention specific to the one chimera protein of the invention corresponding to the translocation t(11;22), under conditions enabling the formation of immunological complexes between the antibody or antibodies and the proteins present in the cells of the specimen;

the determination by any suitable means of the immunological complexes possibly formed.

Specifically, the detection of fusion DNA or RNA or of a chimera protein enables diagnosis of Ewing's sarcoma and related tumors in subjects who have small cell tumors.

Consequently, the subject of the invention is a method of diagnosing Ewing's sarcoma and related tumors, consisting of detecting the presence of a translocation t(11;22) in the tumor cells, from a biological specimen derived from tumor cells of a patient that are likely to have a chromosomal translocation t(11;22), the specimen to be treated in such a way as to render the nucleic acids that it contains capable of hybridizing with a probe. Such a method includes the following steps:

putting at least one probe of the invention, optionally labeled, specific to either part of the nucleotide sequence of the Ews gene or the nucleotide sequence of a fusion gene resulting from the translocation t(11;22), into contact with the biological specimen, treated in such a way that the cells that it contains are lysed and optionally that the nucleic acids contained in said cells are fragmented with the aid of restriction enzyme, under conditions enabling the formation of hybridization complexes between the probe or probes and the target DNA or RNA contained in the specimen;

the determination by any suitable means of the hybrids possibly formed, to detect the presence of a product corresponding to the fusion gene resulting from the translocation t(11;22).

As before, this method may be employed in tests on a membrane or on a slide or any other suitable substrate by the dot blot or Southern blot or filtration methods.

In another embodiment, a method for diagnosing Ewing's sarcoma and related tumors consists of performing reverse transcription with the aid of an appropriate synthetic oligonucleotide to obtain a corresponding cDNA from the mRNA extracted from a biological specimen taken from tumor cells of a patient likely to have a chromosomal translocation t(11;22); then amplifying this cDNA, with the aid of DNA polymerase and appropriate primers, by an enzymatic amplification process known as PCR that consists of repeating the cycles of DNA denaturation, hybridizing the primers and extending from the primers, a sufficient number of times to increase the quantity of the starting sequence in an exponential proportion relative to the number of cycles implemented. The amplification products are analyzed, for example by electrophoresis, to detect the presence of a product corresponding to a fusion gene of the translocation t(11;22). Methods of detecting the amplified products by adsorption on microslides are also possible.

In another embodiment, a method for diagnosing Ewing's sarcoma and related tumors consists of immunologically detecting the presence of at least one protein coded by one or more fusion genes resulting from the translocation t(11;22), from a cell specimen put into contact with one or more antibodies of the invention specific to fusion proteins corresponding to the translocation t(11;22). Such a method includes the following steps:

the treatment of a biological specimen deriving from a patent whose tumor cells are likely to have a translocation t(11;22), in such a way as to render the proteins that it contains accessible to antibodies;

putting the biological specimen into contact with at least one antibody of the invention directed against at least one chimera protein resulting from the translocation t(11;22), under conditions enabling the formation of immunological complexes between the antibody or antibodies and the proteins present in the cells of the specimen;

the determination by any suitable means of the immunological complexes possibly formed, to detect the presence of a product corresponding to the fusion gene resulting from the translocation t(11;22).

Kits for implementing these methods can advantageously be prepared. These kits, in the case of a method by hybridization, contain probes according to the invention as well as control specimens of DNA or RNA. In the case of a method by reverse transcription and PCR, they contain the appropriate oligonucleotides for implementing each of these techniques as well as control specimens of DNA or RNA; in the case of an immunological method, they contain the monoclonal antibodies as well as control specimens of known reactivity.

The invention also relates to the use of DNA sequences of the invention to prepare anti-sense nucleotides, or analogs, having an anti-tumor activity, which by hybridization with all or part of the fusion gene inhibit its transcription and thus prevent the production of mRNA and chimera proteins and/or in another embodiment, they hybridize with the transcription mRNA and thus inhibit the production of chimera proteins.

Consequently, the invention relates to the use of a nucleic acid or an analog of this nucleic acid, capable of hybridizing with the nucleotide sequence of a hybrid DNA of the invention, for preparing a therapeutic agent that inhibits the expression of a fusion gene resulting from a chromosomal translocation t(11;22)(q24;q12), in tumor cells of patients suffering from Ewing's sarcoma or related tumors.

Accordingly, the subject of the invention is also a therapeutic agent for inhibiting the expression of a fusion gene resulting from a chromosomal translocation t(11;22) (q24;q12), in tumor cells of patients suffering from Ewing's sarcoma or related tumors, characterized in that it is essentially constituted by a hybrid DNA of the invention, or an analog of this DNA, capable of hybridizing with the nucleotide sequence of a fusion gene resulting from the chromosomal translocation t(11;22)(q24;q12).

In another embodiment, the invention relates to the use of a nucleic acid or an analog of this nucleic acid, capable of hybridizing with the nucleotide sequence of a hybrid RNA of the invention, for preparing a therapeutic agent that inhibits the translation of chimera proteins resulting from a chromosomal translocation t(11;22)(q24;q12), in tumor cells of patients suffering from Ewing's sarcoma or related tumors.

Hence the subject of the invention is also a therapeutic agent for inhibiting the translation of chimera proteins resulting from a chromosomal translocation t(11;22) (q24;q12), in tumor cells of patients suffering from Ewing's sarcoma or related tumors, characterized in that it is essentially constituted by a hybrid RNA of the invention, or an analog of this RNA, capable of hybridizing with the nucleotide sequence of the RNA originating in a fusion gene resulting from the chromosomal translocation t(11;22) (q24;q12).

The invention also has as its subject the hybrid DNAs resulting from the translocation t(21;22) associated with approximately 10% of cases of Ewing's sarcoma or related tumors, essentially constituted by the fusion of a part of the nucleotide sequence of the Ews gene, and of the part of the nucleotide sequence of the Erg gene located at the level of the breakpoint of chromosome 21 in the translocation. More precisely, the invention relates to the hybrid DNAs including the part of the nucleotide sequence of the Erg gene from the region at the level of which the breakpoint of chromosome 21 is located in this translocation, to its end 3'.

The inventors have studied in detail the mechanisms giving rise to the various fusion genes of the translocation t(21;22).

Advantageously, the hybrid DNAs according to the invention corresponding to the fusion products relating from the recurrent chromosomal translocation t(21;22) are essentially constituted by a part of the nucleotide sequence of the cDNA of the Ews gene, and more precisely the nucleotide sequence of a cDNA resulting from the fusion of the Ews and Erg genes.

Nucleotide probes or their homologues, capable of hybridizing with all or part of the nucleotide sequence of the Ews or Erg genes or with the cDNA of one of these genes, had been prepared. Among them, probes capable of hybridizing specifically with a part of the Ews gene or a part of the Erg gene have been selected.

Probes that are complementary to all or part of the hybrid DNAs, in particular corresponding to the part of the Ews and Erg genes altered by the translocation t(21;22), or with the mRNA or cDNA of the fusion genes, have also been obtained with a view to detecting, by hybridization, the possible presence of a translocation t(21;22) in the tumor cells of a subject.

Synthetic oligonucleotides have been prepared from the nucleotide sequences of the Ews, Erg genes and the products resulting from the fusion of these two genes, in order to prepare the cDNA corresponding to the fusion zone by reverse transcription of mRNA originating in a specimen to be analyzed. In vitro gene amplification of this cDNA by PCR, with the aid of oligonucleotide primers, enables the analysis of the amplified products by simple radioactive methods or colorimetric methods of the gel electrophoresis and ethidium bromide coloration type, or by immunological or fluorographic detection.

Consequently, the invention relates to the nucleotide sequences, or their analogs, that constitute genetic probes capable of hybridizing with the nucleotide sequence of the Ews gene, or the hybrid DNAs resulting from the fusion of the Ews and Erg genes, or their mRNAs and cDNAs, as well as the oligonucleotides originating in these sequences and constituting primers for performing reverse RNA transcription or the implementation of a PCR gene amplification process.

The chromosomal translocation t(21;22) observed in neurectodermic tumors gives rise to hybrid fusion genes capable of coding for the chimera proteins that have preserved the N-terminal part of the EWS protein coded by the Ews gene and the C-terminal part of the ERG protein coded by the Erg gene.

As in the case of the chimera proteins resulting from the fusion of the Ews and Hum-Fli-1 genes, the chimera proteins resulting from the translocation t(21;22) reserve the NTD-EWS domain, which is in phase with the DNA fixation domain of the protein ERG.

The amino acid sequence of the chimera proteins can be deduced from the fusion cDNAs resulting from the translocation t(21;22); certain ones of these proteins have been produced in vitro in order in particular to prepare polyclonal and monoclonal antibodies capable of fusing with the cells that produce these proteins, and consequently that have the translocation t(21;22). Accordingly, the invention also relates to the chimera proteins resulting from the chromosomal translocation t(21;22), as well as the antibodies for the immunological detection of the presence of these proteins, and more particularly of a chimera protein in a biological specimen taken from a subject likely to carry a chromosomal translocation t(21;22). The invention also relates to the methods of detecting a fusion gene resulting from the chromosomal translocation t(21;22).

In a first embodiment, a method for detecting such a gene includes the following steps:

the treatment of a biological specimen derived from tumor cells of a patient that are likely to have a chromosomal translocation t(21;22), in which a way as to render the nucleic acids that it contains capable of hybridizing with a probe;

putting at least one probe of the invention, specific to either part of the nucleotide sequence of the Ews gene or the nucleotide sequence of a fusion gene corresponding to the translocation t(21;22), into contact with the biological specimen, under conditions enabling the formation of hybridization complexes between the probe or probes and the target DNA or RNA contained in the specimen;

the determination by any suitable means of the hybrids possibly formed.

This method may be employed in tests on a membrane or a slide or any other suitable substrate, by the dot blot or Southern blot methods or by filtration methods.

A second embodiment of such a method seeks to detect the transcript of a fusion gene resulting from the translocation t(21;22); this method consists of performing reverse transcription with the aid of an appropriate synthetic oligonucleotide to obtain a corresponding cDNA, from the mRNA extracted from a biological specimen taken from tumor cells of a patient likely to have a chromosomal translocation t(21;22); then amplifying this cDNA, with the aid of DNA polymerase and appropriate primers, by an enzymatic amplification process known as PCR that consists of repeating the cycles of DNA denaturation, hybridizing the primers and extending from the primers, a sufficient number of times to increase the quantity of the starting sequence in an exponential proportion relative to the number of cycles implemented. The amplification products are analyzed, for example by electrophoresis, to detect the presence of a product corresponding to one or the other of the genes involved in the translocation t(21;22), or a fusion gene. Methods of detecting the amplified products by adsorption on microslides are also possible.

The invention also relates to the detection of a chimera protein coded by a fusion gene resulting from the translocation t(21;22). Such a method includes the following steps:

the treatment of a biological specimen deriving from a patent whose tumor cells are likely to have a translocation t(21;22), in such a way as to render the proteins that it contains accessible to antibodies;

putting the biological specimen into contact with at least one antibody specific to the chimera protein of the invention corresponding to the translocation t(21;22), under conditions enabling the formation of immunological complexes between the antibody or antibodies and the proteins present in the cells of the specimen;

the determination by any suitable means of the immunological complexes possibly formed.

Specifically, the detection of fusion DNA or RNA resulting from the translocation t(21;22) or of a corresponding chimera protein enables the diagnosis of Ewing's sarcoma and related tumors in subjects who have small cell tumors.

Consequently, the subject of the invention is a method for diagnosing Ewing's sarcoma and related tumors, consisting of detecting the presence of a translocation t(21;22) in the tumor cells, from a biological specimen derived from tumor cells of a patient that are likely to have a chromosomal translocation t(21;22), the specimen to be treated in such a way as to render the nucleic acids that it contains capable of hybridizing with a probe. Such a method includes the following steps:

putting at least one probe of the invention, optionally labeled, specific to either part of the nucleotide sequence of the Ews gene or the nucleotide sequence of a fusion gene resulting from the translocation t(21;22), into contact with the biological specimen, treated in such a way that the cells it contains are lysed and optionally that the nucleic acids contained in said cells are fragmented with the aid of restriction enzyme, under conditions enabling the formation of hybridization complexes between the probe or probes and the target DNA or RNA contained in the specimen;

the determination by any suitable means of the hybrids possibly formed, to detect the presence of a product corresponding to the fusion gene resulting from the translocation t(21;22).

This method may be employed in tests on a membrane or a slide or any other suitable substrate, by the dot blot or Southern blot methods or by filtration methods.

In another embodiment, a method for diagnosing Ewing's sarcoma and related tumors consists of performing reverse transcription with the aid of an appropriate synthetic oligonucleotide to obtain a corresponding cDNA from the mRNA extracted from a biological specimen taken from tumor cells of a patient likely to have a chromosomal translocation t(21;22); then amplifying this cDNA, with the aid of DNA polymerase and appropriate primers, by an enzymatic amplification process known as PCR that consists of repeating the cycles of DNA denaturation, hybridizing the primers and extending from the primers, a sufficient number of times to increase the quantity of the starting sequence in an exponential proportion relative to the number of cycles implemented. The amplification products are analyzed, for example by electrophoresis, to detect the presence of a product corresponding to a fusion gene of the translocation t(21;22). Methods of detecting the amplified products by adsorption on microslides are also possible.

In another embodiment, a method for diagnosing Ewing's sarcoma and related tumors consists of immunologically detecting, from a cell specimen put into contact with one or more antibodies of the invention that are specific to fusion proteins, the presence of at least one protein coded by one or more fusion genes resulting from the translocation t(21;22). Such a method includes the following steps:

the treatment of a biological specimen deriving from a patent whose tumor cells are likely to have a translocation t(21;22), in such a way as to render the proteins that it contains accessible to monoclonal antibodies;

putting the biological specimen into contact with at least one antibody of the invention, directed against at least one chimera protein corresponding to the translocation t(21;22), under conditions enabling the formation of immunological complexes between the antibody or antibodies and the proteins present in the cells of the specimen;

the determination by any suitable means of the immunological complexes possibly formed, to detect the presence of a product corresponding to the fusion gene resulting from the translocation t(21;22).

Since translocation t(21;22) is associated with approximately 10% of cases of Ewing's sarcoma, and translocation t(11;22) is associated with at least 80% of the cases of Ewing's sarcoma, it is advantageous, to enable diagnosis of Ewing's sarcoma, to simultaneously employ the methods that seek to detect the products resulting from these two translocations in the tumor cells of patients likely to exhibit these chromosomal translocations.

Kits for implementing these methods can advantageously be prepared. These kits, in the case of a method by hybridization, contain probes according to the invention as well as control specimens of DNA or RNA. In the case of a method by reverse transcription and PCR, they contain the appropriate oligonucleotides for implementing each of these techniques as well as control specimens of DNA or RNA; in the case of an immunological method, they contain the monoclonal antibodies as well as control specimens of known reactivity.

The invention also relates to the use of DNA sequences of the invention to prepare anti-sense nucleotides, or analogs, having an anti-tumor activity, which by hybridization with all or part of the fusion gene inhibit its transcription and thus prevent the production of mRNA and chimera proteins and/or in another embodiment, they hybridize with the transcription mRNA and thus inhibit the production of chimera proteins.

The invention consequently relates to the use of a nucleic acid or an analog of this nucleic acid, capable of hybridizing with the nucleotide sequence of a hybrid DNA corresponding to the translocation t(21;22) of the invention, for preparing a therapeutic agent that inhibits the expression of a fusion gene resulting from said chromosomal translocation, in tumor cells of patients suffering from Ewing's sarcoma or related tumors.

Accordingly the subject of the invention is also a therapeutic agent for inhibiting the expression of a fusion gene resulting from the chromosomal translocation t(21;22) in tumor cells of patients suffering from Ewing's sarcoma or related tumors, characterized in that it is essentially constituted by a hybrid DNA of the invention corresponding to said translocation, or an analog of this DNA, capable of hybridizing with the nucleotide sequence of a fusion gene resulting from the chromosomal translocation t(21;22).

In another embodiment, the invention relates to the use of a nucleic acid or an analog of this nucleic acid, capable of hybridizing with the nucleotide sequence of a hybrid RNA according to the invention corresponding to the translocation t(21;22), for preparing a therapeutic agent that inhibits the translation of chimera proteins resulting from such a chromosomal translocation, in tumor cells of patients suffering from Ewing's sarcoma or related tumors.

Hence, the subject of the invention is also a therapeutic agent for inhibiting the translation of chimera proteins resulting from a chromosomal translocation t(21;22), in tumor cells of patients suffering from Ewing's sarcoma or related tumors, characterized in that it is essentially constituted by a hybrid RNA of the invention corresponding to the translocation t(21;22), or an analog of this RNA, capable of hybridizing with the nucleotide sequence of the RNA originating in a fusion gene resulting from this chromosomal translocation.

Since the translocation t(21;22) is associated with approximately 10% of cases of Ewing's sarcoma, and the translocation t(11;22) is associated with at least 80% of the cases of Ewing's sarcoma, the invention advantageously relates to a therapeutic agent, essentially constituted by either therapeutic agents that inhibit the expression of the fusion genes resulting from these two chromosomal translocations, or therapeutic agents that inhibit the translation of the fusion genes resulting from these two chromosomal translocations.

Finally, the subject of the invention is the hybrid DNAs resulting from the translocation t(12;22)(q13;q12), essentially constituted by the fusion of a part of the nucleotide sequence of the gene Ews and the part of the nucleotide sequence of the Atf-1 gene located at the level of the breakpoint of chromosome 12 in this translocation. More precisely, the invention relates to the hybrid DNAs including the part of the nucleotide sequence of the Atf-1 gene from the region at the level of which the breakpoint of chromosome 12 is located in this translocation, up to its 3' end.

The inventors have studied in detail the mechanisms giving rise to the various fusion genes of the translocation t(11;22).

Advantageously, the hybrid DNAs according to the invention corresponding to the fusion products relating from the recurrent chromosomal translocation t(12;22) are essentially constituted by a part of the nucleotide sequence of the cDNA of the Ews gene, and more precisely the nucleotide sequence of a cDNA resulting from the fusion of the Ews and Atf-1 genes.

Nucleotide probes or their homologues, capable of hybridizing with all or part of the nucleotide sequence of the Ews or Atf-1 genes or with the cDNA of one of these genes, had been prepared. Among them, probes capable of hybridizing specifically with a part of the Ews gene or a part of the Atf-1 gene have been selected.

Probes that are complementary to all or part of the hybrid DNAs, in particular corresponding to the part of the Ews and Atf-1 genes altered by the translocation t(12;22), or with the mRNA or cDNA of the fusion genes, have also been obtained with a view to detecting, by hybridization, the possible presence of a translocation t(12;22) in the tumor cells of a subject.

Synthetic oligonucleotides have been prepared from the nucleotide sequences of the Ews, Atf-1 genes and the products resulting from the fusion of these two genes, in order to prepare the cDNA corresponding to the fusion zone by reverse transcription of mRNA originating in a specimen to be analyzed. In vitro gene amplification of this cDNA by PCR, with the aid of oligonucleotide primers, enables the analysis of the amplified products by simple radioactive methods or colorimetric methods of the gel electrophoresis and ethidium bromide coloration type, or by immunological or fluorographic detection.

Consequently, the invention relates to the nucleotide sequences, or their analogs, that constitute genetic probes capable of hybridizing with the nucleotide sequence of the Ews gene, or the hybrid DNAs resulting from the fusion of the Ews and Atf-1 genes, or their mRNAs and cDNAs, as well as the oligonucleotides originating in these sequences and constituting primers for performing reverse RNA transcription or the implementation of a PCR gene amplification process.

The chromosomal translocation t(12;22) observed in soft tissue malignant melanoma (STMM) tumors gives rise to hybrid fusion genes capable of coding for the chimera proteins that have preserved the N-terminal part of the EWS protein coded by the Ews gene and the C-terminal part of the ATF-1 protein coded by the Atf-1 gene.

The amino acid sequence of the chimera proteins can be deduced from the fusion cDNAs resulting from the translocation t(12;22); one of these proteins has been produced in vitro, in order in particular to prepare polyclonal or monoclonal antibodies capable of fusing with the cells that produce this protein, and consequently that exhibit the translocation t(12;22). The invention accordingly also relates to the chimera proteins resulting from the chromosomal translocation t(12;22), as well as the antibodies for immunological detection of the presence of these proteins, and more particularly a chimera protein, in a biological specimen taken from a subject likely to carry a chromosomal translocation t(12;22).

The invention also relates to the methods of detecting a fusion gene resulting from the chromosomal translocation t(12;22).

In a first embodiment, a method for detecting such a gene includes the following steps:

the treatment of a biological specimen derived from tumor cells of a patient that are likely to have a chromosomal translocation t(12;22), in such a way as to render the nucleic acids that it contains capable of hybridizing with a probe;

putting at least one probe of the invention specific to either part of the nucleotide sequence of the Ews gene or the nucleotide sequence of a fusion gene resulting from the translocation t(12;22), or a mixture of these probes, into contact with the biological specimen, under conditions enabling the formation of hybridization complexes between the probe or probes and the target DNA or RNA contained in the specimen;

the determination by any suitable means of the hybrids possibly formed.

This method may be employed in tests on a membrane or a slide or any other suitable substrate, by the dot blot or Southern blot methods or by filtration methods.

A second embodiment of such a method seeks to detect the transcript of a fusion gene resulting from the translocation t(12;22); this method consists of performing reverse transcription with the aid of an appropriate synthetic oligonucleotide to obtain a corresponding cDNA from the mRNA extracted from a biological specimen taken from tumor cells of a patient likely to have a chromosomal translocation t(12;22); then amplifying this cDNA, with the aid of DNA polymerase and appropriate primers, by an enzymatic amplification process known as PCR that consists of repeating the cycles of DNA denaturation, hybridizing the primers and extending from the primers, a sufficient number of times to increase the quantity of the starting sequence in an exponential proportion relative to the number of cycles implemented. The amplification products are analyzed, for example by electrophoresis, to detect the presence of a product corresponding to one or the other of the genes involved in the translocation t(12;22), or a fusion gene. Methods of detecting the amplified products by adsorption on microslides are also possible.

The invention also relates to the detection of a chimera protein coded by a fusion gene resulting from the translocation t(12;22). Such a method includes the following steps:

the treatment of a biological specimen deriving from a patent whose tumor cells are likely to have a translocation t(12;22), in such a way as to render the proteins that it contains accessible to antibodies;

putting the biological specimen into contact with at least one antibody of the invention specific to the one chimera protein of the invention corresponding to the translocation t(12;22), under conditions enabling the formation of immunological complexes between the antibody or antibodies and the proteins present in the cells of the specimen;

the determination by any suitable means of the immunological complexes possibly formed.

Specifically, the detection of fusion DNA or RNA or of a chimera protein enables diagnosis of STMM.

Consequently, the subject of the invention is a method of diagnosing STMM, consisting of detecting the presence of a translocation t(12;22) in the tumor cells, from a biological specimen derived from tumor cells of a patient that are likely to have a chromosomal translocation t(12;22), the specimen to be treated in such a way as to render the nucleic acids that it contains capable of hybridizing with a probe. Such a method includes the following steps:

putting at least one probe of the invention, optionally labeled, specific to either part of the nucleotide sequence of the Ews gene or the nucleotide sequence of a fusion gene resulting from the translocation t(12;22), into contact with the biological specimen, treated in such a way that the cells that it contains are lysed and optionally that the nucleic acids contained in said cells are fragmented with the aid of restriction enzyme, under conditions enabling the formation of hybridization complexes between the probe or probes and the target DNA or RNA contained in the specimen;

the determination by any suitable means of the hybrids possibly formed, to detect the presence of a product corresponding to the fusion gene resulting from the translocation t(12;22).

As before, this method may be employed in tests on a membrane or on a slide or any other suitable substrate by the dot blot or Southern blot or filtration methods.

In another embodiment, a method for diagnosing STMM consists of performing reverse transcription with the aid of an appropriate synthetic oligonucleotide to obtain a corresponding cDNA from the mRNA extracted from a biological specimen taken from tumor cells of a patient likely to have a chromosomal translocation t(12;22); then amplifying this cDNA, with the aid of DNA polymerase and appropriate primers, by an enzymatic amplification process known as PCR that consists of repeating the cycles of DNA denaturation, hybridizing the primers and extending from the primers, a sufficient number of times to increase the quantity of the starting sequence in an exponential proportion relative to the number of cycles implemented. The amplification products are analyzed, for example by electrophoresis, to detect the presence of a product corresponding to a fusion gene of the translocation t(11;22). Methods of detecting the amplified products by adsorption on microslides are also possible.

In another embodiment, a method for diagnosing STMM consists of immunologically detecting the presence of at least one protein coded by one or more fusion genes resulting from the translocation t(12;22), from a cell specimen put into contact with one or more antibodies of the invention specific to fusion proteins. Such a method includes the following steps:

the treatment of a biological specimen deriving from a patent whose tumor cells are likely to have a translocation t(12;22), in such a way as to render the proteins that it contains accessible to antibodies;

putting the biological specimen into contact with at least one antibody of the invention directed against at least one chimera protein resulting from the translocation t(12;22), under conditions enabling the formation of immunological complexes between the antibody or antibodies and the proteins present in the cells of the specimen;

the determination by any suitable means of the immunological complexes possibly formed, to detect the presence of a product corresponding to the fusion gene resulting from the translocation t(12;22).

Kits for implementing these methods can advantageously be prepared. These kits, in the case of a method by hybridization, contain probes according to the invention as well as control specimens of DNA or RNA. In the case of a method by reverse transcription and PCR, they contain the appropriate oligonucleotides for implementing each of these techniques as well as control specimens of DNA or RNA; in the case of an immunological method, they contain the monoclonal antibodies as well as control specimens of known reactivity.

The invention also relates to the use of DNA sequences of the invention, corresponding to a translocation t(12;22), to prepare anti-sense nucleotides, or analogs, having an anti-tumor activity, which by hybridization with all or part of the fusion gene inhibit its transcription and thus prevent the production of mRNA and chimera proteins and/or in another embodiment, they hybridize with the transcription mRNA and thus inhibit the production of chimera proteins.

Consequently, the invention relates to the use of a nucleic acid or an analog of this nucleic acid, capable of hybridizing with the nucleotide sequence of a hybrid DNA of the invention, corresponding to a translocation t(12;22), for preparing a therapeutic agent that inhibits the expression of a fusion gene resulting from a chromosomal translocation t(21;22)(q134;q12), in tumor cells of patients suffering from STMM.

Accordingly, the subject of the invention is also a therapeutic agent for inhibiting the expression of a fusion gene resulting from a chromosomal translocation t(12;22)(q13;q12), in tumor cells of patients suffering from STMM, characterized in that it is essentially constituted by a hybrid DNA of the invention, corresponding to a translocation t(12;22), or an analog of this DNA, capable of hybridizing with the nucleotide sequence of a fusion gene resulting from the chromosomal translocation t(12;22)(q13;q12).

In another embodiment, the invention relates to the use of a nucleic acid or an analog of this nucleic acid, capable of hybridizing with the nucleotide sequence of a hybrid RNA of the invention, for preparing a therapeutic agent that inhibits the translation of chimera proteins resulting from a chromosomal translocation t(12;22)(q13;q12), in tumor cells of patients suffering from STMM.

Hence, the subject of the invention is also a therapeutic agent for inhibiting the translation of chimera proteins resulting from a chromosomal translocation t(12;22)(q13;q12), in tumor cells of patients suffering from STMM, characterized in that it is essentially constituted by a hybrid RNA of the invention, corresponding to a translocation t(12;22), or an analog of this RNA, capable of hybridizing with the nucleotide sequence of the RNA originating in a fusion gene resulting from the chromosomal translocation t(12;22)(q13;q12).

The invention also relates to the nucleic acid corresponding to the Ews gene and to the mRNA which originates from it and the cDNA that derives from it, as well as the protein for which it codes. In effect, the preparation of probes and primers constitute tools that enable the detection of the normal Ews gene; this detection of the normal Ews gene can advantageously be combined with the methods of detecting the fusion genes resulting from the various translocations in which this gene is involved, so as to serve as a positive control.

The DNAs of the invention may be introduced into expression vectors derived from plasmids or virus, with the object in particular of producing the proteins corresponding to these DNA sequences so as to prepare specific antibodies of these proteins or to have pharmacological study models available.

Further characteristics of the invention will become apparent from the ensuing description in conjunction with examples, it being understood that these examples do not in any way represent a limitation in the scope of the claims.

EXAMPLE 1

STUDY OF THE RECURRENT CHROMOSOMAL TRANSLOCATION t(11;22) ASSOCIATED WITH EWING'S SARCOMA

I—Cloning of Breakpoints

Using a panel of hybrid somatic cells, it has been demonstrated that the locus identified with the VIIIF2 probe and that coding for the leukemia inhibition factor (LIF) are on each side and in proximity with the breakpoint of chromosome 22 (O. Delattre, C. J. Azambuja, A. Aurias et al., Genomics 9, 721–727 (1991)). On the scale defined by Trask et al. (B. Trask, D. Pinkel, G. Van Den Engh, Genomics 5, 710–717 (1989)), the distance between these two loci has been estimated by fluorescence in situ hybridization (FISH) at interphase nucleii between 1.5 and 2 megabases.

Differential screening of a bank of specific cosmids of chromosome 22 with various Alu-PCR products (D. L. Nelson, S. A. Ledbetter, L. Corbo, M. F. Victoria, R. Ramirez-Solis, T. D. Webster, D. H. Ledbetter, C. T. Casky, Proc. Natl. Acad. Sci. USA 86, 6686–6690 (1989)) generated from four hybrid cells has lead to the identification of three independent loci, which are telomeric at the breakpoint and in proximity with the locus LIF (J. Zucman, O. Delattre, C. Desmaze, Genomics, in press). Two of them are disposed in a large 450 kilobase contig constructed beforehand by expansion of the LIF locus. By the bicolor FISH technique on interphase nucleii, the third locus, identified from the cosmids straddling Cos5 and Cos6 (J. Zucman, O. Delattre, C. Desmaze, Genomics, in press) has been located between the VIIIF2 and LIF loci. The Cos5/Cos6 locus has been extended progressively by recurrent isolation of straddling clones, using a bank of specific cosmids of chromosome 22.

In the course of this procedure, it has been demonstrated that two cosmids, named B6 and G9, straddle the breakpoint of chromosome 22 at the derivative 11 of the translocation t(11;22), of A3EW2-3B, and Alu6, with two hybrid cells deriving from the ES and PN tumors, respectively, and containing derivative 11 (A. H. M. Geurts van Kessel, C. Turc-Carel, A. Klein et al., Mol. Cel. Biol. 5, 427–249 (1985); F. Zhang, O. Delattre, G. Rouleau et al., Genomics 6, 174–177 (1990)).

The FISH technique with metaphase chromosomes of a PN cell line employed with one of the two cosmids confirms that the breakpoint has been crossed, because a fluorescent signal is then observed at derivative 22 of the translocation.

DNA fragments, in unique copies in the human genome, near the breakpoint of chromosome 22 have been selected to analyze the DNA of a group of 20 ES and PN tumors. In all cases, a breakpoint is observed in the same region of approximately 7 Kb, which has been called EWSR1, standing for Ewing's sarcoma region 1.

A bank of cosmids made from the ICB104 cell line deriving from a PN tumor (F. Zhang, O. Delattre, G. Rouleau et al., Genomics 6, 174–177 (1990)) has been screened with probes originating in EWSR1. Three groups of straddling cosmids were isolated, one corresponding to the normal chromosome 22 and the other two corresponding to each of the two derivatives of the translocation. Consequently fragments not originating in chromosome 22 but originating in these cosmids were used to identify a clone, of which the FISH technique demonstrated that it derived from region q24 of chromosome 11.

Comparing the restriction maps for the intact and rearranged regions of chromosomes 11 and 22 indicates, at the level of resolution allowed by the study, that the translocation is simple and reciprocal.

The locus of chromosome 11 was extended over 100 Kb by recurrent isolation of straddling cosmids. Screening the same group of twenty tumors with probes of this region has made it possible to identify 17 breakpoints on chromosome 11. They are distributed without obvious clumping in a region of more than 40 Kb, called EWSR2. Interestingly, the two tumors have a variant translocation, and both of the two that have a cytogenetically intact chromosome 11 are altered in region EWSR2; this is evidence of a submicroscopic rearrangement in these tumors.

On the molecular level, the positions of the breakpoints in the ES and PN tumors do not demonstrate obvious specificity, suggesting that they do not allow differentiation of these two very close cancers.

II—Characterization of the Genes Involved in the Translocation

The region EWSR1 is flanked by three groups of sites for a rare restriction site endonuclease. It appears in human cells that these sites are at least partially nonmethylated, which suggests that they belong to HTF islands (S. Lindsay, A. P. Bird, Nature 327, 336–338 (1987)).

As has been demonstrated by cross hybridization with mouse DNA and hamster DNA, the region EWSR1 is included in a phylogenetically preserved region. Fragments were selected for Northern blot screening, prepared from RNA extracted from 7 PNET tumors exhibiting a translocation t(11;22), three non-karyotyped ES tumors, and several normal tissues (lung, heart, liver, pancreas, placenta, kidney, skeletal muscle) and four control or cell line tumors (neuroblastoma, pheochromocytoma, edinocarcinoma of the colon, HeLa).

A restriction fragment EcoRl of 3 Kb, named 22RR3, which is centromeric in region EWSR1, in all specimens detects a 2.5 Kb transcript, and in the 10 PNETs tested it detects one other specific transcript of variable size.

The same 2.5 Kb transcript, but not the specific transcripts of the PNET tumors, is observed with a telomeric probe of region EWSR1 (probe 22RR12). Conversely, a probe distal from the region EWSR2 of chromosome 11 (prbbe 11RR1) gives the opposite result, by detecting the specific transcript of PNET tumors and not the 2.5 Kb transcript. These results strongly suggest the presence in the PNET tumors tested of a chimera RNA that fuses together the sequences coded by chromosome 22 and chromosome 11. Moreover, the probe 11RR1 demonstrates a transcript in the messenger RNAs of lung, heart, and liver tissues, which is not observed in the other normal tissues tested.

Probes named 22R3 and 22R12 were used to screen a bank of human cDNA, and the straddling clones that hybridize with the two probes have been characterized. The largest clone contains 1968 pd, whose open reading phase includes a first codon ATG which is present in the context of a Kozak consensus sequence; it codes a protein of 656 amino acids, named EWS. A search of the data bases (NBRF and Swissprot) has revealed that the sequence of 285 first amino acids has a homology with proteins such as gluten, gliadin, chorionic protein S36, annexine VII, and the ordeines B1 and C.

Nevertheless, the greatest homologies have been observed with the C-terminal domain of the large subunit of the II-eukaryotic polymerase RNAs (CTD-polII).

The various molecules contain a domain that includes the repetition of a peptide of seven amino acid residues including tyrosine and major proportions of proline and serine. This domain may take on a secondary structure named in particular pro-β (N. Matsushima, C. E. Creutz, R. H. Kretsinger, Proteins 7, 125–155 (1990)).

The C-terminal portion of the protein EWS contains three regions (300 to 340, 454–513, 559–640) rich in glycine (46%), arginine (19%) and proline (13%), which has homologies with proteins rich in glycines, such as collagen, keratin and the proteins that link the single-strand nucleic acids.

A sequence of 85 amino acids disposed between the first and second regions is homologous with a sequence encountered in several proteins that link RNA. This domain contains the RNP-1 and RNP-2 consensus sequences (R. J. Bandziulis, M. S. Swanson, G. Dreyfuss, Genes Dev. 3, 431–437 (1989)) and has been demonstrated as the RNA recognition pattern for the protein snRNP U1 at 70 Kd (C. C. Query, R. C. Bentley, J. D. Keene, Cell 57, 89–101 (1989)). In this region, other marks of similar homologies have been found with several proteins that link RNA and have been functionally characterized. Nevertheless, the highest rate of homology has been obtained with the product of translation of the cDNA of the Drosophila clone pen p19, which does not have a known function and contains elements of the PEN type that are repeated (S. R. Haynes, M. L. Rebbert, B. A. Mozer, F. Forquignon, I. B. Dawid, Proc. Natl. Acad. Sci. USA 84, 1819–1823 (1987)).

The probe called 11RR1 has been used to retrieve 11 straddling clones that originate in a human marrow cDNA bank. The longest clone, named BM025, with a 2939 pb insert, contains a 1356 pb open reading phase.

Analyzing this sequence of deduced amino acids reveals a homology with members of the family of Ets genes. For the human gene Ets-1, this homology is close to 33% in the transcription activation domain (A. Gutman, C. Wasylyk, Trends Genet. 7, 49–54 (1991)) and reaches 70% for the DNA fixation domain (F. D. Karim, L. D. Urness, C. S. Thummel, et al, Genes Dev. 4, 1451–1453 (1990)).

The most striking homology has been demonstrated with the mouse gene Fli-1, for which the amino acid identity reaches 97% (Y. Ben-David, E. B. Giddens, K. Letwin, A. Bernstein, Genes Dev. 5, 908–918 (1991)).

III—Characterization of Chimera mRNA Coding for the Hybrid Proteins

The hybridization of the 5' ends of the two cDNAs on the contigs of chromosomes 11 and 22 has shown that the two genes are transcribed in the direction from the centromere to the telomere.

The fusion transcript demonstrated by Northern blot is initiated at chromosome 22 and terminated at chromosome 11. In order to study the junction of the two genes, the inventors have looked for the exons that centromerically flank the region EWSR1 and telomerically flank the region EWRS2. Two genome fragments named 22HP.5 and 11RR1, which hybridize respectively with the cDNAs coding for the EWS and HUM-FLI-1 proteins have been sequenced and have revealed the presence of an exon in each case.

Oligonucleotides homologous with these exons have been used to perform reverse transcription amplified by PCR of the RNAs originating in the various sources.

Except for the RNAs originating in tissues from the breast, neuroblastoma (IMR32), pheochromocytoma, lymphoma, and ovarian carcinoma, all the RNAs originating from the seven PNET tumors with a translocation t(11;22) and those originating in the three non-karyotyped ES tumors enable the amplification of a specific product. Depending on the tumor, three different sizes of amplification products have been observed within a first period of time. Their sequences reveal three types of fusion transcripts.

The first type contains exon sequences present in the fragments 22HP.5 and 11RR1 and a 174 bp sequence originating in the adjacent exon that is most centromeric in the Hum-Fli-1 gene.

The second and third types differ from the first in the presence at the level of the junction site of additional sequences originating respectively in the region that codes the Ews and Hum-Fli-1 genes. In all cases, the fusion is in phase, and the resultant chimera proteins differ from the protein EWS by the substitution, for the RNA fixation domain, of the DNA fixation domain of the HUM-FLI-1 protein homologous to the domain of the protein ETS. A similar study made on approximately 40 ES and PN tumors have made it possible to demonstrate other types of fusion genes resulting from the chromosomal translocation t(11;22).

IV—Discussion

The protein EWS, through its total sequence, shares homologies with known proteins to interact with single-strand nucleic acids, and more particularly with RNA.

First, the C-terminal region contains an RNA recognition pattern which is also encountered in a group of proteins that participates in the post-transcriptional process of RNA (A. D. Frankel, I. W. Mattaj, D. C. Rio, Cell 67, 1041–1046 (1991)). Furthermore, in the protein EWS this pattern is flanked by sequences of amino acids rich in glycene. Such sequences, obtained in various RNA fixation proteins, also interact with RNA (A. Kumar, J. R. Casas-Finet, C. J. Luneau, et al, J. Biol. Chem. 265, 17094–17100 (1990); S. H. Munroe, X. Dong, Proc. Natl. Acad. Sci. USA 89, 895–899 (1992)).

Second, the N-terminal region of the protein EWS has homology with the region CTD-pol II. It has been suggested that this domain interacts with transcription factors at the level of the initiation complex (J. L. Corden, TIBS 15, 383–387 (1990)).

These homologies of the EWS protein suggest that it has two different functional domains that together participate in the mechanism of gene expression.

The family of genes Ets is involved through various mechanisms in the erythroleukemias induced in the mouse and in chickens by retroviruses. The first member of this family has been discovered to be a co-transduced element that gives rise to hybrid proteins containing MYB and ETS-1 (D. K. Watson, R. Ascione, T. S. Papas, Crit. Rev. Oncogenesis 1, 409–436 (1990)).

Independently, two other members of this family, Spi-1 (PUI) and Fli-1, are activated by the retroviral integration of the various strains of the Friend leukemia virus (Y. Ben-David, A. Bernstein, Cell 66, 831–834 (1991)). All the members of this family of proteins have a highly preserved region, called the ETS domain (F. D. Karim, L. D. Urness, C. S. Thummel, et al. Genes Dev. 4, 1451–1453 (1990)), of which it has been demonstrated in the majority of cases that it is fixed specifically to the elements of the promoter region that are rich in purine, and promotes the transcriptional activation of various viral or eukaryotic cell genes (A. Gutman, C. Wasylyk, Trends Genet.7, 49–54 (1991); F. Lim, N. Kraut, J. Frampton, T. Graf, EMBO J. 11, 643–652 (1992); R. A. Hipskind, V. N. Rao, C. G. F. Mueller, et al, Nature 354, 531–534, (1991)).

Furthermore, toward the N-terminal, the proteins ETS-1 and ETS-2 contain a region that promotes transcription when it is linked with the DNA fixation domain of LexA (B. Wasylyk, A.Gutman, P. Flores, A. Begue, D. LePrince, D. Stehelin, Nature 346, 191–193 (1990)), or Gal4 (S. Seneca, B. Punyammalee, N. Bailly, et al., Oncogene 6, 357–360 (1991)).

The strongest homology relating to the product of translation of Hum-Fli-1 appears with the murine protein FLI-1 (Y. Ben-David, E. B. Giddens, K. Letwin, A. Bernstein, Genes Dev. 5, 908–918 (1991)), a protein for which the homologies with the DNA fixation and ETS-1 transcription activation domains can be clearly identified.

It has been demonstrated that the retroviral insertion site that activates the murine gene Fli-1 is located near the gene Ets-1 on chromosome 9 in the mouse. The insertion site is phylogenetically preserved and is homologous with a region of human chromosome 11 near the gene Ets-1 (V. Baud, M. Lipinski, E. Rassart, L. Poliquin, D. Bergeron, Genomics 11, 223–224 (1991)). On the basis of both this homology and this syntenic preservation, it is proposed that Hum-Fli-1 represents the cDNA of the human gene homologue to the murine gene Fli-1.

Cloning the chromatically acquired recurrent chromosomal translocation breakpoints has illuminated two major mechanisms of cancerization: deregulation of the expression of a gene, and generation of fusion proteins (E. Solomon, J. Borrow, A. D. Goddard, Science 254, 1153–1160 (1991)).

The translocation described in the discussion of the invention is clearly geared to the fusion of two genes which belong to families until now not implicated in human carcinogenesis: the family ETS of proteins that fixed to DNA, and the family of proteins affixed to RNA. Because the translocation is recriprocal, without apparent loss of genetic material, at each of the two derivative chromosomes, the end 5' of the gene is juxtaposed with the 3' end of the other gene.

The chimera gene generated on the derivative (11) is not expressed at a sufficient level to be measured by northern blot and does not seem to be involved in the tumoral phenotype, since the derivative (11) can occasionally be lost in ES tumors (C. Turc-Carel, I. Philip, M. P. Berger, T. Philip, G. M. Lenoir, Cancer Genet. Cytogenet. 12, 1–19 (1984); E. C. Douglass, M. Valentine, A. A. Green, F. A. Hayes, E. I. Thompson, J. N. C. I. 77, 1211–1213 (1986)). Conversely, the transcript hybrid generated by derivative (22) is visible by northern blot even though its intracellular level appears to decrease in comparison with the normal transcript of the gene Ews coated by chromosome 22. This difference could be due to an instability by a long non-coating AT-rich 3' sequence (G. Brawerman, Cell 57, 9–10 (1989)), like that encountered in the Hum-Fli-1 transcript.

The translocation t(11-22) has two direct consequences:

First, it puts the expression of the DNA fixation domain, that is, Hum-Fli-1, under the control of an ectopic promoter, which is the Ews promoter, of which northern blot hybridization has demonstrated that it does not share the tissue specificity of the promoter Hum-Fli-1.

Second, the translocation substitutes the DNA succession domain, Hum-Fli-1, for an RNA succession domain and connects it by the same polypeptide chain to a domain that has homology with CTD-polII.

The constant involvement of the 22q12 band and more precisely the region EWSR1 in ES and PN tumors indicates that this latter domain plays an essential role in the process of cancerization. The structure of the chimera protein indicates that this role is probably played out by way of alteration of the regulation of transcription of target genes, Hum-Fli-1.

By analogy with the mode of action of CTD-polII (C. L. Peterson, W. Krugen, I. Herskowitz, Cell 64,1135–1143 (1991)), the chimera protein can functionally impede the negative regulation elements that control transcription. One possible example of such alteration could be the antigen MIC2, which is specifically over-expressed in PNET tumors that have a translocation t(11;22) (I. M. Ambros, P. F. Ambros, S. Strehl, et al., Cancer 67, 1886–1893 (1991); P. Garin-Chesa, E. J. Fellinger, A. G. Huvos, et al., Am. J. Pathol.139, 275–286 (1991)).

The implication in a solid tumor of a gene of the Ets type indicates that the role of the family of proteins ETS in the cancerization process is not limited to hematologic cancers. In the case of erythroleukemias, in which this family is implicated, a highly transformed phenotype is associated with other alterations, intervening either by co-transduction of Myb sequences or by an alteration of the gene TP53 (Y. Ben-David,a. Bernstein, Cell 66, 831–834 (1991)).

In the case of Ewing's Sarcoma, besides the translocation t(11;22), other recurrent chromosomal aberrations including a non-compensated translocation t(1q16p) have been described (E. C. Douglass, M. Valentine, A. A. Green, F. A. Hayes, E. I. Thompson, J. N. C. I.77, 1211–1213 (1986); F. Mugneret, S. Lizard, A. Aurias, C. Turc-Carel, Cancer Genet. Cytogenet.30, 239–245 (1988)). Their contribution to the tumoral phenotype has yet to be evaluated.

Analyses of karyotypes demonstrating the presence of a translocation t(11;22) in small cell tumors have been used for several years as a diagnostic criterion of ES and PN tumors. Two new approaches for diagnosis are now available:

The first is based on the fact that the small size of the region EWSR1 allows simple detection of genomic rearrangements by the southern blot technique;

The second is based on reverse transcription and gene amplification by PCR and furnishes a sensitive method for demonstrating the presence of fusion transcripts in tumors and in their potential sites of metastasis.

It is currently possible to obtain indications as to the frequency and specificity of the Ews and Hum-Fli-1 alterations in human tumors, and more particularly in those exhibiting cytogenetic aberrations 22q12 and/or 11q24 (J. Whang-Peng, C. E. Freter, T. Knutsen, J. J. Nanfro, A. Gazdar, Cancer Genet. Cytogenet. 29, 155–157 (1987); J. D. Chadarevian, M. Vekemans, T. A. Seemayer, N. Eng. J. Med. 311, 1702–1703 (1984); A. O. Cavazzana, S. Navarro, N. Noguera, et al., Adv. Neuroblastoma Res. 2, 463–473 (1988); N. V. Vigfusson, L. J. Allen, J. H. Philip, T. Alschibaja, W. G. Riches, Cancer Genet. Cytigenet. 22, 211–218 (1986); A. Aurias, C. Rimbaut, C. Buffe, J. Dubousset, A, Mazabraud, N. Eng. J. Med. 309, 496–497 (1983); C. Turc-Carel, I. Philip, M. P. Berger, T. Philip, G. M. Lenoir, N. Eng. J. Med. 309, 497–498 (1983); J. Whang Peng, T. J. Triche, T. Knutsen, J. Miser, E. C. Douglass, M. A. Israel, N. Eng. J. Med. 311, 584–585 (1984); C. Turc-Carel, A. Aurias, F. Mugneret, et al., Cancer Genet. Cytogenet.32, 229–230 (1988); C. Turc-Carel, P. Dal Cin, U. Rao, C. Karakousis, A. Sandberg, Cancer Genet. Cytogenet. 30, 145–150 (1988); W. P. V. Shen, R. F. Young, B. N. Walter, B. H. Choi, M. J. Smith, J. Katz, Cancer Genet. Cytogenet. 45, 207–217 (1990); J. M. Trent, Y. Kaneko, F. Mitelman, Cytogenet. Cell Genet. 51, 533–562 (1989)).

The hypothesis of a relationship between Ews and a hereditary genetic defect responsible for type II neurofibromatosis, which has been localized in the same region 22q12 (G. A. Rouleau, B. R. Seizinger, W. Wertelecki, et al., Am. J. Hum. Genet. 46, 323–328 (1990)) can also be examined.

V. Description of These Figures

FIG. 1

1) Results

FIG. 1 shows the map of the region EWSR1 on chromosome 22.

at A, a part of the contig resulting from the expansion of the Cos5/Cos6 locus identified by differential Alu-PCR hybridization is schematically shown (J. Zucman, O. Delattre, C. Desmaze, C. Azambuja, G. Rouleau, P. DeJong, A. Aurias, G. Thomas, Genomics, in press).

The position of the contig is indicated with respect to other different nearby loci. The cosmids B6 and G9 cover the breakpoints of A3EW2-3B and ALU 6, two hybrid somatic cells that contain the derivative (11) of ES and PN tumors, respectively (A. H. M Geurts van Kessel, C. Turc-Carel, A. Klein et al., Mol. Cel. Biol. 5, 427–429 (1984); F. Zhang, O. Delattre, G. Rouleau et al., Genomics 6, 174–177 (1990)).

Shown at B is the restriction map EcoR1 of a 100 Kb fragment centered around the region EWSR1. The position of three dinucleotide regions CpG is shown: CpG1 contains three sites SacII, three sites BssHII, and one site MluI; CpG2A contains three sites SacII, three sites BssHII; CpG2B contains three sites BssH2, three sites SacII, and one site NotIU.

Shown at C is a detailed restriction map of the region EWSR1 on which the sites PstI are marked (P), the sites BamHI are marked (B), the sites XbaI are marked (X), and the sites EcoRI are marked (R). The vertical arrows indicate the rearranged restriction fragments in each of the 20 tumors tested.

2) Method a) A specific bank of chromosome 22, LL22NC01 constructed from the Lawrist 5 cosmid vector was used to illustrate what was learned about chromosome 22. The terminal fragments where the entire insert have been marked by random priming, using a dCTP marked at a by $^{32}$P. The repetitive human sequences and the residual contaminant vectors have been inhibited with a large excess of total human DNA and DNA vectors.

The preincubated probe was then used to screen the bank, by standard procedures, and the straddling tosmids were identified.

b) The tumor specimens were recovered immediately after surgery.

A fragment was used for karyotype analysis:

tumors T2 to T11 have a typical translocation t(11;22) (q24;q12);

tumor T12 has a complex translocation t(10;11;22;12) (q22;q24;q12;q24);

tumor T13 has a translocation variant t(14;22)(q32;q12);

tumor T14 has a translocation variant t(7;22)(q35;q12);

tumor T15 has a complex translocation t(11;11;22) (q13;q24;q12).

Karyotype analysis of tumors 16 through 19 was not done, and tumor T20 has only normal metaphases. Bicolor FISH analysis on interphase nucleii of tumors T17 and T19 shows the appearance of a breakpoint in band 22q12 (C. Desmaze, J. Zucman, O. Delattre, G. Thomas, A. Aurias, Genes Chr. Cancer, in press).

Tumor T1 corresponds to the hybrid cell line A3EW2. The hybrid cell line Alu6 originates from tumor T8. Tumors T7-T13 are PN tumors; all the other tumors were diagnosed as Ewing's sarcoma. The DNA of blood specimens (N) and tumor specimens (T) was digested with the enzyme PstI and analyzed by the Southern blot method with the 5.5-sac probe.

FIG. 2

This Figure shows the detection of rearranged bands in the tumors; more particularly, the detection of abnormal genome fragments in six tumors. The number of the tumor is shown at the top of the bands. The DNA specimens taken from the blood of patients carrying tumors T16 and T18 are indicated by (N). In each case, the fragment corresponding to the rearranged junction is indicated by a horizontal arrow.

FIG. 3

1) Results

Figure 3:
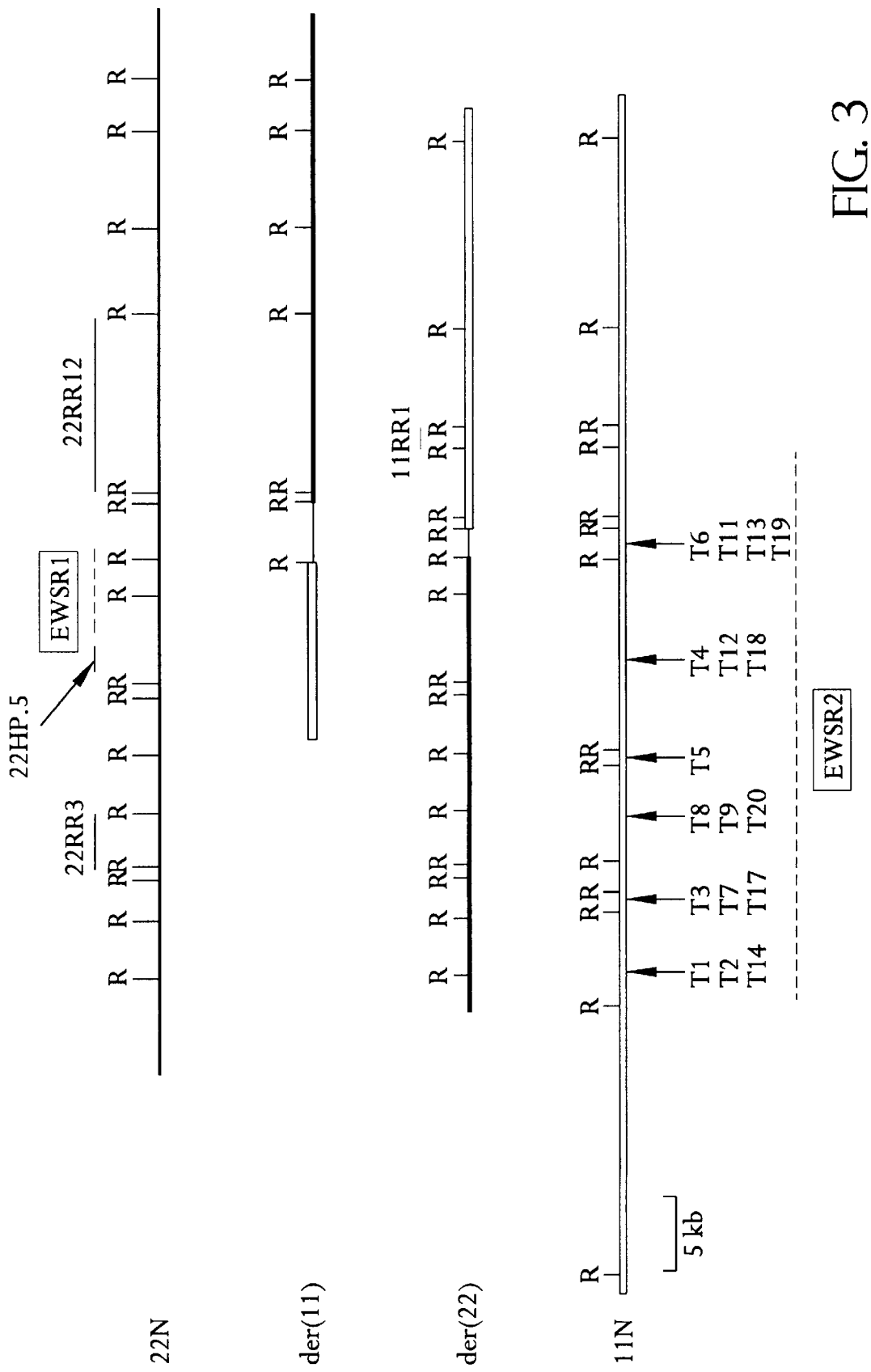
FIG. 3 shows a restriction map of the regions involved in the chromosomal translocation t(11;22) (q23;q12) and two derivatives of the translocation.
Figure 4:
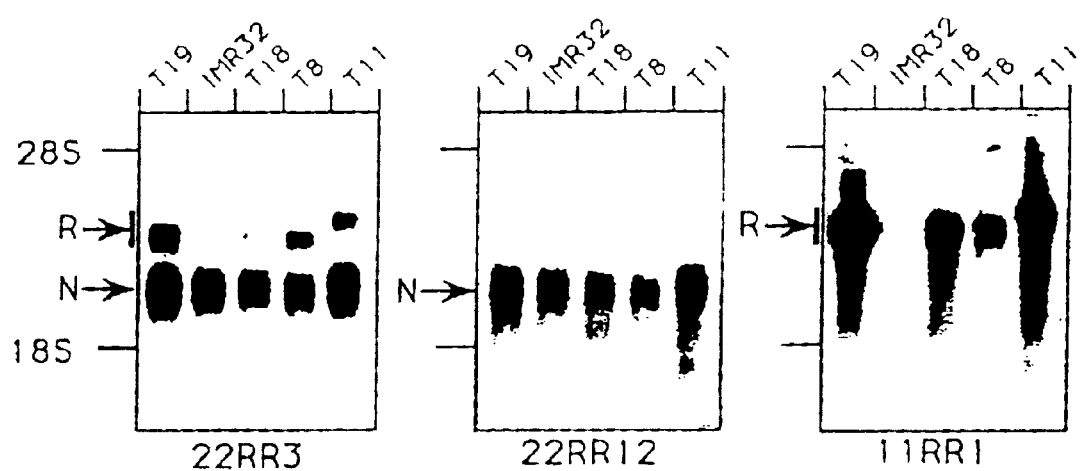
FIG. 4 shows northern blot detection of abnormal transcripts in Ewing's sarcoma or cell lines.
Figure 5:
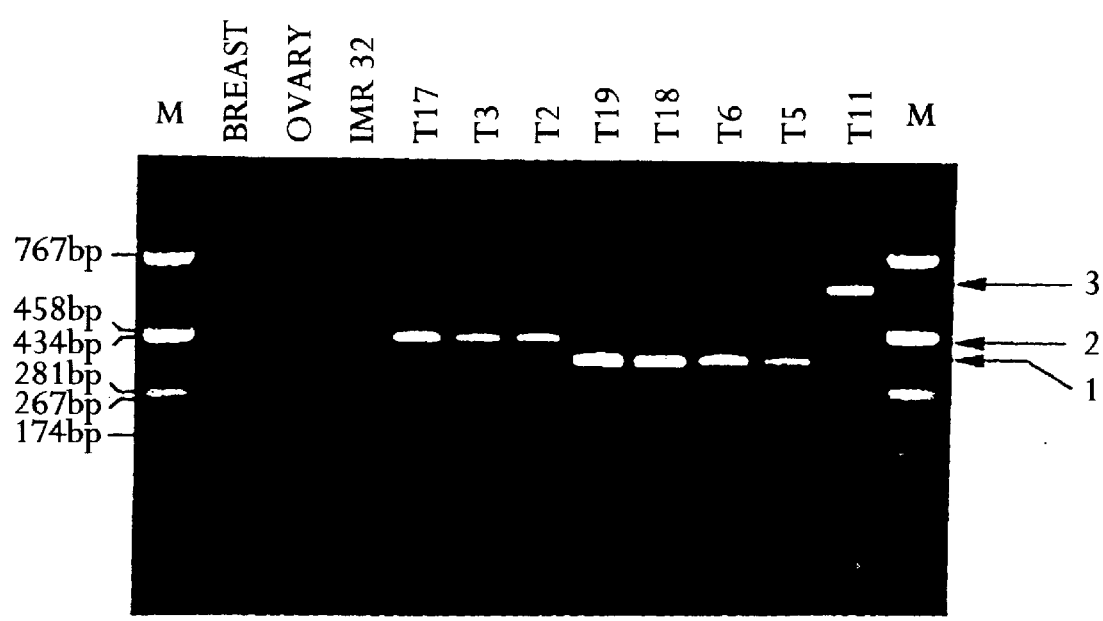
FIG. 5 shows reverse transcription and PCR detection of three types of chimeric transcripts.

FIG. 3 shows the restriction map of the regions involved in the chromosomal translocation t(11;22)(q23;q12); the normal regions (22n) and (11n) and the two derivatives 11 and 22 of the translocation t(1;22), der(11) and der(22), are shown for the tumor T11.

The double line represents chromosome 11; the heavy line represents chromosome 22.

In the derivatives der(11) and der(22), the single line between the parts-of chromosomes 11 and 22 represents the fusion fragment EcoR1. EWSR1 and EWSR2 represent the smallest region that contains all the break points identified in chromosome 22 and chromosome 11, respectively. The vertical arrows indicate the position of the rearranged fragments EcoR1 identified in 17 tumors.

The abbreviations designating the tumors are identical to those used for FIG. 1.

Finally, the positions of the probes 22RR3, 22RR13, 22HP.5 and 11RR1 are indicated.

2) Methods

A linker XhoI was inserted at the level of the site BamHI of a SuperCos vector sold by Stratagene. The 3' end of the DNA, partially digested by MboI of a cell line ICB 104 derived from tumor T11 (F. Zhang, O. Delattre, G. Rouleau et al., Genomics 6, 174–177 (1990)), was partially filled with dGTP and dATP. The high molecular weight fragments were purified on gel and linked to the site XhoI of the modified SuperCos vector and partially with dTTP and dCTP. After conditioning with the Gigapack Gold kit sold by Stratagene, the virions were used to infect the E. coli strain DH5 alpha MCR.

The bank obtained of $4 \times 10^5$ independent cosmids was screened with the probes 22RR3 and 22RR12. The groups of straddling clones containing either a nonaltered region EWSR1 (22N) or the junction fragment of the derivative 22 of the translocation, that is der(22), or derivative 11 of the translocation, der(11), were identified. The probe 11RR1 made it possible to retrieve a cosmid, which by fluorescent in situ hybridization on chromosome is demonstrated to originate in band 11q24. This cosmid was used to extend the locus to the normal chromosome 11.

FIG. 4

This Figure shows the northern blot detection of abnormal transcripts in Ewing's sarcoma or cell liens.

The same northern blot containing 1 μg of polyadenylated mRNA originating in tumors T19, T11, T8 and T18, or the neuroblastoma line IMR32, were successively hybridized with the probes 22RR3, 22RR12 and 11RR1. N represents the normal transcript of the gene Ews; R represents the fusion transcripts.

Depending on the tumor, the sizes of the abnormal transcripts differ substantially. The same abnormal transcripts are detected both with the probe 22RR3 and with the probe 11RR1, which indicates that the translocation gives rise to the synthesis of a chimera transcript.

FIG. 5

1) Results

This Figure represents the reverse transcription and PCR detection of three types of chimera transcripts.

M is a size marker. BREAST corresponds to a breast tissue; OVARY corresponds to an ovarian carcinoma; IMR32 corresponds to a neuroblastoma cell line. The abbreviations designating the patients are identical to those of FIG. 1.

Figures 9A, 9B:
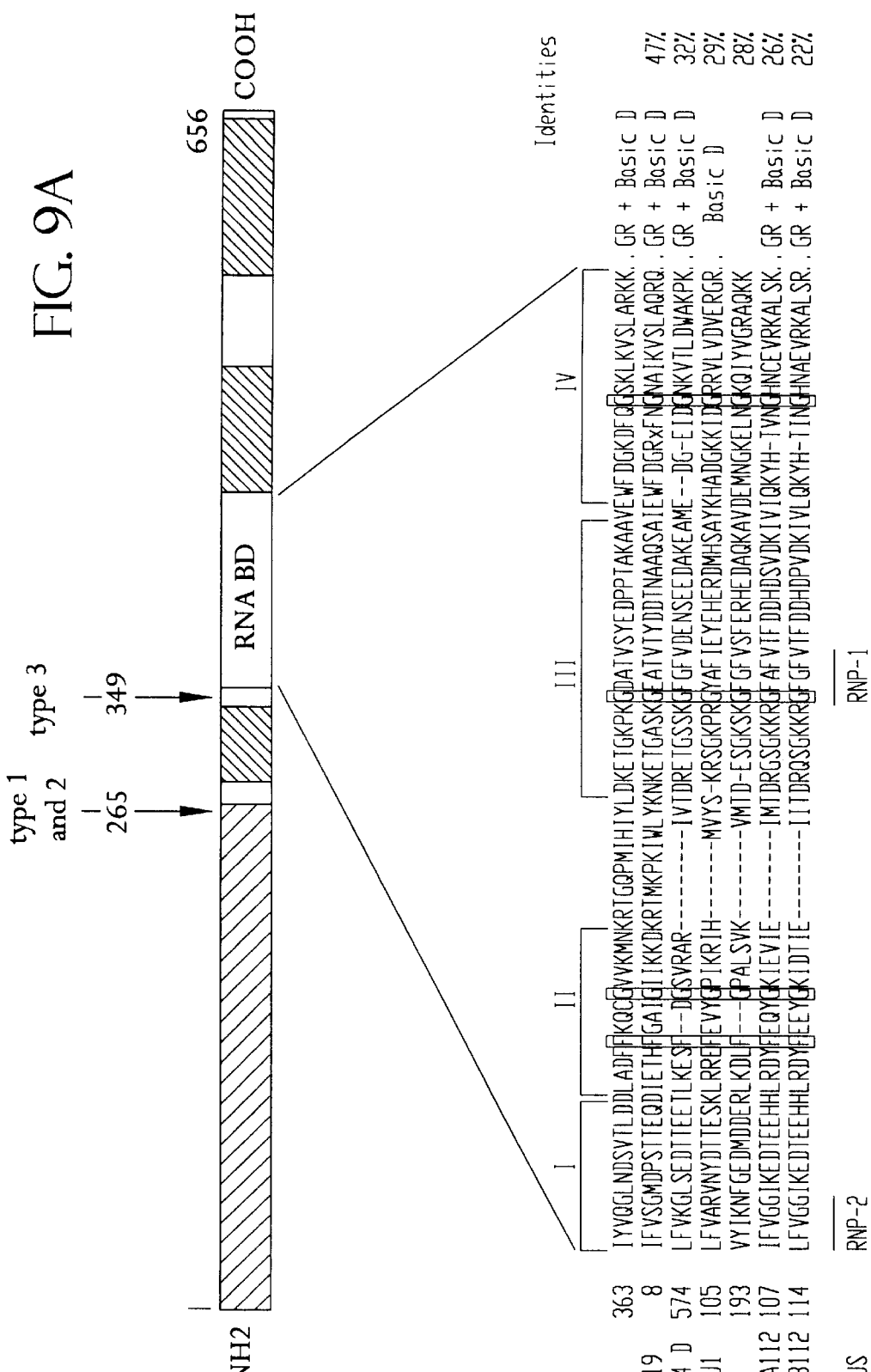
FIG. 9A shows the various domains of the protein encoded by the Ews gene.
FIG. 9B shows the most significant alignments of the protein EWS, including EWS (SEQ ID NO:7), Dpen P19 (SEQ ID NO:8), H nucl#4 (SEQ ID NO:9), HsnRNP U1 (SEQ ID NO:10), HPABP#3 (SEQ ID NO:11), HhnRNP A1#2 (SEQ ID NO:12), and HhnRNP B1#2 (SEQ ID NO:13).
Figure 10:
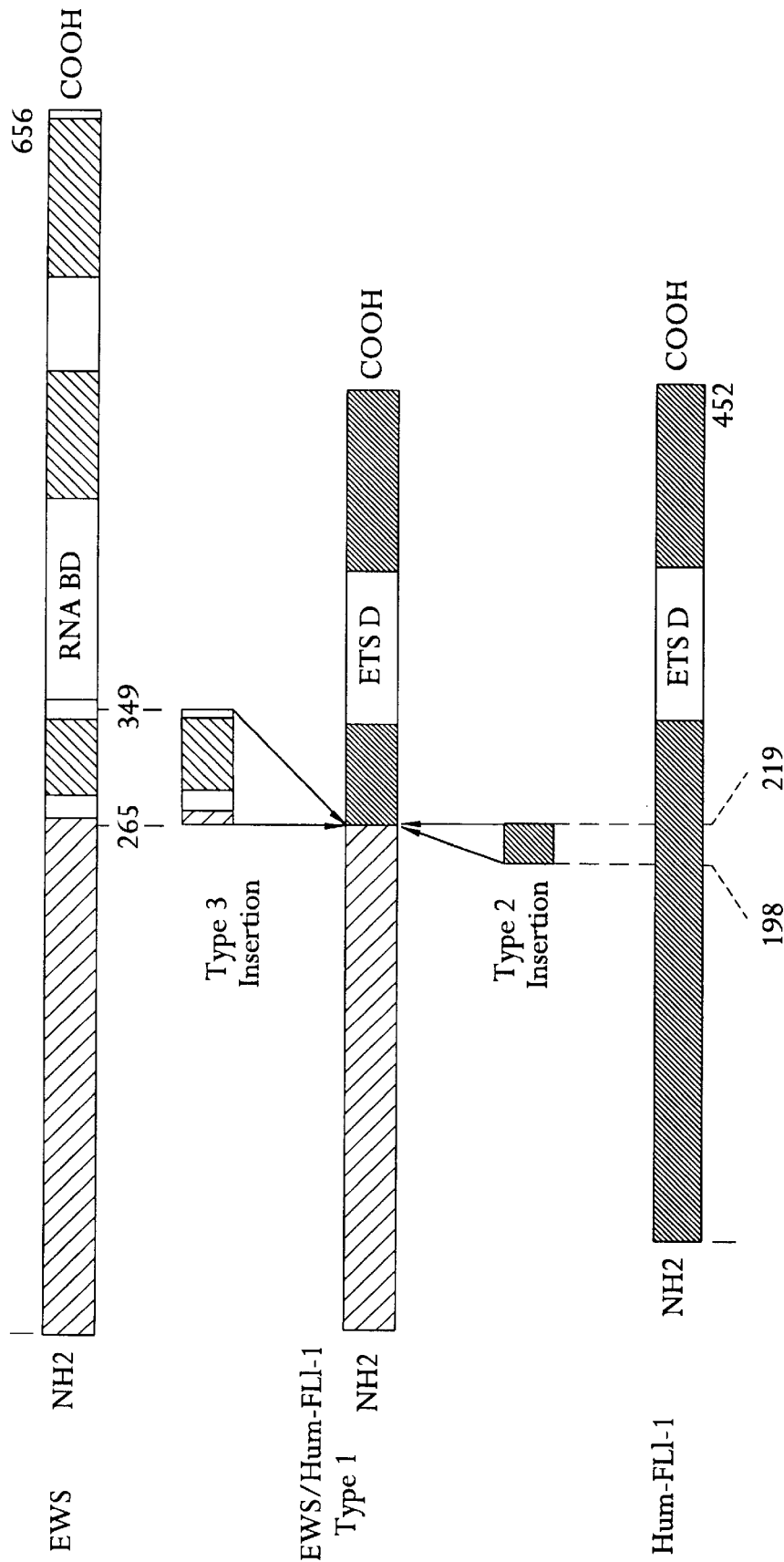
FIG. 10 shows a schematic representation of the proteins encoded by the Ews gene and the Hum-Fli-1 gene and a fusion gene of Ews and Hum-Fli-1.

The three types of transcripts described in FIG. 9 hereinafter are indicated 1, 2, 3 by an arrow.

2) Method

The oligonucleotide 11A of the following formula:

5' AGAAGGGTACTTGTACATGG 3' was used as a primer for the reverse transcription of 1 μg of total RNA, using a PCR kit Gen Amp RNA made by Cetus. The resultant cDNA was subject to 30 cycles of PCR amplification with the primers 11.3 and 22.3, of the following respective formulas:

5' ACTCCCCGTTGGTCCCCTCC 3'

5' TCCTACAGCCAAGCTCCAAGTC 3'.

Each cycle included a step of denaturation at 90° C. for 30 seconds, then at 65° C. for one minute, and an extension step at 72° for two minutes. The amplified fragment was identified by gel electrophoresis and revealed by ethidium bromide.

FIG. 6

1) Results

This Figure represents the nucleotide sequence of the cDNA containing the entire coding region and the nontranscripted 3' end of the gene Ews, as well as the sequence of amino acids deduced from this cDNA, codon by codon.

These sequences are numbered on the left. Two polyadenylation signals, one beginning at nucleotide 2143 and the other at nucleotide 2332, are underlined.

The first codon of methionine is localized with a purine (A) at position -3 and a guanosine (G) at position +4, which matches the Kozak consensus sequence.

2) Method

The probes 22RR3 and 22RR12 were used to screen a bank of human fetal brain cDNA (Stratagene catalog number 936206) and made it possible to identify a clone which has been named BF1AC5. The probe 11RR1 was used to screen a bank of human marrow cDNA (Clontech catalog number HL1058) and made it possible to identify a clone which has been named BM025. One million clones were placed on slides and screens in each bank. The subcloned DNA fragments in the phages M13mp18 or M13mp19 were used as matrices to determine the nucleotide sequences, using the method of dideoxy chain termination and either a modified polymerase T7 or the polymerase taq sold by Amersham. The 2372 bp and 2939 bp cDNA sequences of the clones BF1AC5 and BM025 were determined on the strands of straddling subclones, by using either the primer M13 or commercial primers. It has been demonstrated that they contain the entire coding sequence of the genes Ews and Hum-Fli-1.

Direct sequencing of the products of PCR amplification was done with a Sequenase sold by USB, after 30 cycles of asymmetrical amplification with either primer 11.3 or primer 22.3, and then purification through a centricon 100 membrane sold by Amicon.

FIG. 7

This Figure shows the cDNA of gene Hum-Fli-1.

FIG. 8

FIG. 8 shows the nucleotide sequence of the fusion cDNA obtained by reverse transcription and PCR amplification of the type 1 fusion transcript.

The homologue sequence (on the end 5') or complementary sequence (on the 3' end) to the primers used for the PCR amplification are underlined. The vertical line indicates the junction between the two genes that are present between the first and second positions of codon 265 of the gene Ews, and between the same positions of codon 219 of the gene Hum-Fli-1.

FIG. 9

This Figure shows the various domains of the protein EWS coded by the gene Ews.

Shown at A are the various peptide domains. The shaded region represents the first 270 amino acids containing a high proportion of tyrosine, glutamine, serine, threonine, glucione, alanine and proline, which together represent approximately 90% of all the residues. In this region, the majority of the tyrosines are present every 5 to 9 residues, and they define a degenerate pattern repeated 31 times. After the tyrosine, the most recurrent residues in the repetition are a serine at position −1 (50%), a glycine at position +1 (50%), and two glutamines in positions +2 and +3 (70% and 40%, respectively). This part of the molecule has a homology with CTD-polII.

The three shaded zones correspond to regions rich in glycine, arginine and proline.

The zone marked "RNA BD" represents an assumed RNA fixation domain, which is explained at B.

The arrows indicate the position of the junction point Hum-Fli-1 for the three different types of chimera proteins, as deduced by reverse transcription and PCR amplification as explained above.

Shown at B are the most significant alignments of the protein EWS in the assumed RNA fixation region. Dpen p19 for the Drosophila clone pen p19 (S. R. Haynes, M. L. Rebbert, B. A. Mozert, F. Forquignon, I. B. Dawid, Proc. Natl. Acad. Sci. USA 84, 1819–1823 (1987)); H nucl for human nucleotine (M. Srivastava, O. W. McBride, P. J. Flemming, H. B. Pollard, A. L. Burns, J. Biol. Chem. 265, 14922–14931 (1990)); HsnRNP U1 for 70 Kd human snRNP U1 (R. A. Spritz, K. Strunk, C. S. Surowy, S. O. Hoch, D. E. Barton, U. Francke, Nuclei. Acid. Res. 15, 10173–10393 (1987)); HhnRNP A1 and B1 for human hnRNP A1 (G. Biiamonti, M. Buvoli, M. T. Bassi, C. Morandi, F. Cobianchi, S. Riva, J. Mol. Biol. 207, 491–503 (1988)) and B1 (C. G. Burd, M. S. Swanson, M. Goerlach, G. Dreyfuss, Proc. Natl. Acad. Sci. 86, 9788–9792 (1989)); HPABP for human poly(A) fixation protein (T. Grange, C. Martin de sa, J. Oddos, R. Pictet, Nuc. Acids Res. 15, 4771–4787 (1987)). #2, #3 and #4 relate to various RNA fixation domains within the same protein. The invariable positions among these proteins are shaded, and the minimum substitutions between EWS and at least four of the six proteins are indicated in heavy characters.

Domains I through IV have been described by C. C. Query, R. C. Bentley, J. D. Keene, Cell 57, 89–101 (1989).

RNP-1 and RNP-2 relate to the consensus pattern commented on by R. J. Branzilius, M. S. Swanson, G. Dreyfuss, Genes Dev. 3, 431–437 (1989). To the right in FIG. 8B, under the caption "identities", the percentage of identical residues between EWS and each of the RNA fixation domains in question is indicated. Also indicated on the C-terminal side is the presence of a region rich in glycine residue (GR) and a basic domain (Basic D).

FIG. 10

This Figure schematically shows the proteins coded by the normal gene Ews (EWS), the normal gene Hum-FlI-1 (HUM-FLI-1), and their fusion genes (EWS/Hum-Fli-1 type 1, 2 and 3).

In the three types of chimera proteins, the C terminal portion of EWS containing the assumed RNA fixation domain (designated as RNA BD) is replaced with the C-terminal portion of the gene Hum-Fli-1 containing the domain ETS (designated ETS D). The type 1 chimera protein is entirely represented in the figure; the type 2 or 3 proteins may be reduced from that of type 1 by insertion of 84 or 22 additional amino acids originating in EWS or Hum-Fli-1, respectively. The positions of the interrupted codons are indicated in all cases.

FIGS. 11, 12, 13, 14, 15 and 16

Figure 11:
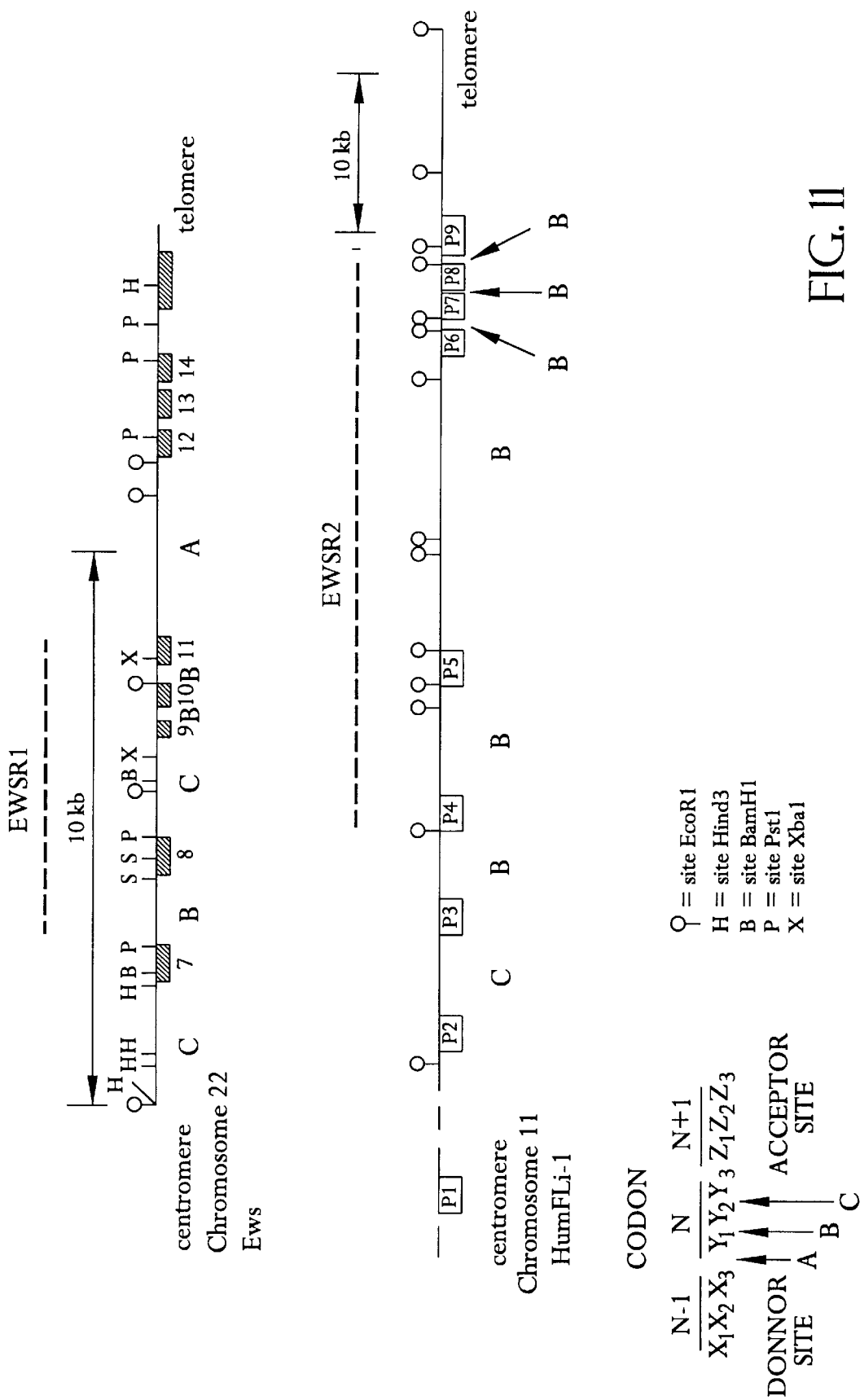
FIG. 11 shows a restriction map of the Ews and Hum-Fli-1 genes.

FIG. 11 shows the restriction map of the genes Ews and Hum-Fli-1 at the level of their break region EWSR1 and EWSR2. The position of the exons is indicated with respect to the restriction sites. The open reading frames are divided by the various exons; each intron between two coding exons interrupts the open reading frame in one of the three phases, A, B or C.

FIG. 12 represents the exon structure of the gene Ews.

It has also been possible to sequence all the intron-exon junctions for this gene, as shown in FIG. 12.

FIG. 13 shows the exon structure of the gene Hum-Fli-1.

It has also been possible to sequence the majority of the intron-exon junctions for this gene, as shown in FIG. 13.

It is accordingly possible, from this information, to contemplate the great number of possible fusion products of the two genes. A large number of fusion products that juxtapose these exons have been observed by reverse transcription and then gene amplification by PCR.

Figure 14:
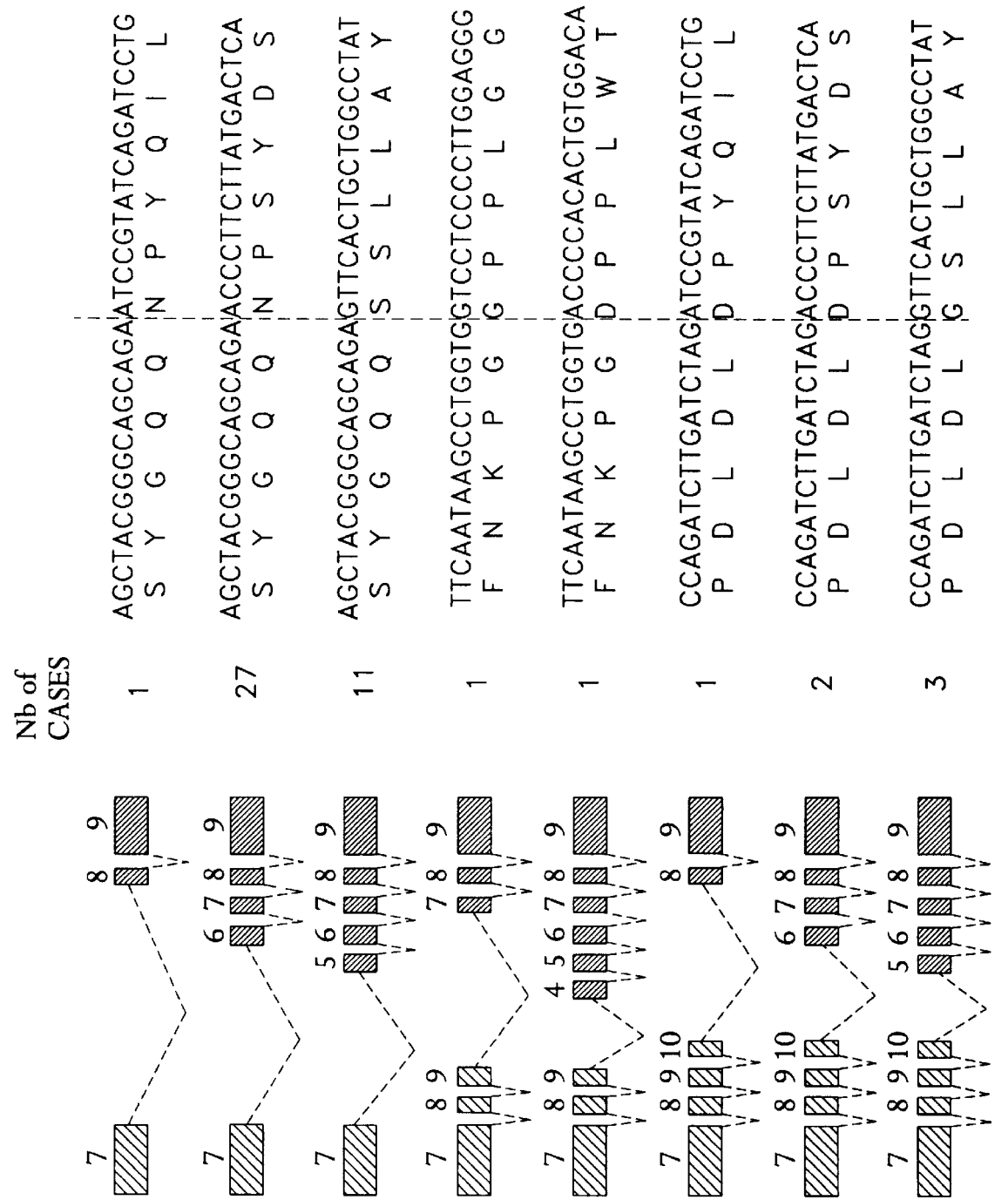
FIG. 14 shows exon juxtapositions of the Ews and Hum-Fli-1 genes and the respective junction sequences of the resultant fusion transcripts SEQ ID NO:63, SEQ ID NO:65, SEQ ID NO:67, SEQ ID NO:69, SEQ ID NO:71, SEQ ID NO:73, SEQ ID NO:75 and SEQ ID NO:77 with corresponding proteins encoded thereby SEQ ID NO:64, SEQ ID NO:66, SEQ ID NO:68, SEQ ID NO:70, SEQ ID NO:72, SEQ ID NO:74, SEQ ID NO:76 and SEQ ID NO:78.

FIG. 14 shows the exon juxtapositions of the genes Ews and Hum-Fli-1 and the junction sequences of the resultant fusion transcripts. On the left in FIG. 14, the exons of Ews (shaded boxes) and the exons of Hum-Fli-1 (solid box) involved in the juxtaposition are schematically shown; shown on the right in FIG. 14 are the junction sequences of the fusion transcripts corresponding to the juxtapositions symbolized on the left in this figure, with the number of cases observed.

Figure 15:
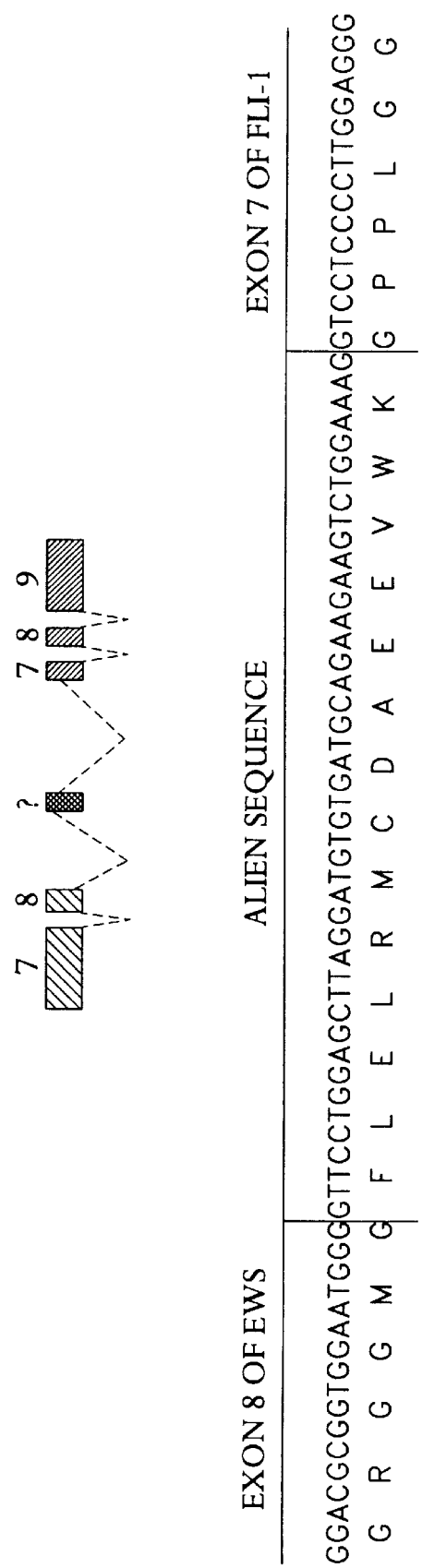
FIG. 15 shows a juxtaposition of the Ews and Hum-Fli-1 genes, between which an unknown (alien) sequence is interposed (SEQ ID NO:79 and SEQ ID NO:80).

FIG. 15, using a nomenclature identical to that of FIG. 14, shows a case of juxtaposition observed concerning exon 8 of Ews and exon 7 of Hum-Fli-1, between which an original unknown (alien) sequence is interposed.

Figure 16:
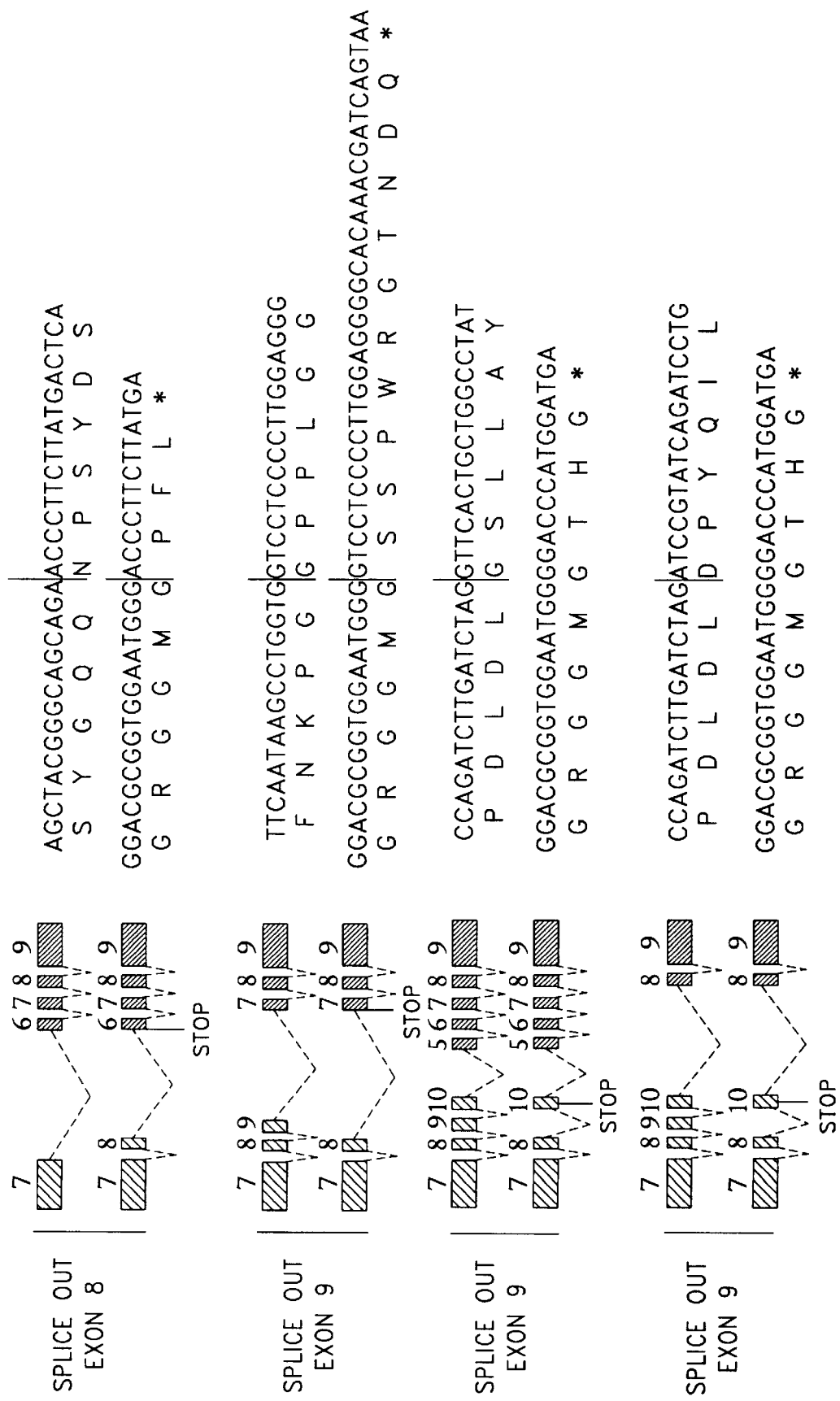
FIG. 16 shows four juxtapositions of the Ews and Hum-Fli-1 genes and the resultant junction sequences, SEQ ID NO:81/SEQ ID NO:82, SEQ ID NO:83/SEQ ID NO:84, SEQ ID NO:85/SEQ ID NO:86, SEQ ID NO:87/SEQ ID NO:88, SEQ ID NO:128/SEQ ID NO:129, SEQ ID NO:95/SEQ ID NO:96, SEQ ID NO:93/SEQ ID NO:94, and SEQ ID NO:91/SEQ ID NO:92, as respectively appear in the figure.

FIG. 16, using a nomenclature identical to that of FIGS. 14 and 15, shows four cases in which two different fusion transcripts have been observed, juxtaposing a series of exons of Ews and a series of exons of Hum-Fli-1, this being genuinely the result of alternating splices. In the fusion sequences on the right of the figure, the asterisks indicate the sequence of the product of translating a stop codon.

FIG. 17

This Figure represents the sequence of the promoter region of the gene Ews.

EXAMPLE 2

STUDY OF THE RECURRENT CHROMOSOMAL TRANSLOCATION t(21;22) ASSOCIATED WITH EWING'S SARCOMA

Figure 18:
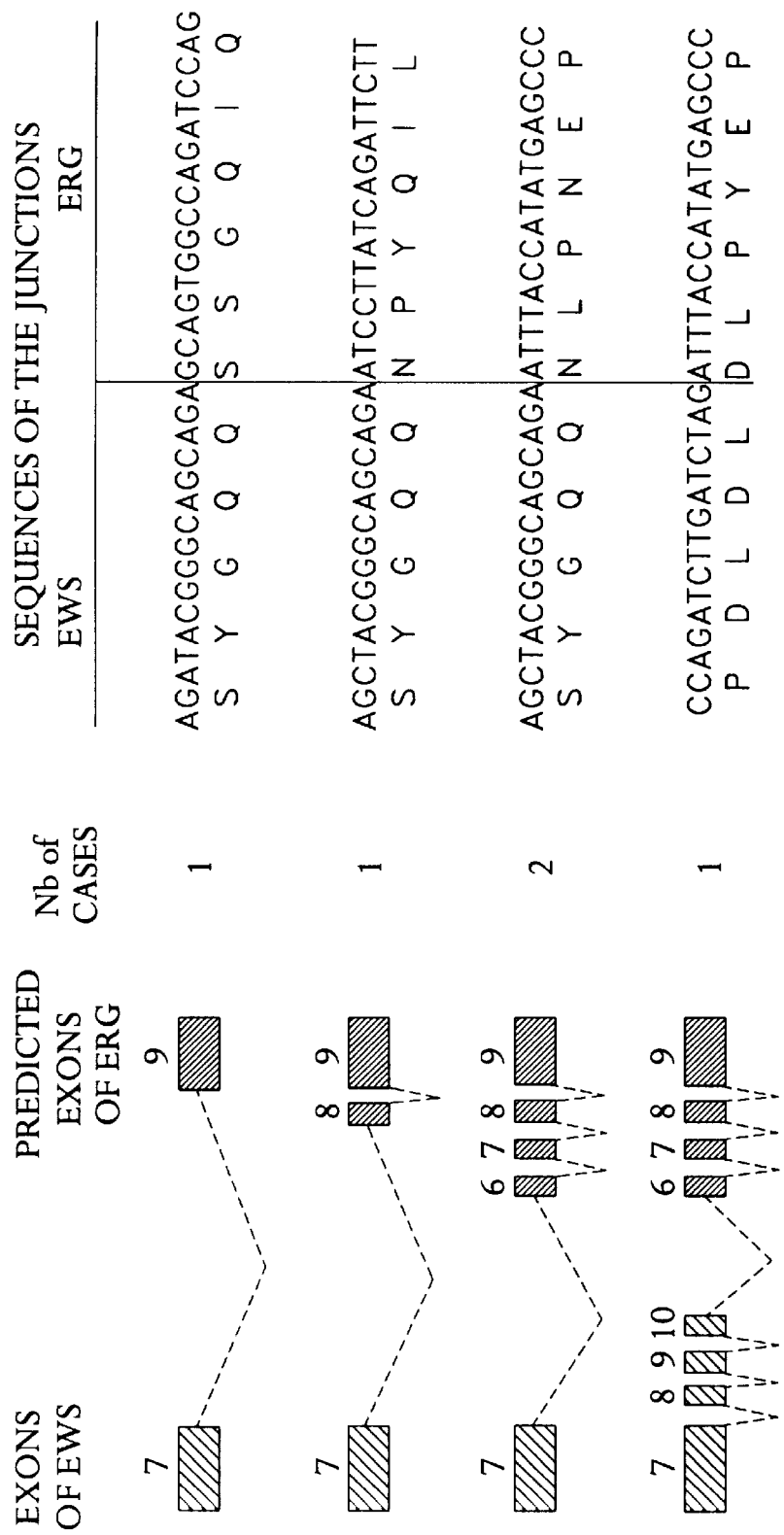
FIG. 18 shows exon juxtapositions of the Ews and ERG genes and the junction sequences of the resultant fusion transcripts SEQ ID NO:98/SEQ ID NO:99, SEQ ID NO:100/SEQ ID NO:101, SEQ ID NO:102/SEQ ID NO:103, and SEQ ID NO:104/SEQ ID NO:105, as respectively appear in the figure.

FIG. 18, in a nomenclature identical to that of FIGS. 14, 15 and 16, shows the junction sequences of four fusion transcripts corresponding to five cases observed, which juxtapose exon 7 of the gene Ews with the assumed exons 6, 8 and 9 of the gene Erg and the exon 10 of Ews with the assumed exon 6 of Erg.

EXAMPLE 3

STUDY OF THE RECURRENT CHROMOSOMAL TRANSLOCATION t(21;22) ASSOCIATED WITH SOFT TISSUE MALIGNANT MELANOMA (STMM)

I—Description of the Figures

Figure 19:
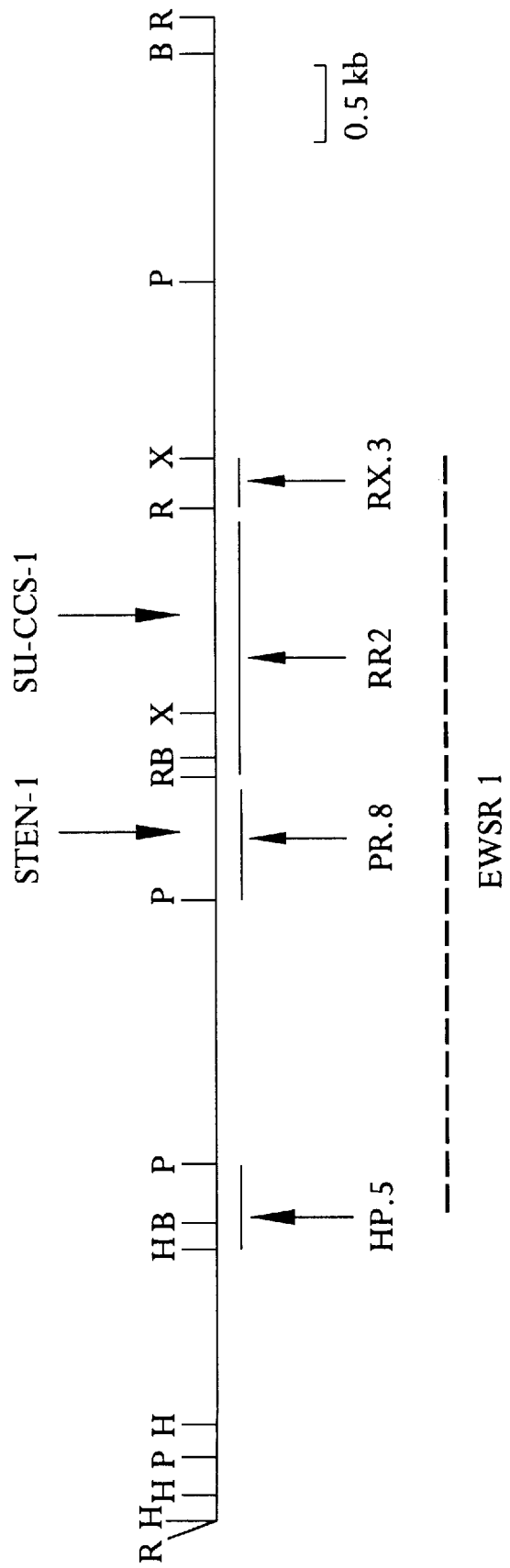
FIG. 19 shows a restriction map of the EWSR1 region of the Ews gene and the positions of the breakpoint in two tumor cell lines.
Figure 20A:
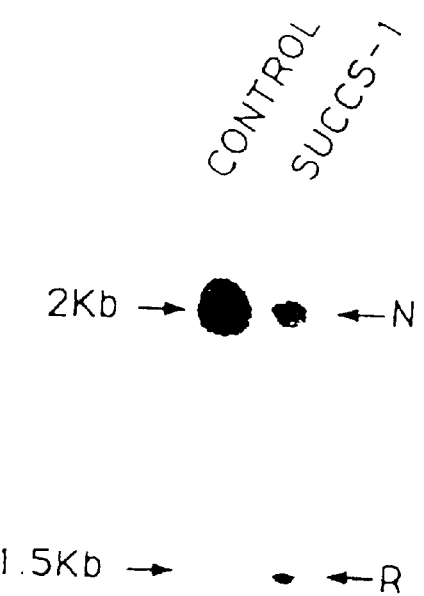
FIG. 20A shows Southern blot analysis of control DNA and from the STMM cell line SU-CCS-1.

FIGS. 19 and 20 show the rearrangement of the gene Ews in the cell line SU-CCS-1 of STMM.

FIG. 19 shows the restriction map of the region EWSR1 and indicates the position of the probes used and the deduced positions of the breakpoint of chromosome 22 in the tumor Sten-1 and in the cell line SU-CCS-1.

The portion (a) of FIG. 20 represents the analysis, by the Southern blot technique, of the control DNA and that of the SU-CCS-1 line doubly digested by EcoR1 and Pst1 and hybridized with the probe RR2 originating in EWSR1; in this figure, N indicates the normal band, and R indicates the band corresponding to the rearrangement.

Part (b) of FIG. 20 represents the northern blot detection of an abnormal transcript with the probe EWS-5' EB defined by the fragment 5' EcoR1/BamH1 of the cDNA of the gene Ews; the RNAs extracted from a HeLa cell line and a glioma cell line were used as controls; N indicates the normal transcript of the gene EWS, and R indicates an additional transcript.

Part (c) of FIG. 20 represents the analysis of the amplified products obtained in the last step of the RACE procedure; compared with the control RNA, which was used to promote the amplification from the normal EWS transcript (EWS), the RNA extracted from SU-CCS-1 has one additional amplified fragment, which has been shown to derive from the fusion transcript (Fusion).

Figure 21:
FIG. 21 shows PCR-reverse transcriptase detection of chimeric transcripts on agarose gel.
Figure 22:
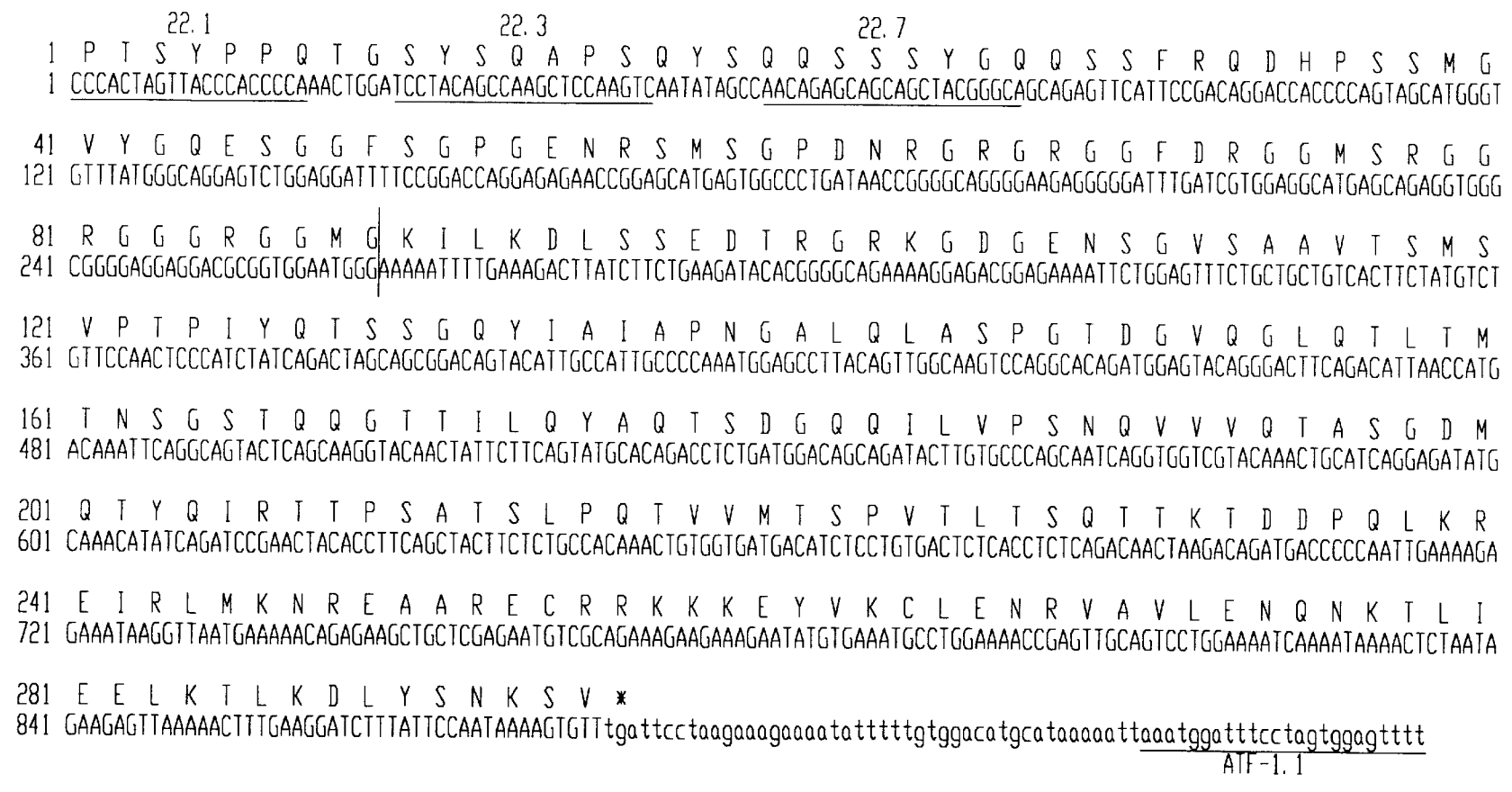

FIGS. 21 and 22 relate to the identification of the fusion transcript EWS/ATF-1 in the STMM tumors and cell lines.

FIG. 21 represents the PCR-reverse transcriptase detection of the chimera transcript. After reverse transcription of the total RNA of the SU-CCS-1 line, of the STMM tumors Sten-1 and 5852/88 and a HeLa cell line, PCR was done with the primers 22.1 (SEQ ID NO. 119) and ATF-1.1 (SEQ ID NO 125), corresponding respectively to the exon 7 of the gene Ews and to the 3' region translated at ATF-1. Analysis of the amplified products was done on a 1% agarose gel (control: no RNA).

FIG. 22 shows the sequence of the 954 bp cDNA fragment obtained by PCR-reverse transcriptase of the transcript resulting from the fusion of the genes Ews and Atf-1. The identical sequences (at the 5' region) or complementary (at the 3' region) to the primers used for the amplification are underlined in the figure. The vertical line indicates the junction between the two genes; it comes between the second and third positions of codon 325 and between the same positions of codon 65 of the gene Atf-1. The contribution of the sequence of the gene Ews is indicated in heavy characters. The position of the specific oligonucleotide of the gene Ews used in the RACE procedure is indicated and underlined.

Figure 24:
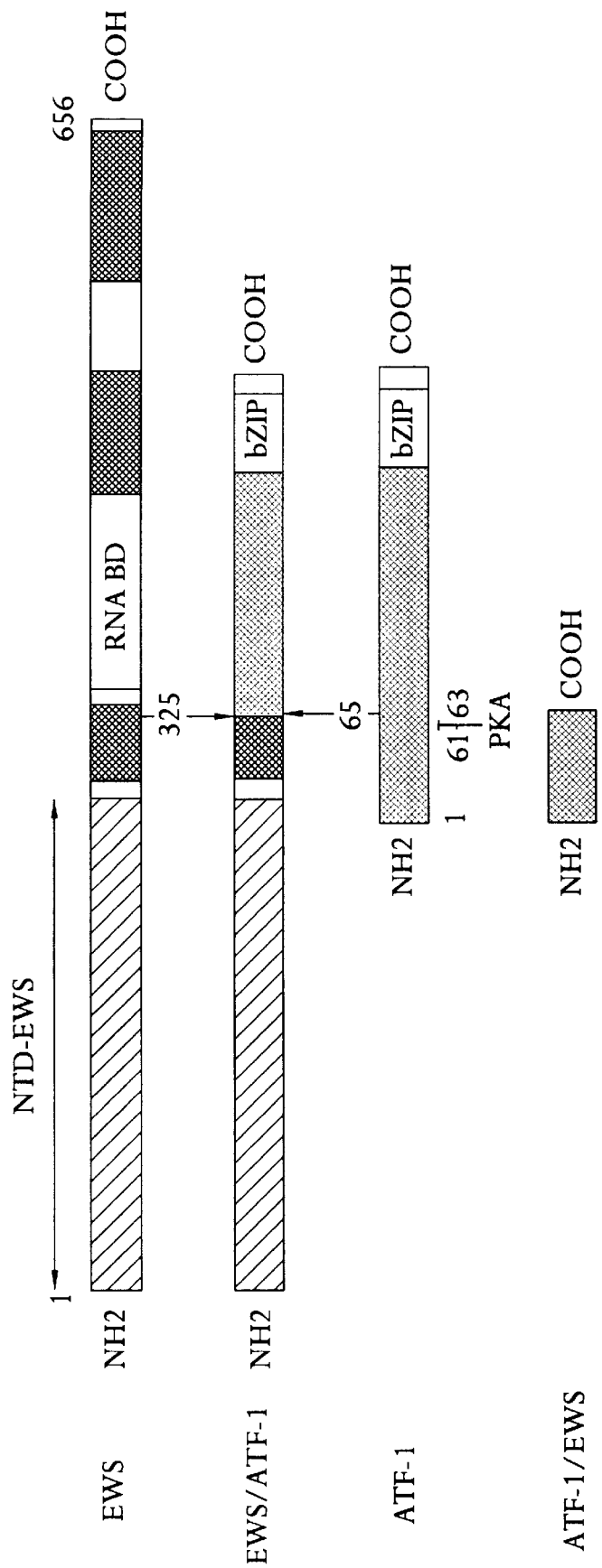
FIG. 24 shows the translation products of the four cDNAs shown in FIG. 23.

FIGS. 23 and 24 represent the junction of the chimera transcripts and provides a schematic illustration of the proteins deduced from them.

FIG. 23 shows the partial sequence of the cDNA of the genes Ews and Atf-1 and of their hybrid transcripts in the junction regions, showing the open and closed junction boxes, respectively, for the hybrid transcript Ews/Atf-1 from the der(22), and for the transcript Atf-1/Ews from the der(12).

FIG. 24 shows the products of translation corresponding to the 4 cDNAs indicated in FIG. 23. In the chimera protein EWS/ATF-1, the C-terminal portion of EWS containing two of the three regions rich in glycine (shaded regions) and the homologue RNA fixation domain (RNA-BD) are replaced by the C-terminal part of ATF-1 containing the basic fixation domain of DNA and the four leukin heptameres that together define the domain bZIP.

The reciprocal product is indicated by ATF-1/EWS and is coded by the chromosome der(12). The consensus recognition site for phosphorylation by the protein kinase A (amino acids 60 through 63) is indicated by PKA; NTD-EWS indicates the N-terminal domain of EWS.

II—Method

1) Tumors and Cell Lines

The cell line SU-CCS was prepared from a pleural effusion of STMM (L. Epstein, A. O. Martin, R. Kempson, Cancer Res. 44, 1265–1274 (1984)). Cytogenetic analysis revealed a complex karyotype having a single normal copy of chromosomes 12 and 22. The cell line was cultivated as described initially. The frozen fragments of primary STMM tumors, Sten-1 (G. Stenman, L-G Kindblom, L. Angervall, Genes Chrom. Cancer 4, 122–127, 1992), W9150 (F. Speleman, C. Colpaert, G. Goovaerts, J. G. Leroy, E. Van Marck, Cancer Genet. Cytogenet. 48, 176–179, 1992) and 5852/88 (A. A. Fletcher, Genes Chrom. Cancer 5, 184, 1992), were collected and kept frozen at −80° Celsius until used. All the primitive tumors were cytogenetically characterized beforehand, and they all have a translocation t(12;22) (q13;q12). Extraction of the DNA and RNA and the Southern and northern blot tests were done in accordance with standard procedures (T. Maniatis, E. F. Fritsh, J. Sambrook, J. Molecular Cloning. A Laboratory Manual, Cold Spring Harbor Laboratory Press, 1989).

2) Probes

The genome probes are shown in FIG. 19. The cDNA probes are as follows:

EWS 5' EB is the 0.8 Kb coding region of the cDNA of EWS that ends at a site BamH1;

EWS 3' XE is the last 0.85 Kb coding region beginning at site XbaI;

the probe ATF-1 3' was prepared by PCR and extends from nucleotide 754 to nucleotide 955 in FIG. 17.

3) Gene Amplification Procedure by PCR

All the PCR reactions were performed in 30 μl with the Amp TAQ kit sold by Cetus, and by using a cycler sold by Perkin Elmer. Unless otherwise indicated, 30 cycles were performed with the following parameters:

denaturation step: 940 Celsius for 30 seconds;

heating temperature: as indicated specifically for each case, for 60 seconds;

elongation: at 72° Celsius for 120 seconds.

The amplified products were analyzed on 1% agarose TBE gels.

4) Race Procedure

A polyA and polyA RNA μg of the cell line SU-CCS-1 was denatured for 10 minutes at 80° Celsius and transcripted using the PCR Gen Amp RNA kit sold by Cetus. The initial reverse transcription was performed in 2a μl using the A3'NV primer. Incubation at 42° Celsius for 45 minutes was followed by 5 minutes at 94° Celsius. An aliquote of two microliters of the resultant cDNA was amplified by PCR, using a three-step procedure involving straddling oligonucleotides. The first step uses the primers 22.1 and A3'-4 in 20 cycles (temperature of association 64° C.). 20 μl were analyzed on a 1% agarose gel with a low melting point. The portion of the gel containing the amplified products, of approximately 1.5 to 2.5 Kb, was collected, melted at 68° Celsius, and diluted in an equal volume of TE buffer. One microliter was subjected to PCR amplification (temperature of association 66° C.), using primers 22.3 and A3'-5. Analysis of 20 μl on a 1% agarose gel with a low melting point revealed two bands. For the sake of later characterization, each band was cut from the gel, diluted to $\frac{1}{1000}$ in a TE buffer, and 1 μl was amplified by PCR (temperature of association 67° C.), using primers 22.7 and A3'-6.

5) RT-PCR Analysis of the Transcripts of the STMM

A microgram of the total RNA was reverse transcripted using as the primer an oligo-dT and the PCR Gen Amp RNA kit made by Cetus, under the conditions described by the manufacturer. The cDNA obtained was subjected to three different PCR amplifications:

the amplified products corresponding to the transcripts Ews/Atf-1 were obtained with the primers 22.1 and ATF-1.1 (temperature of association 60° C.);

the amplified products corresponding to the normal transcript Atf-1 were obtained with the primers ATF-1.3 and ATF-1.1 (temperature of association 60° C.);

the amplified products corresponding to the transcripts Atf-1/Ews were obtained with the primers ATF-1.3 and 22.4 (temperature of association 65° C.).

6) Sequencing

The products of the PCR were subcloned in the phages M13mp18 and M13mp19. In each case, three independent clones were entirely sequenced with the Taq polymerase kit made by Applied Biosystems, using dideoxynucleotides and fluorescent primers. The reaction sequences were analyzed using an automatic sequencer made by applied biosystems.

7) Fluorescent In Situ Hybridization (FISH) Study

The library of genome cosmids constructed from the ICB 104 cell line and described by Zucman et al. (J. Zucman, O. Delattre, C. Desmaze, B. Plougastel, I. Joubert, T. Melot, M. Peter, P. De Jong, G. Rouleau, A. Aurias, G. Thomas, Genes Chrom. Cancer 5, 271–277, 1992) was screened with the part Atf-1 of the fusion transcript Ews/Atf-1, and the cosmids CCS2.2, F7 and G9 corresponding to the 3' and 5' region, respectively, of Ews. Monocolor and bicolor FISH analyses were done as described by Desmaze et al. (C. Desmaze, J. Zucman, O. Delattre, G. Thomas, A. Aurias, Genes Chrom. Cancer 5, 30–34, 1992).

III—Results

1) Alteration of the EWS Protein in STMM

The DNA was extracted from a primary STMM tumor, called Sten-1, having a characteristic translocation t(11;22) (G. Stenman, L-G Kindblom, L. Angervall, Genes Chrom. Cancer 4, 122–127, 1992), and a cell called SU-CCS-1 having a complex karyotype containing an abnormal chromosome 12 (L. Epstein, A. O. Martin, R. Kempson, Cancer Res. 44, 1265–1274 (1984)). The DNAs were screened with probes originating in EWSR1. The abnormal fragments were demonstrated with the probes PR.8 for Sten-1 and RR2 for SU-CCS-1 (as shown in FIG. 19). However, apparently normal DNAs from normal tissues were not accessible, and these abnormal bands, which have never been observed with DNA extracted from normal tissues, strongly suggest acquired somatic rearrangement (as shown in FIG. 16).

Figure 20B:
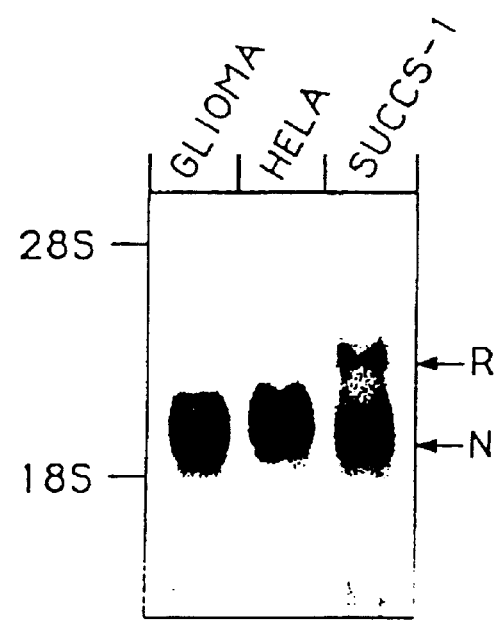
FIG. 20B shows Northern blot analysis of RNA from the STMM cell line SU-CCS-1 and from two control cell lines.

The RNAs originating in Sten-1, SU-CCS-1, and the primary STMM tumor 5852/88 (J. A. Fletcher, Genes Chrom. Cancer 5, 184, 1992) have been characterized by northern blot with the 3' and 5' ends of the cDNA of the gene Ews. The normal 2.5 Kb transcript of the gene Ews was demonstrated with the two probes. However, in the three cases, each probe specifically revealed one additional band (probe 5', a clearly expressed 3 Kb transcript; probe 3', a diffuse 1.5 Kb transcript), suggesting that these abnormal transcripts could correspond to the fusion genes generated by the translocation t(12;22), as FIG. 20(b) shows.

2) Cloning of the Hybrid Transcript

Figure 20C:
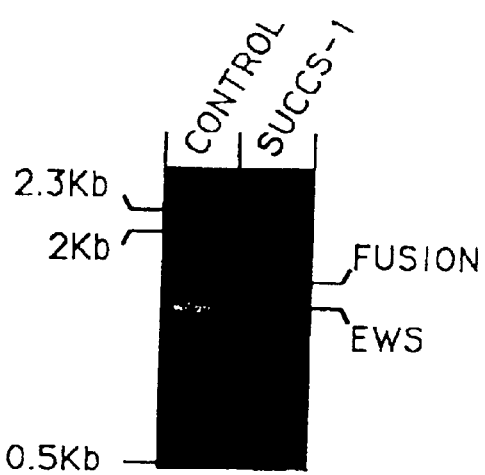
FIG. 20C shows analysis of amplified products from control RNA and from the STMM cell line SU-CCS-1.

In order to clone these transcripts, a method derived from the rapid amplification of the ends of cDNA was employed (A. F. Frohman, M. K. Dush, G. R. Martin, Proc. Natl. Acad. Sci. USA 85, 8998–9002, 1988; J. B. Dumas Milene Edwards, J. Delort, J. Mallet, Methods in Molecular Biology, Vol. 16, Chap. 35, 1992). PolyA RNAs of SU-CCS-1 and HeLa cells have been reverse transcripted using a $(dt)_{14}$ oligonucleotide marked at its 5' end with an artificial sequence of 51 nucleotides (as indicated above). The cDNA sequences localized between this marking and exon 7 of the gene Ews were amplified by PCR, using a three-step procedure. Agarose gel electrophoresis revealed that the HeLa RNAs lead to the amplification of a unique fragment 1.4 Kb in size, which was identified by hybridization as corresponding to the normal cDNA of the gene Ews. Except for this fragment, the SU-CCS-1 RNA lead to the amplification of a fragment of higher molecular weight as indicated in FIG. 20c. The sequencing determined an alien open reading phase fused to codon 325 on the 3' end of the eighth exon of the gene Ews. A search of the NBRF data bank revealed that this sequence codes for the C-terminal part of the gene Atf-1, with a transcription factor dependent on cMPA. At the level of the nucleic sequence, this sequence is identical to the 3' end of the cDNA sequence of the gene Atf-1 (T. Hai, F. Liu, W. J. Coukos, M. R. Green, Genes Dev. 3, 2083–2090, 1989; T. Yoshimura, J. -L. Fijisawa, M. Yoshida, EMBA J. 9, 2537–2542, 1990). A probe originating in this end, named ATF-1 3', hybridizes with the abnormal 3 Kb transcript observed by northern blot.

A more direct procedure for testing the presence of a fusion transcript Ews/Atf-1 in the tumor RNA was developed from a specific oligonucleotide deriving from the non-translated 3' region of the gene Atf-1. This primer was used, in combination with an oligonucleotide homologous to exon 7 of the gene Ews, for PCR amplification of cDNAs primed with an oligo-dT synthesized from three known primary STMM tumors, of the SU-CCS-1 cell line and control HeLa cells. Except for the HeLa RNA, which did not lead to any amplification, the four RNAs of the STMM cases lead to a major 1 Kb fragment (as shown in FIG. 21). For each case, the sequencing revealed the same junction in phase, coming between codon 325 of the gene Ews and codon 65 of the gene Atf-1. (as shown in FIG. 21). The fusion protein deduced as being coded by this transcript has preserved the entirety of the N-terminal domain of the protein EWS and the major portion of the protein ATF-1 (as shown in FIG. 23).

3) Mapping of the Gene Atf-1 on Chromosome 12

The portion of the fusion transcript corresponding to the gene Atf-1 was used to retrieve a cosmid from the human genome bank. It was demonstrated by fluorescent in situ hybridization (FISH) on chromosomes in metaphase that this cosmid covers exclusively the band 12q13, thus demonstrating that the gene Atf-1 is localized in this region of the genome. The complexity of the karyotype of the SU-CCS-1 cells rules out a simple formal cytogenetic demonstration of the appearance of a translocation involving chromosomes 12 and 22. Nevertheless, bicolor FISH analysis of the SU-CCS-1 cell nucleii in interphase has shown that the locus of the gene Ews was divided, and that the proximal portion of the gene Ews was juxtaposed with the locus of the gene Atf-1.

4) Reciprocal Fusion Gene

Transcription of the normal gene Atf-1 on chromosome 12 and that of the reciprocal fusion gene generated in chromosome der(12) have been studied by reverse transcriptase PCR. In all cases of STMM, the two transcripts were expressed; this result is compatible with the wide spectrum of expression of the gene Atf-1 (T. Yoshimura, J. -I. Fijisawa, M. Yoshida, EMBO J. 9, 2537–2542, 1990). In all cases, the amplified products originating from the reciprocal fusion transcript are identical in size but shorter than anticipated. Sequencing the junction region of the Sten-1 tumor cDNA revealed an out-of-phase fusion caused by the deletion or splicing of the ninth exon of the gene Ews. The deduced translation product is a truncated protein composed of the first 65 amino acids of the protein ATF-1; followed by three aberrant amino acids (as shown in FIG. 23).

IV—Discussion

The present study demonstrates that the translocation t(12;22) associated with STMM generates hybrid genes associating part of the gene Ews and part of the gene Atf-1, whose structural and functional characteristics resemble those of the fusion of the genes Ews and Hum-Fli-1 in the translocation t(11;22) which associates it with Ewing's sarcoma. In both cases, the chimera gene generated on chromosome der(22) codes for a protein in which the same portion of the N-terminal portion of the protein EWS is linked to a DNA fixation domain of a transcription factor. It has thus been demonstrated in the models that the preserved portion of the N-terminal portion of the protein EWS, when it is linked to the DNA fixation domain of the proteins HUM-FLI-1, ETS-1 or GAL-4, led to the transcription of specific reporter genes containing, in their promoter region, the corresponding response elements.

The hybrid protein deduced from the fusion DNA sequence of the genes Ews and Atf-1 contains the major portion of the protein ATF-1, of which one important functional domain is bZIP. This domain is known to mediate the dimerization of the protein and the DNA fixation. As a consequence it is possible to consider that these two properties are observed in the hybrid protein. That should accordingly be capable of forming homodimers and heterodimers with the transcription factor CREB known to interact with normal ATF-1 protein (C. Turc-Carel, A. Aurias, F. Mugneret, I. Lizard Sidaner, C. Volk, J. -P. Thiery, S. Olschwang, T. Philip, G. M. Lenoir, A. Mazabraud, Cancer Genet. Cytogenet. 32, 229–238, 1988; E. C. Douglass, M. Valentine, A. A. Green, F. A. Hayes, E. I. Thompson, J. Nat. Cancer Inst. 77, 1211–1213, 1988). It is also possible for the patterns recognized by the ATF-1 protein to be fixed to the DNA. However, the chimera protein has lost one phosphorylation consensus site of the protein kinase A, which can contribute to regulating the transcription activity of the gene Atf-1 by cMPA (T. Yoshimura, J.-I. Fijisawa, M. Yoshida, EMBO J. 9, 2537–2542, 1990; K. J. Flink, N. C. Jones, Oncogene 6, 2019–2026, 1991).

The chimera protein including part of the protein EWS and part of the protein ATF-1, which potentially has the Ews transactivator domain linked with the domain bZIP, which is no longer regulated by cMPA, of ATF-1, can alter the regulation of the transcription of genes normally controlled by ATF-1.

In the majority of STMM cases, the two transcript hybrids are generated by a single cytogenetic translocation, suggesting that the transcription of the gene Atf-1 is identical to that of the gene Ews, from the centromere to the telomere. Both are expressed. This situation had already been observed in several malignant hematologic tumors. In fact, it has been demonstrated that the chromosomes of the translocation t(15;17) associated with promyelotic leukemia (D. C. Tkachuk, C. Kohler, M. L. Cleary, Cell 71, 691–700, 1992), those of the translocation t(14;11) associated with acute lymphocytic leukemias in the child (Y. Gu, T. Nakamura, H. Alder, R, Prasad, O. Canaani, G. Cimino, C. M. Groce, R. Canaani, Cell 71, 701–708, 1992) in each case express aberrant fusion transcripts. In STMM, the expression of a reciprocal fusion gene on the chromosome der(12) is compatible with the generally known expression of ATF-1. Nevertheless, because of the external fusion frame of the two coding sequences, its deduced expression product is nearly entirely made up of the first 65 amino acids of the n-terminal region of the protein ATF-1. The truncated ATF-1 protein accordingly would never have to form dimers or to link DNA. The contribution of this truncated protein to the phenotype of the tumor remains obscure. Nevertheless, it must not be essential to the proliferation of the tumor, since on one occasion the chromosome der(12) has a deletion in 30% of the tumor cells (G. Stenma, L-G Kindblom, L. Angervall, Genes Chrom. Cancer 4, 122–127, 1992). In the case of Ewing's sarcoma, reciprocal fusion is not expressed at a measureable level, and the chromosome der(11) is deleted only in some cases (C. Turc-Carel, A. Aurias, F. Mugneret, I. Lizard Sidaner, C. Volk, J. -P. Thiery, S. Olschwang, T. Philip, G. M. Lenoir, Cancer Genet. Cytogenet. 32, 229–238, 1988; A. C. Douglass, M. Valentine, A. A. Green, F. A. Hayes, E. I. Thompson, J. Nat. Cancer Inst., 1211–1213, 1986).

In the case of acute lymphocytic leukemia, the N-terminal transactivator domain of E2A can be linked to either the PBXl domain or the bZIP domain of HLF (T. Inaba, W. M. Roberts, L. H. Shapiro, K. W. Jolly, S. C. Raimondi, S. D. Smith, A. T. Look, Science 257, 521–534, 1992; S. P. Hunger, K. Ohyashiki, K. Toyama, M. L. Cleary, Genes Develop. 6, 1608–1620, 1992). The present study demonstrates a similar mode of oncogenetic conversion of solid tumors. In fact, the N-terminal transactivator domain of EWS can be fused to the DNA fixation domain of different families of transcription factors: the domain ETS in the case of Ewing's sarcoma, the domain bZIP in the case of STMM. This suggests a common oncogenetic mechanism mediated by the N-terminal domain of EWS, contained in both the chimera proteins EWS/HUM-FLI-1 and EWS/ATF-1.

We claim:

1. An isolated DNA sequence comprising nucleotides 1 to 2372 in Sequence ID No. 1, which DNA sequence is the Ews gene of chromosome 22.

2. An isolated RNA sequence which is complementary to the DNA sequence shown in Sequence ID No. 1.

3. An isolated DNA sequence comprising nucleotides 1 to 2796 in Sequence ID No. 3, which DNA is the Hum-Fli-1 gene of chromosome 11, and which gene translocates with the Ews gene of chromosome 22, and which translocation is associated with the development of Ewing's Sarcoma.

4. A hybrid DNA sequence comprising a portion of the Ews gene as shown in Sequence ID No. 1 from its 5' end up to and including exon 7 of the Ews gene linked to a portion of a second gene from its 3' end up to and including exon 9 of the second gene, which second gene is selected from the group consisting of the Hum-Fli-1 gene of chromosome 11, the Erg gene of chromosome 21, and the Atf-1 gene of chromosome 12.

5. The hybrid DNA sequence of claim 4 wherein the portion of the Ews gene comprises the nucleotide sequence of the Ews gene from its 5' end up to the EWSR1 region of the Ews gene at a translocation breakpoint.

6. The hybrid DNA sequence of claim 4 which has a breakpoint at about nucleotide 820 of Sequence ID No. 1.

7. The hybrid DNA sequence of claim 4 which has a breakpoint at about nucleotide 1072 of Sequence ID No. 1.

8. The hybrid DNA sequence of claim 4 which comprises up to and including exon 8 of the second gene.

9. The hybrid DNA sequence of claim 8 wherein the second gene is the Hum-Fli-1 gene.

10. The hybrid DNA sequence of claim 9 wherein the portion of the Hum-Fli-1 gene comprises the nucleotide sequence of the Hum-Fli-1 gene from its 3' end to a EWSR2 region at a translocation breakpoint.

11. The hybrid DNA sequence of claim 9 wherein the Hum-Fli-1 gene is under the control of an ectopic promoter, which is the Ews promoter.

12. The hybrid DNA sequence of claim 8 wherein the second gene is the Erg gene.

13. The hybrid DNA sequence of claim 8 wherein the second gene is the Atf-1 gene.

14. The hybrid DNA sequence of claim 4 which comprises a foreign DNA sequence between the Ews gene and the second gene.

15. An isolated polypeptide as shown as amino acids 1 to 656 in Sequence ID No. 2, which polypeptide is encoded by the Ews gene of chromosome 22.

16. The isolated polypeptide of claim 15 wherein about 46% of the total amino acids from number 300 to 340, 454 to 513, and number 559 to 640 of Sequence ID No. 2 are glycine.

17. The isolated polypeptide of claim 16 wherein about 19% of the total amino acids from number 300 to 340, 454 to 513, and number 559 to 640 of Sequence ID No. 2 are arginine.

18. An isolated polypeptide comprising amino acids 1 to 452 in Sequence ID No. 4, which polypeptide is encoded by the Hum-Fli-1 gene of chromosome 11, and which gene translocates with the Ews gene of chromosome 22, and which translocation is implicated with the appearance of Ewing's Sarcoma.

19. A fusion protein comprising a portion of the Ews polypeptide from the amino terminal to amino acid 265, as shown in Sequence ID No. 2 and a portion comprising the carboxy terminal of a second polypeptide selected from the group consisting of polypeptides encoded by the Hum-Fli-1 gene of chromosome 11, the Erg gene of chromosome 21, and the Atf-1 gene of chromosome 12, wherein the carboxy terminal of the second polypeptide is encoded by the second gene portion of claim 4.

20. The fusion protein of claim 19 wherein the second polypeptide is Hum-Fli-1.

21. The fusion protein of claim 19 wherein the second polypeptide is Erg.

22. The fusion protein of claim 19 wherein the second polypeptide is Atf-1.

23. The fusion protein which is encoded by the hybrid DNA sequence of claim 4.

24. The fusion protein of claim 19 which comprises the portion of the Ews polypeptide from the amino terminal to amino acid 349, as shown in Sequence ID No. 2.

25. A complementary nucleic acid sequence for hybridizing to the hybrid DNA sequence of claim 4 or to an mRNA sequence transcribed by the hybrid DNA sequence.

26. A kit for determining the presence in a human cell of a translocation involving chromosome 22, which kit comprises:
a probe which hybridize to a hybrid DNA sequence comprising a portion of the Ews gene and a portion of a gene selected from the group consisting of Erg and Atf-1, or mRNA transcribed from the hybrid DNA sequence, wherein the probe hybridizes to both the Ews portion and the Erg or Atf-1 portion of the DNA sequence or the mRNA, and control specimens of DNA or RNA.

27. A method for determining the presence in a patient of a translocation of the Ews gene of chromosome 22 and a gene selected from the group comprising the Erg gene of chromosome 21 and the Atf-1 gene of chromosome 12, which method comprises
treating a biological specimen from the patient to render the nucleic acids in the specimen accessible to a nucleic acid probe,
contacting the specimen with a probe which hybridizes to the hybrid DNA sequence of claim 4 or to an mRNA sequence transcribed by the hybrid DNA sequence, wherein the probe hybridizes to both the Ews portion and the Hum-Fli-1, Erg or Atf-1 portion of the DNA sequence or the mRNA, and
detecting the hybrids of the hybrid DNA sequence or the mRNA and the probe, the presence of which is diagnostic of the translocation.

28. A method for diagnosing Ewing's Sarcoma in a patient, which method comprises:
treating a biological specimen from the patient to render the nucleic acids in the specimen accessible to a nucleic acid probe,
contacting the specimen with a probe which hybridizes to the hybrid DNA sequence of claim 4 or to an mRNA sequence transcribed by the hybrid DNA sequence, wherein the probe hybridizes to both the Ews portion and the Hum-Fli-1, Erq or Atf-1 portion of the DNA sequence or the mRNA,
detecting the hybrids of the DNA or mRNA sequence and the probe, the presence of which is diagnostic of Ewing's sarcoma.

29. A kit for determining the presence in a human cell of a translocation involving chromosome 22, which kit comprises a reverse transcriptase and PCR primers which amplify cDNA comprising a portion of the Ews gene and a portion of a gene selected from the group consisting of Erg and Atf-1, wherein the portions of the Ews, Erg, and Atf-1 genes are as defined in claim 4, and control specimens of DNA or RNA.

30. The hybrid DNA of claim 12, which comprises a junction sequence between the Ews and Erg genes selected from the group consisting of the sequences shown in Sequence ID Nos. 98, 100, 102, and 104.

31. An isolated fusion protein resulting from a chromosomal translation t(21;22), present in tumor cells, wherein the fusion protein comprises the sequence of amino acids encoded by the hybrid DNA of claim 30.

32. The protein of claim 31, which comprises the N-terminal of the EWS protein and the C-terminal of the ERG protein.

33. A method for diagnosing Ewing's sarcoma, comprising the following steps:
extracting mRNA from a biological specimen from tumor cells of a patient that are likely to have a chromosomal translocation t(21;22);
synthesizing a cDNA complementary to said mRNA by reverse transcription of the mRNA;
amplifying the cDNA;
analyzing the amplified products; and
detecting the presence of a product of the fusion gene resulting from the translocation t(21;22), thereby diagnosing Ewing's sarcoma.

34. The hybrid DNA of claim 13, which comprises the part of the nucleotide sequence of the Ews gene up to the EWSR1 region at the level of which the breakpoint of chromosome 22 is located, and the part of the nucleotide sequence of the Atf-1 gene from the region at the level of which the breakpoint of chromosome 12 is located in this translocation, to its 3' end.

35. The hybrid DNA of claim 13 which comprises the sequence shown in Sequence ID No. 106.

36. The hybrid DNA of claim 35 which comprises a junction sequence between the Ews and Atf-1 genes selected from the group consisting of sequences shown in Sequence ID Nos. 111, 113, and 115.

37. An isolated fusion protein resulting from a chromosomal translocation t(12;22), present in tumor cells, which comprises the sequence of amino acids coded by the hybrid DNA of claim 35.

38. The protein of claim 37 which comprises the N-terminal of the EWS protein and the C-terminal of the Atf-1 protein.

39. The hybrid DNA of claim 37, wherein its sequence of amino acid comprises the sequence shown in Sequence ID No. 106.

40. A method for diagnosing soft tissue malignant melanoma, comprising the following steps:

extracting mRNA from a biological specimen from tumor cells of a patient that are likely to have a chromosomal translocation t(12;22);

synthesizing a cDNA complementary to the mRNA by reverse transcription of the mRNA;

amplifying the cDNA;

analyzing the amplified products; and detecting the presence of a product of the fusion gene resulting from the translocation t(12;22), thereby diagnosing soft tissue malignant melanoma.

* * * * *

SEQUENCE LISTING (1) GENERAL INFORMATION:

(iii) NUMBER OF SEQUENCES: 129

(2) INFORMATION FOR SEQ ID NO:1:

(i) SEQUENCE CHARACTERISTICS:
      (A) LENGTH: 2371 base pairs
      (B) TYPE: nucleic acid
      (C) STRANDEDNESS: double
      (D) TOPOLOGY: linear (ix) FEATURE:
      (A) NAME/KEY: CDS
      (B) LOCATION: 25..1992

(xi) SEQUENCE DESCRIPTION: SEQ ID NO:1:

```
GAGAACGAGG AGGAAGGAGA GAAA ATG GCG TCC ACG GAT TAC AGT ACC TAT            51
                          Met Ala Ser Thr Asp Tyr Ser Thr Tyr
                          1               5

AGC CAA GCT GCA GCG CAG CAG GGC TAC AGT GCT TAC ACC GCC CAG CCC           99
Ser Gln Ala Ala Ala Gln Gln Gly Tyr Ser Ala Tyr Thr Ala Gln Pro
 10                  15                  20                  25

ACT CAA GGA TAT GCA CAG ACC ACC CAG GCA TAT GGG CAA CAA AGC TAT          147
Thr Gln Gly Tyr Ala Gln Thr Thr Gln Ala Tyr Gly Gln Gln Ser Tyr
                 30                  35                  40

GGA ACC TAT GGA CAG CCC ACT GAT GTC AGC TAT ACC CAG GCT CAG ACC          195
Gly Thr Tyr Gly Gln Pro Thr Asp Val Ser Tyr Thr Gln Ala Gln Thr
             45                  50                  55

ACT GCA ACC TAT GGG CAG ACC GCC TAT GCA ACT TCT TAT GGA CAG CCT          243
Thr Ala Thr Tyr Gly Gln Thr Ala Tyr Ala Thr Ser Tyr Gly Gln Pro
         60                  65                  70

CCC ACT GGT TAT ACT ACT CCA ACT GCC CCC CAG GCA TAC AGC CAG CCT          291
Pro Thr Gly Tyr Thr Thr Pro Thr Ala Pro Gln Ala Tyr Ser Gln Pro
     75                  80                  85

GTC CAG GGG TAT GGC ACT GGT GCT TAT GAT ACC ACC ACT GCT ACA GTC          339
Val Gln Gly Tyr Gly Thr Gly Ala Tyr Asp Thr Thr Thr Ala Thr Val
 90                  95                 100                 105

ACC ACC ACC CAG GCC TCC TAT GCA GCT CAG TCT GCA TAT GGC ACT CAG          387
Thr Thr Thr Gln Ala Ser Tyr Ala Ala Gln Ser Ala Tyr Gly Thr Gln
                110                 115                 120

CCT GCT TAT CCA GCC TAT GGG CAG CAG CCA GCA GCC ACT GCA CCT ACA          435
Pro Ala Tyr Pro Ala Tyr Gly Gln Gln Pro Ala Ala Thr Ala Pro Thr
            125                 130                 135

AGA CCG CAG GAT GGA AAC AAG CCC ACT GAG ACT AGT CAA CCT CAA TCT          483
Arg Pro Gln Asp Gly Asn Lys Pro Thr Glu Thr Ser Gln Pro Gln Ser
        140                 145                 150

AGC ACA GGG GGT TAC AAC CAG CCC AGC CTA GGA TAT GGA CAG AGT AAC          531
Ser Thr Gly Gly Tyr Asn Gln Pro Ser Leu Gly Tyr Gly Gln Ser Asn
    155                 160                 165

TAC AGT TAT CCC CAG GTA CCT GGG AGC TAC CCC ATG CAG CCA GTC ACT          579
Tyr Ser Tyr Pro Gln Val Pro Gly Ser Tyr Pro Met Gln Pro Val Thr
170                 175                 180                 185

GCA CCT CCA TCC TAC CCT CCT ACC AGC TAT TCC TCT ACA CAG CCG ACT          627
Ala Pro Pro Ser Tyr Pro Pro Thr Ser Tyr Ser Ser Thr Gln Pro Thr
                190                 195                 200

AGT TAT GAT CAG AGC AGT TAC TCT CAG CAG AAC ACC TAT GGG CAA CCG          675
Ser Tyr Asp Gln Ser Ser Tyr Ser Gln Gln Asn Thr Tyr Gly Gln Pro
            205                 210                 215

AGC AGC TAT GGA CAG CAG AGT AGC TAT GGT CAA CAA AGC AGC TAT GGG          723
Ser Ser Tyr Gly Gln Gln Ser Ser Tyr Gly Gln Gln Ser Ser Tyr Gly
```

-continued

|     |     |     |     | 220 |     |     |     |     | 225 |     |     |     |     | 230 |     |      |
|-----|-----|-----|-----|-----|-----|-----|-----|-----|-----|-----|-----|-----|-----|-----|-----|------|
| CAG | CAG | CCT | CCC | ACT | AGT | TAC | CCA | CCC | CAA | ACT | GGA | TCC | TAC | AGC | CAA | 771  |
| Gln | Gln | Pro | Pro | Thr | Ser | Tyr | Pro | Pro | Gln | Thr | Gly | Ser | Tyr | Ser | Gln |      |
| 235 |     |     |     |     | 240 |     |     |     |     | 245 |     |     |     |     |     |      |
| GCT | CCA | AGT | CAA | TAT | AGC | CAA | CAG | AGC | AGC | AGC | TAC | GGG | CAG | CAG | AGT | 819  |
| Ala | Pro | Ser | Gln | Tyr | Ser | Gln | Gln | Ser | Ser | Ser | Tyr | Gly | Gln | Gln | Ser |      |
| 250 |     |     |     |     | 255 |     |     |     |     | 260 |     |     |     |     | 265 |      |
| TCA | TTC | CGA | CAG | GAC | CAC | CCC | AGT | AGC | ATG | GGT | GTT | TAT | GGG | CAG | GAG | 867  |
| Ser | Phe | Arg | Gln | Asp | His | Pro | Ser | Ser | Met | Gly | Val | Tyr | Gly | Gln | Glu |      |
|     |     |     | 270 |     |     |     |     | 275 |     |     |     |     | 280 |     |     |      |
| TCT | GGA | GGA | TTT | TCC | GGA | CCA | GGA | GAG | AAC | CGG | AGC | ATG | AGT | GGC | CCT | 915  |
| Ser | Gly | Gly | Phe | Ser | Gly | Pro | Gly | Glu | Asn | Arg | Ser | Met | Ser | Gly | Pro |      |
|     |     |     | 285 |     |     |     |     | 290 |     |     |     |     | 295 |     |     |      |
| GAT | AAC | CGG | GGC | AGG | GGA | AGA | GGG | GGA | TTT | GAT | CGT | GGA | GGC | ATG | AGC | 963  |
| Asp | Asn | Arg | Gly | Arg | Gly | Arg | Gly | Gly | Phe | Asp | Arg | Gly | Gly | Met | Ser |      |
|     |     | 300 |     |     |     |     | 305 |     |     |     |     | 310 |     |     |     |      |
| AGA | GGT | GGG | CGG | GGA | GGA | GGA | CGC | GGT | GGA | ATG | GGC | AGC | GCT | GGA | GAG | 1011 |
| Arg | Gly | Gly | Arg | Gly | Gly | Gly | Arg | Gly | Gly | Met | Gly | Ser | Ala | Gly | Glu |      |
|     | 315 |     |     |     |     | 320 |     |     |     |     | 325 |     |     |     |     |      |
| CGA | GGT | GGC | TTC | AAT | AAG | CCT | GGT | GGA | CCC | ATG | GAT | GAA | GGA | CCA | GAT | 1059 |
| Arg | Gly | Gly | Phe | Asn | Lys | Pro | Gly | Gly | Pro | Met | Asp | Glu | Gly | Pro | Asp |      |
| 330 |     |     |     |     | 335 |     |     |     |     | 340 |     |     |     |     | 345 |      |
| CTT | GAT | CTA | GGC | CCT | CCT | GTA | GAT | CCA | GAT | GAA | GAC | TCT | GAC | AAC | AGT | 1107 |
| Leu | Asp | Leu | Gly | Pro | Pro | Val | Asp | Pro | Asp | Glu | Asp | Ser | Asp | Asn | Ser |      |
|     |     |     | 350 |     |     |     |     | 355 |     |     |     |     | 360 |     |     |      |
| GCA | ATT | TAT | GTA | CAA | GGA | TTA | AAT | GAC | AGT | GTG | ACT | CTA | GAT | GAT | CTG | 1155 |
| Ala | Ile | Tyr | Val | Gln | Gly | Leu | Asn | Asp | Ser | Val | Thr | Leu | Asp | Asp | Leu |      |
|     |     |     | 365 |     |     |     |     | 370 |     |     |     |     | 375 |     |     |      |
| GCA | GAC | TTC | TTT | AAG | CAG | TGT | GGG | GTT | GTT | AAG | ATG | AAC | AAG | AGA | ACT | 1203 |
| Ala | Asp | Phe | Phe | Lys | Gln | Cys | Gly | Val | Val | Lys | Met | Asn | Lys | Arg | Thr |      |
|     |     |     | 380 |     |     |     |     | 385 |     |     |     |     | 390 |     |     |      |
| GGG | CAA | CCC | ATG | ATC | CAC | ATC | TAC | CTG | GAC | AAG | GAA | ACA | GGA | AAG | CCC | 1251 |
| Gly | Gln | Pro | Met | Ile | His | Ile | Tyr | Leu | Asp | Lys | Glu | Thr | Gly | Lys | Pro |      |
|     | 395 |     |     |     |     | 400 |     |     |     |     | 405 |     |     |     |     |      |
| AAA | GGC | GAT | GCC | ACA | GTG | TCC | TAT | GAA | GAC | CCA | CCC | ACT | GCC | AAG | GCT | 1299 |
| Lys | Gly | Asp | Ala | Thr | Val | Ser | Tyr | Glu | Asp | Pro | Pro | Thr | Ala | Lys | Ala |      |
| 410 |     |     |     |     | 415 |     |     |     |     | 420 |     |     |     |     | 425 |      |
| GCC | GTG | GAA | TGG | TTT | GAT | GGG | AAA | GAT | TTT | CAA | GGG | AGC | AAA | CTT | AAA | 1347 |
| Ala | Val | Glu | Trp | Phe | Asp | Gly | Lys | Asp | Phe | Gln | Gly | Ser | Lys | Leu | Lys |      |
|     |     |     |     | 430 |     |     |     |     | 435 |     |     |     |     | 440 |     |      |
| GTC | TCC | CTT | GCT | CGG | AAG | AAG | CCT | CCA | ATG | AAC | AGT | ATG | CGG | GGT | GGT | 1395 |
| Val | Ser | Leu | Ala | Arg | Lys | Lys | Pro | Pro | Met | Asn | Ser | Met | Arg | Gly | Gly |      |
|     |     |     | 445 |     |     |     |     | 450 |     |     |     |     | 455 |     |     |      |
| CTG | CCA | CCC | CGT | GAG | GGC | AGA | GGC | ATG | CCA | CCA | CCA | CTC | CGT | GGA | GGT | 1443 |
| Leu | Pro | Pro | Arg | Glu | Gly | Arg | Gly | Met | Pro | Pro | Pro | Leu | Arg | Gly | Gly |      |
|     |     | 460 |     |     |     |     | 465 |     |     |     |     | 470 |     |     |     |      |
| CCA | GGA | GGC | CCA | GGA | GGT | CCT | GGG | GGA | CCC | ATG | GGT | CGC | ATG | GGA | GGC | 1491 |
| Pro | Gly | Gly | Pro | Gly | Gly | Pro | Gly | Gly | Pro | Met | Gly | Arg | Met | Gly | Gly |      |
|     | 475 |     |     |     |     | 480 |     |     |     |     | 485 |     |     |     |     |      |
| CGT | GGA | GGA | GAT | AGA | GGA | GGC | TTC | CCT | CCA | AGA | GGA | CCC | CGG | GGT | TCC | 1539 |
| Arg | Gly | Gly | Asp | Arg | Gly | Gly | Phe | Pro | Pro | Arg | Gly | Pro | Arg | Gly | Ser |      |
| 490 |     |     |     |     | 495 |     |     |     |     | 500 |     |     |     |     | 505 |      |
| CGA | GGG | AAC | CCC | TCT | GGA | GGA | GGA | AAC | GTC | CAG | CAC | CGA | GCT | GGA | GAC | 1587 |
| Arg | Gly | Asn | Pro | Ser | Gly | Gly | Gly | Asn | Val | Gln | His | Arg | Ala | Gly | Asp |      |
|     |     |     | 510 |     |     |     |     | 515 |     |     |     |     | 520 |     |     |      |
| TGG | CAG | TGT | CCC | AAT | CCG | GGT | TGT | GGA | AAC | CAG | AAC | TTC | GCC | TGG | AGA | 1635 |
| Trp | Gln | Cys | Pro | Asn | Pro | Gly | Cys | Gly | Asn | Gln | Asn | Phe | Ala | Trp | Arg |      |
|     |     |     | 525 |     |     |     |     | 530 |     |     |     |     | 535 |     |     |      |
| ACA | GAG | TGC | AAC | CAG | TGT | AAG | GCC | CCA | AAG | CCT | GAA | GGC | TTC | CTC | CCG | 1683 |
| Thr | Glu | Cys | Asn | Gln | Cys | Lys | Ala | Pro | Lys | Pro | Glu | Gly | Phe | Leu | Pro |      |

|  | 540 |  |  |  | 545 |  |  |  | 550 |  |  |  |
|---|---|---|---|---|---|---|---|---|---|---|---|---|
| CCA | CCC | TTT | CCG | CCC | CCG | GGT | GGT | GAT | CGT | GGC | AGA | GGT | GGC | CCT | GGT | 1731 |
| Pro | Pro | Phe | Pro | Pro | Pro | Gly | Gly | Asp | Arg | Gly | Arg | Gly | Gly | Pro | Gly |  |
| 555 |  |  |  |  | 560 |  |  |  |  | 565 |  |  |  |  |  |  |

```
CCA CCC TTT CCG CCC CCG GGT GGT GAT CGT GGC AGA GGT GGC CCT GGT     1731
Pro Pro Phe Pro Pro Pro Gly Gly Asp Arg Gly Arg Gly Gly Pro Gly
555                 560                 565

GGC ATG CGG GGA GGA AGA GGT GGC CTC ATG GAT CGT GGT GGT CCC GGT     1779
Gly Met Arg Gly Gly Arg Gly Gly Leu Met Asp Arg Gly Gly Pro Gly
570                 575                 580                 585

GGA ATG TTC AGA GGT GGC CGT GGT GGA GAC AGA GGT GGC TTC CGT GGT     1827
Gly Met Phe Arg Gly Gly Arg Gly Gly Asp Arg Gly Gly Phe Arg Gly
                590                 595                 600

GGC CGG GGC ATG GAC CGA GGT GGC TTT GGT GGA GGA AGA CGA GGT GGC     1875
Gly Arg Gly Met Asp Arg Gly Gly Phe Gly Gly Gly Arg Arg Gly Gly
            605                 610                 615

CCT GGG GGG CCC CCT GGA CCT TTG ATG GAA CAG ATG GGA GGA AGA AGA     1923
Pro Gly Gly Pro Pro Gly Pro Leu Met Glu Gln Met Gly Gly Arg Arg
        620                 625                 630

GGA GGA CGT GGA GGA CCT GGA AAA ATG GAT AAA GGC GAG CAC CGT CAG     1971
Gly Gly Arg Gly Gly Pro Gly Lys Met Asp Lys Gly Glu His Arg Gln
    635                 640                 645

GAG CGC AGA GAT CGG CCC TAC TAGATGCAGA GACCCCGCAG AGCTGCATTG        2022
Glu Arg Arg Asp Arg Pro Tyr
650                 655

ACTACCAGAT TTATTTTTTA AACCAGAAAA TGTTTTAAAT TTATAATTCC ATATTTATAA   2082

TGTTGGCCAC AACATTATGA TTATTCCTTG TCTGTACTTT AGTATTTTTC ACCATTTGTG   2142

AAGAAACATT AAAACAAGTT AAATGGTAGT GTGCGGAGTT TTTTTTTCTT CCTTCTTTTA   2202

AAAATGGTTG TTTAAGACTT TAACAATGGG AACCCCTTGT GAGCATGCTC AGTATCATTG   2262

TGGAGAACCA AGAGGGCCTC TTAACTGTAA CAATGTTCAT GGTTGTGATG TTTTTTTTTT   2322

TTTTTTAAAA TAAAATTCCA AATGTTTAAT AAAAAAAAAA AAAAAAAA               2371

(2) INFORMATION FOR SEQ ID NO:2:

(i) SEQUENCE CHARACTERISTICS:
        (A) LENGTH: 656 amino acids
        (B) TYPE: amino acid
        (D) TOPOLOGY: linear (ii) MOLECULE TYPE: protein (xi) SEQUENCE DESCRIPTION: SEQ ID NO:2:

Met Ala Ser Thr Asp Tyr Ser Thr Tyr Ser Gln Ala Ala Ala Gln Gln
1               5                   10                  15

Gly Tyr Ser Ala Tyr Thr Ala Gln Pro Thr Gln Gly Tyr Ala Gln Thr
                20                  25                  30

Thr Gln Ala Tyr Gly Gln Gln Ser Tyr Gly Thr Tyr Gly Gln Pro Thr
            35                  40                  45

Asp Val Ser Tyr Thr Gln Ala Gln Thr Thr Ala Thr Tyr Gly Gln Thr
        50                  55                  60

Ala Tyr Ala Thr Ser Tyr Gly Gln Pro Pro Thr Gly Tyr Thr Thr Pro
65                  70                  75                  80

Thr Ala Pro Gln Ala Tyr Ser Gln Pro Val Gln Gly Tyr Gly Thr Gly
                85                  90                  95

Ala Tyr Asp Thr Thr Thr Ala Thr Val Thr Thr Thr Gln Ala Ser Tyr
            100                 105                 110

Ala Ala Gln Ser Ala Tyr Gly Thr Gln Pro Ala Tyr Pro Ala Tyr Gly
        115                 120                 125

Gln Gln Pro Ala Ala Thr Ala Pro Thr Arg Pro Gln Asp Gly Asn Lys
    130                 135                 140
```

```
Pro Thr Glu Thr Ser Gln Pro Gln Ser Ser Thr Gly Gly Tyr Asn Gln
145                 150                 155                 160

Pro Ser Leu Gly Tyr Gly Gln Ser Asn Tyr Ser Tyr Pro Gln Val Pro
            165                 170                 175

Gly Ser Tyr Pro Met Gln Pro Val Thr Ala Pro Pro Ser Tyr Pro Pro
            180                 185                 190

Thr Ser Tyr Ser Ser Thr Gln Pro Thr Ser Tyr Asp Gln Ser Ser Tyr
            195                 200                 205

Ser Gln Gln Asn Thr Tyr Gly Gln Pro Ser Ser Tyr Gly Gln Gln Ser
210                 215                 220

Ser Tyr Gly Gln Gln Ser Ser Tyr Gly Gln Gln Pro Pro Thr Ser Tyr
225                 230                 235                 240

Pro Pro Gln Thr Gly Ser Tyr Ser Gln Ala Pro Ser Gln Tyr Ser Gln
                245                 250                 255

Gln Ser Ser Ser Tyr Gly Gln Gln Ser Ser Phe Arg Gln Asp His Pro
            260                 265                 270

Ser Ser Met Gly Val Tyr Gly Gln Glu Ser Gly Gly Phe Ser Gly Pro
            275                 280                 285

Gly Glu Asn Arg Ser Met Ser Gly Pro Asp Asn Arg Gly Arg Gly Arg
290                 295                 300

Gly Gly Phe Asp Arg Gly Gly Met Ser Arg Gly Arg Gly Gly Gly Gly
305                 310                 315                 320

Arg Gly Gly Met Gly Ser Ala Gly Glu Arg Gly Gly Phe Asn Lys Pro
                325                 330                 335

Gly Gly Pro Met Asp Glu Gly Pro Asp Leu Asp Leu Gly Pro Pro Val
            340                 345                 350

Asp Pro Asp Glu Asp Ser Asp Asn Ser Ala Ile Tyr Val Gln Gly Leu
            355                 360                 365

Asn Asp Ser Val Thr Leu Asp Asp Leu Ala Asp Phe Phe Lys Gln Cys
370                 375                 380

Gly Val Val Lys Met Asn Lys Arg Thr Gly Gln Pro Met Ile His Ile
385                 390                 395                 400

Tyr Leu Asp Lys Glu Thr Gly Lys Pro Lys Gly Asp Ala Thr Val Ser
            405                 410                 415

Tyr Glu Asp Pro Pro Thr Ala Lys Ala Ala Val Glu Trp Phe Asp Gly
            420                 425                 430

Lys Asp Phe Gln Gly Ser Lys Leu Lys Val Ser Leu Ala Arg Lys Lys
            435                 440                 445

Pro Pro Met Asn Ser Met Arg Gly Gly Leu Pro Pro Arg Glu Gly Arg
450                 455                 460

Gly Met Pro Pro Pro Leu Arg Gly Gly Pro Gly Gly Pro Gly Gly Pro
465                 470                 475                 480

Gly Gly Pro Met Gly Arg Met Gly Gly Arg Gly Gly Asp Arg Gly Gly
                485                 490                 495

Phe Pro Pro Arg Gly Pro Arg Gly Ser Arg Gly Asn Pro Ser Gly Gly
            500                 505                 510

Gly Asn Val Gln His Arg Ala Gly Asp Trp Gln Cys Pro Asn Pro Gly
            515                 520                 525

Cys Gly Asn Gln Asn Phe Ala Trp Arg Thr Glu Cys Asn Gln Cys Lys
530                 535                 540

Ala Pro Lys Pro Glu Gly Phe Leu Pro Pro Pro Phe Pro Pro Pro Gly
545                 550                 555                 560

Gly Asp Arg Gly Arg Gly Gly Pro Gly Gly Met Arg Gly Gly Arg Gly
```

```
                            565                 570                 575
Gly Leu Met Asp Arg Gly Gly Pro Gly Gly Met Phe Arg Gly Gly Arg
                580                 585                 590

Gly Gly Asp Arg Gly Gly Phe Arg Gly Arg Gly Met Asp Arg Gly
            595                 600                 605

Gly Phe Gly Gly Gly Arg Arg Gly Gly Pro Gly Pro Pro Gly Pro
        610                 615                 620

Leu Met Glu Gln Met Gly Gly Arg Arg Gly Gly Arg Gly Pro Gly
625                 630                 635                 640

Lys Met Asp Lys Gly Glu His Arg Gln Glu Arg Arg Asp Arg Pro Tyr
                645                 650                 655

(2) INFORMATION FOR SEQ ID NO:3:

(i) SEQUENCE CHARACTERISTICS:
        (A) LENGTH: 2938 base pairs
        (B) TYPE: nucleic acid
        (C) STRANDEDNESS: double
        (D) TOPOLOGY: linear (ix) FEATURE:
         (A) NAME/KEY: CDS
         (B) LOCATION: 143..1498

(xi) SEQUENCE DESCRIPTION: SEQ ID NO:3:

GGAGGGCGCT CGCAGGGGGC ACGCAGGGAG GGCCCAGGGC GCCAGGGAGG CCGCGCCGGG    60

CTAATCCGAA GGGGCTGCGA GGTCAGGCTG TAACCGGGTC AATGTGTGGA ATATTGGGGG   120

GCTCGGCTGC AGACTTGGCC AA ATG GAC GGG ACT ATT AAG GAG GCT CTG TCG   172
                         Met Asp Gly Thr Ile Lys Glu Ala Leu Ser
                          1               5                  10

GTG GTG AGC GAC GAC CAG TCC CTC TTT GAC TCA GCG TAC GGA GCG GCA   220
Val Val Ser Asp Asp Gln Ser Leu Phe Asp Ser Ala Tyr Gly Ala Ala
             15                  20                  25

GCC CAT CTC CCC AAG GCC GAC ATG ACT GCC TCG GGG AGT CCT GAC TAC   268
Ala His Leu Pro Lys Ala Asp Met Thr Ala Ser Gly Ser Pro Asp Tyr
         30                  35                  40

GGG CAG CCC CAC AAG ATC AAC CCC CTC CCA CCA CAG CAG GAG TGG ATC   316
Gly Gln Pro His Lys Ile Asn Pro Leu Pro Pro Gln Gln Glu Trp Ile
     45                  50                  55

AAT CAG CCA GTG AGG GTC AAC GTC AAG CGG GAG TAT GAC CAC ATG AAT   364
Asn Gln Pro Val Arg Val Asn Val Lys Arg Glu Tyr Asp His Met Asn
 60                  65                  70

GGA TCC AGG GAG TCT CCG GTG GAC TGC AGC GTT AGC AAA TGC AGC AAG   412
Gly Ser Arg Glu Ser Pro Val Asp Cys Ser Val Ser Lys Cys Ser Lys
 75                  80                  85                  90

CTG GTG GGC GGA GGC GAG TCC AAC CCC ATG AAC TAC AAC AGC TAT ATG   460
Leu Val Gly Gly Gly Glu Ser Asn Pro Met Asn Tyr Asn Ser Tyr Met
                 95                 100                 105

GAC GAG AAG AAT GGC CCC CCT CCT CCC AAC ATG ACC ACC AAC GAG AGG   508
Asp Glu Lys Asn Gly Pro Pro Pro Pro Asn Met Thr Thr Asn Glu Arg
        110                 115                 120

AGA GTC ATC GTC CCC GCA GAC CCC ACA CTG TGG ACA CAG GAG CAT GTG   556
Arg Val Ile Val Pro Ala Asp Pro Thr Leu Trp Thr Gln Glu His Val
            125                 130                 135

AGG CAA TGG CTG GAG TGG GCC ATA AAG GAG TAT AGC TTG ATG GAG ATC   604
Arg Gln Trp Leu Glu Trp Ala Ile Lys Glu Tyr Ser Leu Met Glu Ile
140                 145                 150

GAC ACA TCC TTT TTC CAG AAC ATG GAT GGC AAG GAA CTG TGT AAA ATG   652
Asp Thr Ser Phe Phe Gln Asn Met Asp Gly Lys Glu Leu Cys Lys Met
155                 160                 165                 170
```

-continued

| | |
|---|---|
| AAC AAG GAG GAC TTC CTC CGC GCC ACC ACC CTC TAC AAC ACG GAA GTG<br>Asn Lys Glu Asp Phe Leu Arg Ala Thr Thr Leu Tyr Asn Thr Glu Val<br>                   175                        180                        185 | 700 |
| CTG TTG TCA CAC CTC AGT TAC CTC AGG GAA AGT TCA CTG CTG GCC TAT<br>Leu Leu Ser His Leu Ser Tyr Leu Arg Glu Ser Ser Leu Leu Ala Tyr<br>                   190                        195                        200 | 748 |
| AAT ACA ACC TCC CAC ACC GAC CAA TCC TCA CGA TTG AGT GTC AAA GAA<br>Asn Thr Thr Ser His Thr Asp Gln Ser Ser Arg Leu Ser Val Lys Glu<br>                   205                        210                        215 | 796 |
| GAC CCT TCT TAT GAC TCA GTC AGA AGA GGA GCA TGG GGC AAT AAC ATG<br>Asp Pro Ser Tyr Asp Ser Val Arg Arg Gly Ala Trp Gly Asn Asn Met<br>                   220                        225                        230 | 844 |
| AAT TCT GGC CTC AAC AAA AGT CCT CCC CTT GGA GGG GCA CAA ACG ATC<br>Asn Ser Gly Leu Asn Lys Ser Pro Pro Leu Gly Gly Ala Gln Thr Ile<br>235                   240                        245                        250 | 892 |
| AGT AAG AAT ACA GAG CAA CGG CCC CAG CCA GAT CCG TAT CAG ATC CTG<br>Ser Lys Asn Thr Glu Gln Arg Pro Gln Pro Asp Pro Tyr Gln Ile Leu<br>                   255                        260                        265 | 940 |
| GGC CCG ACC AGC AGT CGC CTA GCC AAC CCT GGA AGC GGG CAG ATC CAG<br>Gly Pro Thr Ser Ser Arg Leu Ala Asn Pro Gly Ser Gly Gln Ile Gln<br>                   270                        275                        280 | 988 |
| CTG TGG CAA TTC CTC CTG GAG CTG CTC TCC GAC AGC GCC AAC GCC AGC<br>Leu Trp Gln Phe Leu Leu Glu Leu Leu Ser Asp Ser Ala Asn Ala Ser<br>                   285                        290                        295 | 1036 |
| TGT ATC ACC TGG GAG GGG ACC AAC GGG GAG TTC AAA ATG ACG GAC CCC<br>Cys Ile Thr Trp Glu Gly Thr Asn Gly Glu Phe Lys Met Thr Asp Pro<br>                   300                        305                        310 | 1084 |
| GAT GAG GTG GCC AGG CGC TGG GGC GAG CGG AAA AGC AAG CCC AAC ATG<br>Asp Glu Val Ala Arg Arg Trp Gly Glu Arg Lys Ser Lys Pro Asn Met<br>315                   320                        325                        330 | 1132 |
| AAT TAC GAC AAG CTG AGC CGG GCC CTC CGT TAT TAC TAT GAT AAA AAC<br>Asn Tyr Asp Lys Leu Ser Arg Ala Leu Arg Tyr Tyr Tyr Asp Lys Asn<br>                   335                        340                        345 | 1180 |
| ATT ATG ACC AAA GTG CAC GGC AAA AGA TAT GCT TAC AAA TTT GAC TTC<br>Ile Met Thr Lys Val His Gly Lys Arg Tyr Ala Tyr Lys Phe Asp Phe<br>                   350                        355                        360 | 1228 |
| CAC GGC ATT GCC CAG GCT CTG CAG CCA CAT CCG ACC GAG TCG TCC ATG<br>His Gly Ile Ala Gln Ala Leu Gln Pro His Pro Thr Glu Ser Ser Met<br>                   365                        370                        375 | 1276 |
| TAC AAG TAC CCT TCT GAC ATC TCC TAC ATG CCT TCC TAC CAT GCC CAC<br>Tyr Lys Tyr Pro Ser Asp Ile Ser Tyr Met Pro Ser Tyr His Ala His<br>                   380                        385                        390 | 1324 |
| CAG CAG AAG GTG AAC TTT GTC CCT CCC CAT CCA TCC TCC ATG CCT GTC<br>Gln Gln Lys Val Asn Phe Val Pro Pro His Pro Ser Ser Met Pro Val<br>395                   400                        405                        410 | 1372 |
| ACT TCC TCC AGC TTC TTT GGA GCC GCA TCA CAA TAC TGG ACC TCC CCC<br>Thr Ser Ser Ser Phe Phe Gly Ala Ala Ser Gln Tyr Trp Thr Ser Pro<br>                   415                        420                        425 | 1420 |
| ACG GGG GGA ATC TAC CCC AAC CCC AAC GTC CCC CGC CAT CCT AAC ACC<br>Thr Gly Gly Ile Tyr Pro Asn Pro Asn Val Pro Arg His Pro Asn Thr<br>                   430                        435                        440 | 1468 |
| CAC GTG CCT TCA CAC TTA GGC AGC TAC TAC TAGAAGCTTA CTCATCAGTG<br>His Val Pro Ser His Leu Gly Ser Tyr Tyr<br>                   445                        450 | 1518 |
| GCCTTCTAGC TGAAGCCCAT CCTGCACACT TACTGGATGC TTTGGACTCA ACAGGACATA | 1578 |
| TGTGGCCTTG AAGGGAAGAC AAAACTGGAT GTTCTTTCTT GTTGGATAGA ACCTTTGTAT | 1638 |
| TTGTTCTTTA AAAACATTTT TTTTAATGTT GGTAACTTTT GCTTCCTCTA CCTGAACAAA | 1698 |
| GAGATGAATA ATTCCATGGG CCAGTATGCC AGTTTGAATT CTCAGTCTCC TAGCATCTTG | 1758 |

```
TGAGTTGCAT ATTAAGATTA CTGGAATGGT TAAGTCATGG TTCTGAGAAA GAAGCTGTAC         1818

GTTTTCTTTA TGTTTTTATG ACCAAAGCAG TTCTTGTCA ATACACGGGG TTCAGTATGA          1878

CACAGAATCA TGGACTTAAC CCGTCATGTT CTGGTTTGAG ATTTAGTGAC AAATAGAGGT         1938

GGGAAGCTTA TAATCTAATT TTAGGAGGAC CAAATTCAGT GGATGGCAAC TGGAACATTG         1998

ATTGTAAGGC CAGTGAAGTT TTCACCCAAC TGGAATTTGA TGGAAAGAAG GTTTGTGTGT         2058

TTAAGACGCC AAGGGCATTG CAGAATCCCT CTCAGTGGAC AGTATGCACT CAGCTGACCA         2118

CTCTCTCTAG AAATAGTCAA GATATGAACT AAGAAATTTT AATGCAAATA CATACATTCC         2178

TGAAAGACGG GGAATTAAAT TACTAATTTT TTTTTTTTTT TAAATGATGA CAGTGGTCCC        2238

AGAACTTGGA AAAGTTGTAG GGATTTCTAA ACTCAAGCAG ATTCGCAAGT GCTGTGCGCT         2298

TGTCAGACCA TCAGACCAGG GCCAACCAAT CAGAAGGCAA CTTACTGTAT AAATTATGCA         2358

GAGTTATTTT CCTATATCTC ACAGTATTAA AAATAAATAA TTAAAAATTA AGAATAAATA         2418

AACGAGTTGA CCTCGGTCAC AAAAGCAGTT TTACTATCGA ATCAATCGCT GTTATTTTTT         2478

TTAATGTAAT TTGTACATCT TTTTTCAATC TGTACATTTG GGCTGTCTGT ATGTTTTTAT         2538

AGCTGGTTTT TAAAAAGCAT AATATGCCTA TAGCTGAAAA GGAAACAGGG CTGTTTAAGT         2598

CACTGACTTA TGAGAAAGCA AAGCACTGGT ACAGTTATTT AACAGGCATA CACAAGCAGG         2658

GAAAGATAAT CCATTTAGAT CTTTAATGCT TTGGAAATGC GTGTAACAGT ACTGCAATAA         2718

TCACAGCTCT GGGAAAAACA ACGAAACTTT CCCTTGTGGA GAGGAGGGAT TTTCCTGCTC         2778

TATATAAGCA ACATATTTTT AGACATTAAA ATATATATAA TTTTGCAGGT AATTGTTGAC         2838

TTTTTTAACT ATATTAAGCG TTAAGCTGAC AACTGTCAAA GAAGACCATG TTGTAAAATA         2898

ATTTGACTAA ATAAATGGTT CCTTCTCTCA AAAAAAAAA                               2938

(2) INFORMATION FOR SEQ ID NO:4:

(i) SEQUENCE CHARACTERISTICS:
        (A) LENGTH: 452 amino acids
        (B) TYPE: amino acid
        (D) TOPOLOGY: linear (ii) MOLECULE TYPE: protein (xi) SEQUENCE DESCRIPTION: SEQ ID NO:4:

Met Asp Gly Thr Ile Lys Glu Ala Leu Ser Val Val Ser Asp Asp Gln
 1               5                  10                  15

Ser Leu Phe Asp Ser Ala Tyr Gly Ala Ala His Leu Pro Lys Ala
            20                  25                  30

Asp Met Thr Ala Ser Gly Ser Pro Asp Tyr Gly Gln Pro His Lys Ile
        35                  40                  45

Asn Pro Leu Pro Pro Gln Gln Glu Trp Ile Asn Gln Pro Val Arg Val
    50                  55                  60

Asn Val Lys Arg Glu Tyr Asp His Met Asn Gly Ser Arg Glu Ser Pro
65                  70                  75                  80

Val Asp Cys Ser Val Ser Lys Cys Ser Lys Leu Val Gly Gly Gly Glu
                85                  90                  95

Ser Asn Pro Met Asn Tyr Asn Ser Tyr Met Asp Glu Lys Asn Gly Pro
            100                 105                 110

Pro Pro Pro Asn Met Thr Thr Asn Glu Arg Arg Val Ile Val Pro Ala
        115                 120                 125

Asp Pro Thr Leu Trp Thr Gln Glu His Val Arg Gln Trp Leu Glu Trp
    130                 135                 140

Ala Ile Lys Glu Tyr Ser Leu Met Glu Ile Asp Thr Ser Phe Phe Gln
```

```
                145                 150                 155                 160
Asn Met Asp Gly Lys Glu Leu Cys Lys Met Asn Lys Glu Asp Phe Leu
                165                 170                 175

Arg Ala Thr Thr Leu Tyr Asn Thr Glu Val Leu Leu Ser His Leu Ser
            180                 185                 190

Tyr Leu Arg Glu Ser Ser Leu Leu Ala Tyr Asn Thr Thr Ser His Thr
        195                 200                 205

Asp Gln Ser Ser Arg Leu Ser Val Lys Glu Asp Pro Ser Tyr Asp Ser
    210                 215                 220

Val Arg Arg Gly Ala Trp Gly Asn Asn Met Asn Ser Gly Leu Asn Lys
225                 230                 235                 240

Ser Pro Pro Leu Gly Gly Ala Gln Thr Ile Ser Lys Asn Thr Glu Gln
            245                 250                 255

Arg Pro Gln Pro Asp Pro Tyr Gln Ile Leu Gly Pro Thr Ser Ser Arg
        260                 265                 270

Leu Ala Asn Pro Gly Ser Gly Gln Ile Gln Leu Trp Gln Phe Leu Leu
    275                 280                 285

Glu Leu Leu Ser Asp Ser Ala Asn Ala Ser Cys Ile Thr Trp Glu Gly
290                 295                 300

Thr Asn Gly Glu Phe Lys Met Thr Asp Pro Asp Glu Val Ala Arg Arg
305                 310                 315                 320

Trp Gly Glu Arg Lys Ser Lys Pro Asn Met Asn Tyr Asp Lys Leu Ser
            325                 330                 335

Arg Ala Leu Arg Tyr Tyr Tyr Asp Lys Asn Ile Met Thr Lys Val His
        340                 345                 350

Gly Lys Arg Tyr Ala Tyr Lys Phe Asp Phe His Gly Ile Ala Gln Ala
    355                 360                 365

Leu Gln Pro His Pro Thr Glu Ser Ser Met Tyr Lys Tyr Pro Ser Asp
    370                 375                 380

Ile Ser Tyr Met Pro Ser Tyr His Ala His Gln Gln Lys Val Asn Phe
385                 390                 395                 400

Val Pro Pro His Pro Ser Ser Met Pro Val Thr Ser Ser Ser Phe Phe
            405                 410                 415

Gly Ala Ala Ser Gln Tyr Trp Thr Ser Pro Thr Gly Gly Ile Tyr Pro
        420                 425                 430

Asn Pro Asn Val Pro Arg His Pro Asn Thr His Val Pro Ser His Leu
    435                 440                 445

Gly Ser Tyr Tyr
    450

(2) INFORMATION FOR SEQ ID NO:5:

(i) SEQUENCE CHARACTERISTICS:
        (A) LENGTH: 328 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..327

(xi) SEQUENCE DESCRIPTION: SEQ ID NO:5:

TCC TAC AGC CAA GCT CCA AGT CAA TAT AGC CAA CAG AGC AGC AGC TAC        48
Ser Tyr Ser Gln Ala Pro Ser Gln Tyr Ser Gln Gln Ser Ser Ser Tyr
  1               5                  10                  15

GGG CAG CAG AAC CCT TCT TAT GAC TCA GTC AGA AGA GGA GCT TGG GGC        96
Gly Gln Gln Asn Pro Ser Tyr Asp Ser Val Arg Arg Gly Ala Trp Gly
```

```
                20                    25                      30
AAT AAC ATG AAT TCT GGC CTC AAC AAA AGT CCT CCC CTT GGA GGG GCA     144
Asn Asn Met Asn Ser Gly Leu Asn Lys Ser Pro Pro Leu Gly Gly Ala
            35                  40                  45

CAA ACG ATC AGT AAG AAT ACA GAG CAA CGG CCC CAG CCA GAT CCG TAT     192
Gln Thr Ile Ser Lys Asn Thr Glu Gln Arg Pro Gln Pro Asp Pro Tyr
        50                  55                  60

CAG ATC CTG GGC CCG ACC AGC AGT CGC CTA GCC AAC CCT GGA AGC GGG     240
Gln Ile Leu Gly Pro Thr Ser Ser Arg Leu Ala Asn Pro Gly Ser Gly
65                  70                  75                  80

CAG ATC CAG CTG TGG CAA TTC CTC CTG GAG CTG CTC TCC GAC AGC GCC     288
Gln Ile Gln Leu Trp Gln Phe Leu Leu Glu Leu Leu Ser Asp Ser Ala
                85                  90                  95

AAC GCC AGC TGT ATC ACC TGG GAG GGG ACC AAC GGG GAG T               328
Asn Ala Ser Cys Ile Thr Trp Glu Gly Thr Asn Gly Glu
            100                 105
```

(2) INFORMATION FOR SEQ ID NO:6:

(i) SEQUENCE CHARACTERISTICS:
       (A) LENGTH: 109 amino acids
       (B) TYPE: amino acid
       (D) TOPOLOGY: linear (ii) MOLECULE TYPE: protein (xi) SEQUENCE DESCRIPTION: SEQ ID NO:6:

```
Ser Tyr Ser Gln Ala Pro Ser Gln Tyr Ser Gln Gln Ser Ser Tyr
1               5                   10                  15

Gly Gln Gln Asn Pro Ser Tyr Asp Ser Val Arg Arg Gly Ala Trp Gly
                20                  25                  30

Asn Asn Met Asn Ser Gly Leu Asn Lys Ser Pro Pro Leu Gly Gly Ala
            35                  40                  45

Gln Thr Ile Ser Lys Asn Thr Glu Gln Arg Pro Gln Pro Asp Pro Tyr
        50                  55                  60

Gln Ile Leu Gly Pro Thr Ser Ser Arg Leu Ala Asn Pro Gly Ser Gly
65                  70                  75                  80

Gln Ile Gln Leu Trp Gln Phe Leu Leu Glu Leu Leu Ser Asp Ser Ala
                85                  90                  95

Asn Ala Ser Cys Ile Thr Trp Glu Gly Thr Asn Gly Glu
            100                 105
```

(2) INFORMATION FOR SEQ ID NO:7:

(i) SEQUENCE CHARACTERISTICS:
       (A) LENGTH: 86 amino acids
       (B) TYPE: amino acid
       (D) TOPOLOGY: linear (xi) SEQUENCE DESCRIPTION: SEQ ID NO:7:

```
Ile Tyr Val Gln Gly Leu Asn Asp Ser Val Thr Leu Asp Asp Leu Ala
1               5                   10                  15

Asp Phe Phe Lys Gln Cys Gly Val Val Lys Met Asn Lys Arg Thr Gly
                20                  25                  30

Gln Pro Met Ile His Ile Tyr Leu Asp Lys Glu Thr Gly Lys Pro Lys
            35                  40                  45

Gly Asp Ala Thr Val Ser Tyr Glu Asp Pro Pro Thr Ala Lys Ala Ala
        50                  55                  60

Val Glu Trp Phe Asp Gly Lys Asp Phe Gln Gly Ser Lys Leu Lys Val
65                  70                  75                  80
```

Ser Leu Ala Arg Lys Lys
              85

(2) INFORMATION FOR SEQ ID NO:8:

(i) SEQUENCE CHARACTERISTICS:
        (A) LENGTH: 86 amino acids
        (B) TYPE: amino acid
        (D) TOPOLOGY: linear (xi) SEQUENCE DESCRIPTION: SEQ ID NO:8:

Ile Phe Val Ser Gly Met Asp Pro Ser Thr Thr Glu Gln Asp Ile Glu
1               5                   10                  15

Thr His Phe Gly Ala Ile Gly Ile Ile Lys Lys Asp Lys Arg Thr Met
                20                  25                  30

Lys Pro Lys Ile Trp Leu Tyr Lys Asn Lys Glu Thr Gly Ala Ser Lys
            35                  40                  45

Gly Glu Ala Thr Val Thr Tyr Asp Asp Thr Asn Ala Ala Gln Ser Ala
        50                  55                  60

Ile Glu Trp Phe Asp Gly Arg Xaa Phe Asn Gly Asn Ala Ile Lys Val
65                  70                  75                  80

Ser Leu Ala Gln Arg Gln
              85

(2) INFORMATION FOR SEQ ID NO:9:

(i) SEQUENCE CHARACTERISTICS:
         (A) LENGTH: 72 amino acids
         (B) TYPE: amino acid
         (D) TOPOLOGY: linear (xi) SEQUENCE DESCRIPTION: SEQ ID NO:9:

Leu Phe Val Lys Gly Leu Ser Glu Asp Thr Thr Glu Glu Thr Leu Lys
1               5                   10                  15

Glu Ser Phe Asp Gly Ser Val Arg Ala Arg Ile Val Thr Asp Arg Glu
                20                  25                  30

Thr Gly Ser Ser Lys Gly Phe Gly Phe Val Asp Phe Asn Ser Glu Glu
            35                  40                  45

Asp Ala Lys Glu Ala Met Glu Asp Gly Glu Ile Asp Gly Asn Lys Val
        50                  55                  60

Thr Leu Asp Trp Ala Lys Pro Lys
65                  70

(2) INFORMATION FOR SEQ ID NO:10:

(i) SEQUENCE CHARACTERISTICS:
         (A) LENGTH: 78 amino acids
         (B) TYPE: amino acid
         (D) TOPOLOGY: linear (xi) SEQUENCE DESCRIPTION: SEQ ID NO:10:

Leu Phe Val Ala Arg Val Asn Tyr Asp Thr Thr Glu Ser Lys Leu Arg
1               5                   10                  15

Arg Glu Phe Glu Val Tyr Gly Pro Ile Lys Arg Ile His Met Val Tyr
                20                  25                  30

Ser Lys Arg Ser Gly Lys Pro Arg Gly Tyr Ala Phe Ile Glu Tyr Glu
            35                  40                  45

His Glu Arg Asp Met His Ser Ala Tyr Lys His Ala Asp Gly Lys Lys
        50                  55                  60

Ile Asp Gly Arg Arg Val Leu Val Asp Val Glu Arg Gly Arg
65                  70                  75

(2) INFORMATION FOR SEQ ID NO:11:

(i) SEQUENCE CHARACTERISTICS:
        (A) LENGTH: 74 amino acids
        (B) TYPE: amino acid
        (D) TOPOLOGY: linear (xi) SEQUENCE DESCRIPTION: SEQ ID NO:11:

```
Val Tyr Ile Lys Asn Phe Gly Glu Asp Met Asp Asp Glu Arg Leu Lys
1               5                  10                  15

Asp Leu Phe Gly Pro Ala Leu Ser Val Lys Val Met Thr Asp Glu Ser
            20                  25                  30

Gly Lys Ser Lys Gly Phe Gly Phe Val Ser Phe Glu Arg His Glu Asp
            35                  40                  45

Ala Gln Lys Ala Val Asp Glu Met Asn Gly Lys Glu Leu Asn Gly Lys
        50                  55                  60

Gln Ile Tyr Val Gly Arg Ala Gln Lys Lys
65                  70
```

(2) INFORMATION FOR SEQ ID NO:12:

(i) SEQUENCE CHARACTERISTICS:
        (A) LENGTH: 77 amino acids
        (B) TYPE: amino acid
        (D) TOPOLOGY: linear (xi) SEQUENCE DESCRIPTION: SEQ ID NO:12:

```
Ile Phe Val Gly Gly Ile Lys Glu Asp Thr Glu Glu His His Leu Arg
1               5                  10                  15

Asp Tyr Phe Glu Gln Tyr Gly Lys Ile Glu Val Ile Glu Ile Met Thr
            20                  25                  30

Asp Arg Gly Ser Gly Lys Lys Arg Gly Phe Ala Phe Val Thr Phe Asp
            35                  40                  45

Asp His Asp Ser Val Asp Lys Ile Val Ile Gln Lys Tyr His Thr Val
        50                  55                  60

Asn Gly His Asn Cys Glu Val Arg Lys Ala Leu Ser Lys
65                  70                  75
```

(2) INFORMATION FOR SEQ ID NO:13:

(i) SEQUENCE CHARACTERISTICS:
        (A) LENGTH: 77 amino acids
        (B) TYPE: amino acid
        (D) TOPOLOGY: linear (xi) SEQUENCE DESCRIPTION: SEQ ID NO:13:

```
Leu Phe Val Gly Gly Ile Lys Glu Asp Thr Glu Glu His His Leu Arg
1               5                  10                  15

Asp Tyr Phe Glu Glu Tyr Gly Lys Ile Asp Thr Ile Glu Ile Ile Thr
            20                  25                  30

Asp Arg Gln Ser Gly Lys Lys Arg Gly Phe Gly Phe Val Thr Phe Asp
            35                  40                  45

Asp His Asp Pro Val Asp Lys Ile Val Leu Gln Lys Tyr His Thr Ile
        50                  55                  60

Asn Gly His Asn Ala Glu Val Arg Lys Ala Leu Ser Arg
65                  70                  75
```

(2) INFORMATION FOR SEQ ID NO:14:

(i) SEQUENCE CHARACTERISTICS:

(A) LENGTH: 67 base pairs
          (B) TYPE: nucleic acid
          (C) STRANDEDNESS: double
          (D) TOPOLOGY: linear (xi) SEQUENCE DESCRIPTION: SEQ ID NO:14:

GAGAACGAGG AGGAAGGAGA GAAAATGGCG TCCACGGGTG AGTATGGTGG AACTGCGGTC        60

GCGCCGG                                                                 67

(2) INFORMATION FOR SEQ ID NO:15:

(i) SEQUENCE CHARACTERISTICS:
          (A) LENGTH: 41 base pairs
          (B) TYPE: nucleic acid
          (C) STRANDEDNESS: double
          (D) TOPOLOGY: linear (xi) SEQUENCE DESCRIPTION: SEQ ID NO:15:

ACACTATTTT TCCTCCTTGT TTTCCTCTAG ATTACAGTAC C                            41

(2) INFORMATION FOR SEQ ID NO:16:

(i) SEQUENCE CHARACTERISTICS:
          (A) LENGTH: 41 base pairs
          (B) TYPE: nucleic acid
          (C) STRANDEDNESS: double
          (D) TOPOLOGY: linear (xi) SEQUENCE DESCRIPTION: SEQ ID NO:16:

GCGCAGCAGG GGTAAGTCAG TCTTTTATAA CCGTATTTTG T                            41

(2) INFORMATION FOR SEQ ID NO:17:

(i) SEQUENCE CHARACTERISTICS:
          (A) LENGTH: 40 base pairs
          (B) TYPE: nucleic acid
          (C) STRANDEDNESS: double
          (D) TOPOLOGY: linear (xi) SEQUENCE DESCRIPTION: SEQ ID NO:17:

TTCAAGTTAT TGCATTTAAT TCTTTTGCAG CTACAGTGCT                              40

(2) INFORMATION FOR SEQ ID NO:18:

(i) SEQUENCE CHARACTERISTICS:
          (A) LENGTH: 39 base pairs
          (B) TYPE: nucleic acid
          (C) STRANDEDNESS: double
          (D) TOPOLOGY: linear (xi) SEQUENCE DESCRIPTION: SEQ ID NO:18:

ACCACCCAGG TAATCTTTAA AATAATTACA TGTAGCTGC                               39

(2) INFORMATION FOR SEQ ID NO:19:

(i) SEQUENCE CHARACTERISTICS:
          (A) LENGTH: 39 base pairs
          (B) TYPE: nucleic acid
          (C) STRANDEDNESS: double
          (D) TOPOLOGY: linear (xi) SEQUENCE DESCRIPTION: SEQ ID NO:19:

GTTCTTGCAT TCGGTTTTTT TTTGGAGCAG GCATATGGG                               39

(2) INFORMATION FOR SEQ ID NO:20:

(i) SEQUENCE CHARACTERISTICS:

(A) LENGTH: 40 base pairs
          (B) TYPE: nucleic acid
          (C) STRANDEDNESS: double
          (D) TOPOLOGY: linear (xi) SEQUENCE DESCRIPTION: SEQ ID NO:20:

CCTCCCACTG GTAAGGCCTG CCTTGGAGAG ATTTTTGGGT					40

(2) INFORMATION FOR SEQ ID NO:21:

(i) SEQUENCE CHARACTERISTICS:
          (A) LENGTH: 41 base pairs
          (B) TYPE: nucleic acid
          (C) STRANDEDNESS: double
          (D) TOPOLOGY: linear (xi) SEQUENCE DESCRIPTION: SEQ ID NO:21:

GAAATCTGAT GCAGCTCCCC TTTGGTCTAG GTTATACTAC T					41

(2) INFORMATION FOR SEQ ID NO:22:

(i) SEQUENCE CHARACTERISTICS:
          (A) LENGTH: 41 base pairs
          (B) TYPE: nucleic acid
          (C) STRANDEDNESS: double
          (D) TOPOLOGY: linear (xi) SEQUENCE DESCRIPTION: SEQ ID NO:22:

GCACCTACAA GGTAAGGCCA TGGTGTCCTT AATGCGTCAG T					41

(2) INFORMATION FOR SEQ ID NO:23:

(i) SEQUENCE CHARACTERISTICS:
          (A) LENGTH: 40 base pairs
          (B) TYPE: nucleic acid
          (C) STRANDEDNESS: double
          (D) TOPOLOGY: linear (xi) SEQUENCE DESCRIPTION: SEQ ID NO:23:

TTTAATTTTA TTTATTATTT CTCCTCTTAG ACCGCAGGAT					40

(2) INFORMATION FOR SEQ ID NO:24:

(i) SEQUENCE CHARACTERISTICS:
          (A) LENGTH: 41 base pairs
          (B) TYPE: nucleic acid
          (C) STRANDEDNESS: double
          (D) TOPOLOGY: linear (xi) SEQUENCE DESCRIPTION: SEQ ID NO:24:

CCTCCTACCA GGTCAGTCTA CTTTTTGTGG CAAAACAAAA A					41

(2) INFORMATION FOR SEQ ID NO:25:

(i) SEQUENCE CHARACTERISTICS:
          (A) LENGTH: 40 base pairs
          (B) TYPE: nucleic acid
          (C) STRANDEDNESS: double
          (D) TOPOLOGY: linear (xi) SEQUENCE DESCRIPTION: SEQ ID NO:25:

TTTTTTTTTT CTCCTTCCTC TCTCTTTCAG CTATTCCTCT					40

(2) INFORMATION FOR SEQ ID NO:26:

(i) SEQUENCE CHARACTERISTICS:
          (A) LENGTH: 40 base pairs
          (B) TYPE: nucleic acid (C) STRANDEDNESS: double
        (D) TOPOLOGY: linear (xi) SEQUENCE DESCRIPTION: SEQ ID NO:26:

GGGCAGCAGA GTGAGTTGCT AAGAGAGAAA ACCAAATAAG                         40

(2) INFORMATION FOR SEQ ID NO:27:

(i) SEQUENCE CHARACTERISTICS:
        (A) LENGTH: 41 base pairs
        (B) TYPE: nucleic acid
        (C) STRANDEDNESS: double
        (D) TOPOLOGY: linear (xi) SEQUENCE DESCRIPTION: SEQ ID NO:27:

CATGGCTTAC AGATGTGACT CTTTCCTCAG GTTCATTCCG A                       41

(2) INFORMATION FOR SEQ ID NO:28:

(i) SEQUENCE CHARACTERISTICS:
        (A) LENGTH: 38 base pairs
        (B) TYPE: nucleic acid
        (C) STRANDEDNESS: double
        (D) TOPOLOGY: linear (xi) SEQUENCE DESCRIPTION: SEQ ID NO:28:

GGAATGGGGT AAGAGCAAAC CTTTTCTCCT TTTACCTA                           38

(2) INFORMATION FOR SEQ ID NO:29:

(i) SEQUENCE CHARACTERISTICS:
        (A) LENGTH: 40 base pairs
        (B) TYPE: nucleic acid
        (C) STRANDEDNESS: double
        (D) TOPOLOGY: linear (xi) SEQUENCE DESCRIPTION: SEQ ID NO:29:

AAGGCCTTCA TTTCTCGTTT ATCCCCCCAG CAGCGCTGGA                         40

(2) INFORMATION FOR SEQ ID NO:30:

(i) SEQUENCE CHARACTERISTICS:
        (A) LENGTH: 40 base pairs
        (B) TYPE: nucleic acid
        (C) STRANDEDNESS: double
        (D) TOPOLOGY: linear (xi) SEQUENCE DESCRIPTION: SEQ ID NO:30:

AAGCCTGGTG GTAAGTTTTT GAGTATTACC ATAGATAGTG                         40

(2) INFORMATION FOR SEQ ID NO:31:

(i) SEQUENCE CHARACTERISTICS:
        (A) LENGTH: 41 base pairs
        (B) TYPE: nucleic acid
        (C) STRANDEDNESS: double
        (D) TOPOLOGY: linear (xi) SEQUENCE DESCRIPTION: SEQ ID NO:31:

ATATTTTATA TGATCTTTCC TGGTTGGCAG GACCCATGGA T                       41

(2) INFORMATION FOR SEQ ID NO:32:

(i) SEQUENCE CHARACTERISTICS:
        (A) LENGTH: 40 base pairs
        (B) TYPE: nucleic acid
        (C) STRANDEDNESS: double
        (D) TOPOLOGY: linear (xi) SEQUENCE DESCRIPTION: SEQ ID NO:32:

CTTGATCTAG GTAAGTTGAA TTCCTAGTTG TGCCTTCCAT                              40

(2) INFORMATION FOR SEQ ID NO:33:

(i) SEQUENCE CHARACTERISTICS:
        (A) LENGTH: 41 base pairs
        (B) TYPE: nucleic acid
        (C) STRANDEDNESS: double
        (D) TOPOLOGY: linear (xi) SEQUENCE DESCRIPTION: SEQ ID NO:33:

ATAATTCTCC TGTCTTGTTG TCTCTGAAAG GCCCACCTGT A                            41

(2) INFORMATION FOR SEQ ID NO:34:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (xi) SEQUENCE DESCRIPTION: SEQ ID NO:34:

GGGGTTGTTA AGGTCAGTAA AAGCATAACC AGGTCATCTG GC                           42

(2) INFORMATION FOR SEQ ID NO:35:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (xi) SEQUENCE DESCRIPTION: SEQ ID NO:35:

TCATGCCTAA CTATGCTATT CTTTGTCTAG ATGAACAAGA GA                           42

(2) INFORMATION FOR SEQ ID NO:36:

(i) SEQUENCE CHARACTERISTICS:
        (A) LENGTH: 43 base pairs
        (B) TYPE: nucleic acid
        (C) STRANDEDNESS: double
        (D) TOPOLOGY: linear (xi) SEQUENCE DESCRIPTION: SEQ ID NO:36:

GAATGGTTTG ATGGTGAGAT GTACTCACTG GCATTCTTAA TCT                          43

(2) INFORMATION FOR SEQ ID NO:37:

(i) SEQUENCE CHARACTERISTICS:
        (A) LENGTH: 41 base pairs
        (B) TYPE: nucleic acid
        (C) STRANDEDNESS: double
        (D) TOPOLOGY: linear (xi) SEQUENCE DESCRIPTION: SEQ ID NO:37:

AGTAATTGAT GTTCTGTTGT CTTGTTCCAG GGAAAGATTT T                            41

(2) INFORMATION FOR SEQ ID NO:38:

(i) SEQUENCE CHARACTERISTICS:
        (A) LENGTH: 43 base pairs
        (B) TYPE: nucleic acid
        (C) STRANDEDNESS: double
        (D) TOPOLOGY: linear (xi) SEQUENCE DESCRIPTION: SEQ ID NO:38:

```
CCACTCCGTG GAGGTACTTT TACTGAGCTC CTATGTTGCA TTA                              43

(2) INFORMATION FOR SEQ ID NO:39:

(i) SEQUENCE CHARACTERISTICS:
         (A) LENGTH: 44 base pairs
         (B) TYPE: nucleic acid
         (C) STRANDEDNESS: double
         (D) TOPOLOGY: linear (xi) SEQUENCE DESCRIPTION: SEQ ID NO:39:

ATTTGCTGTT TCTTGTTGTT CTTGTTGTAG GTCCAGGAGG CCCA                             44

(2) INFORMATION FOR SEQ ID NO:40:

(i) SEQUENCE CHARACTERISTICS:
         (A) LENGTH: 38 base pairs
         (B) TYPE: nucleic acid
         (C) STRANDEDNESS: double
         (D) TOPOLOGY: linear (xi) SEQUENCE DESCRIPTION: SEQ ID NO:40:

CCCAATCCGT ATGTACTTGT CTGGGAAAAT TGATACCC                                    38

(2) INFORMATION FOR SEQ ID NO:41:

(i) SEQUENCE CHARACTERISTICS:
         (A) LENGTH: 43 base pairs
         (B) TYPE: nucleic acid
         (C) STRANDEDNESS: double
         (D) TOPOLOGY: linear (xi) SEQUENCE DESCRIPTION: SEQ ID NO:41:

TGATTTCTGC TGTGATGTAA TTGTATGCAG GGGTTGTGGA AAC                              43

(2) INFORMATION FOR SEQ ID NO:42:

(i) SEQUENCE CHARACTERISTICS:
         (A) LENGTH: 37 base pairs
         (B) TYPE: nucleic acid
         (C) STRANDEDNESS: double
         (D) TOPOLOGY: linear (xi) SEQUENCE DESCRIPTION: SEQ ID NO:42:

CCCCCGGGTA GGTGCAGGTT TCATGAGTGT CCCCTCA                                     37

(2) INFORMATION FOR SEQ ID NO:43:

(i) SEQUENCE CHARACTERISTICS:
         (A) LENGTH: 41 base pairs
         (B) TYPE: nucleic acid
         (C) STRANDEDNESS: double
         (D) TOPOLOGY: linear (xi) SEQUENCE DESCRIPTION: SEQ ID NO:43:

ACTGCTTTCG CCCTGCTATT CTCACCTTAG GTGGTGATCG T                                41

(2) INFORMATION FOR SEQ ID NO:44:

(i) SEQUENCE CHARACTERISTICS:
         (A) LENGTH: 38 base pairs
         (B) TYPE: nucleic acid
         (C) STRANDEDNESS: double
         (D) TOPOLOGY: linear (xi) SEQUENCE DESCRIPTION: SEQ ID NO:44:

ATGGATAAGT AAGTGCTGGT GAAAAGCAGC TGTGGGCC                                    38
```

(2) INFORMATION FOR SEQ ID NO:45:

(i) SEQUENCE CHARACTERISTICS:
        (A) LENGTH: 425 base pairs
        (B) TYPE: nucleic acid
        (C) STRANDEDNESS: double
        (D) TOPOLOGY: linear (xi) SEQUENCE DESCRIPTION: SEQ ID NO:45:

```
TCTAACCGAA GGGCCCTCTT TACCTTGCAG AGGCGAGCAC CGTCAGGAGC GCAGAGATCG    60

GCCCTACTAG ATGCAGAGAC CCCGCAGAGC TGCATTGACT ACCAGATTTA TTTTTTAAAC   120

CAGAAAATGT TTTAAATTTA TAATTCCATA TTTATAATGT TGGCCACAAC ATTATGATTA   180

TTCCTTGTCT GTACTTTAGT ATTTTTCACC ATTTGTGAAG AAACATTAAA ACAAGTTAAA   240

TGGTAGTGTG CGGAGTTTTT TTTTCTTCCT TCTTTTAAAA ATGGTTGTTT AAGACTTTAA   300

CAATGGGAAC CCCTTGTGAG CATGCTCAGT ATCATTGTGG AGAACCAAGA GGGCCTCTTA   360

ACTGTAACAA TGTTCATGGT TGTGATGTTT TTTTTTTTTT TTTAAATAAA ATTCCAAATG   420

TTTAT                                                              425
```

(2) INFORMATION FOR SEQ ID NO:46:

(i) SEQUENCE CHARACTERISTICS:
        (A) LENGTH: 69 base pairs
        (B) TYPE: nucleic acid
        (C) STRANDEDNESS: double
        (D) TOPOLOGY: linear (xi) SEQUENCE DESCRIPTION: SEQ ID NO:46:

```
CTCGGCTGCA GACTTGGCCA AATGGACGGG ACTATTAAGG TAAGCGGCGG GGCAACGGAC    60

GCGGGCGGC                                                           69
```

(2) INFORMATION FOR SEQ ID NO:47:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (xi) SEQUENCE DESCRIPTION: SEQ ID NO:47:

```
ACCCGGGGAT CCTCTAGAGT CGACCTGCAG GAGGCTCTGT CG                       42
```

(2) INFORMATION FOR SEQ ID NO:48:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (xi) SEQUENCE DESCRIPTION: SEQ ID NO:48:

```
GAATGGATCC AGGTAAGCTC ACCAGGCCTG TGCAGGATTG GG                       42
```

(2) INFORMATION FOR SEQ ID NO:49:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (xi) SEQUENCE DESCRIPTION: SEQ ID NO:49:

```
CCTTGGGCTT TGCCCCCTC CTCACTTTAG GGAGTCTCCG GT                               42

(2) INFORMATION FOR SEQ ID NO:50:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (xi) SEQUENCE DESCRIPTION: SEQ ID NO:50:

TCGTCCCCGC AGGTAATTCG AGAACCAGGC TGCCTGGGCG CC                              42

(2) INFORMATION FOR SEQ ID NO:51:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (xi) SEQUENCE DESCRIPTION: SEQ ID NO:51:

TCCTTGCTAA CAACGTCTTC TCCTCTGCAG ACCCCACACT GT                              42

(2) INFORMATION FOR SEQ ID NO:52:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (xi) SEQUENCE DESCRIPTION: SEQ ID NO:52:

ACCTCAGGGA AGTAAGTGC CGCCCAAGTA CCCAGGGCTG GG                               42

(2) INFORMATION FOR SEQ ID NO:53:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (xi) SEQUENCE DESCRIPTION: SEQ ID NO:53:

GTTATAACCT GTTTATGTTT TGCCTCTCAG GTTCACTGCT GG                              42

(2) INFORMATION FOR SEQ ID NO:54:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (xi) SEQUENCE DESCRIPTION: SEQ ID NO:54:

GTGTCAAAGA AGGTAAGTTT GTTCTTTTGT GCACTTAAAA TT                              42

(2) INFORMATION FOR SEQ ID NO:55:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (xi) SEQUENCE DESCRIPTION: SEQ ID NO:55:

AATGTACCCC TATTTGTTAT TGTTCATTAG ACCCTTCTTA TG                              42
```

(2) INFORMATION FOR SEQ ID NO:56:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (xi) SEQUENCE DESCRIPTION: SEQ ID NO:56:

GCCTCAACAA AAGTAAGTAA ATGTTTTATA GTTCTTTGGA GG      42

(2) INFORMATION FOR SEQ ID NO:57:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (xi) SEQUENCE DESCRIPTION: SEQ ID NO:57:

CTCACTGCAT TTCTTTCCCT CTTGCCACAG GTCCTCCCCT TG      42

(2) INFORMATION FOR SEQ ID NO:58:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (xi) SEQUENCE DESCRIPTION: SEQ ID NO:58:

GGCCCCAGCC AGGTACCTGC CCAGGATATG TAATCTCTCC TT      42

(2) INFORMATION FOR SEQ ID NO:59:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (xi) SEQUENCE DESCRIPTION: SEQ ID NO:59:

TGAAGCAAAT TTCCTTTTTT ATTTCCTTAG ATCCGTATCA GA      42

(2) INFORMATION FOR SEQ ID NO:60:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (xi) SEQUENCE DESCRIPTION: SEQ ID NO:60:

TAGCCAACCC TGGTGAGTTT ACCTTGGCCT GCAAGCCTTT TT      42

(2) INFORMATION FOR SEQ ID NO:61:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (xi) SEQUENCE DESCRIPTION: SEQ ID NO:61:

TGTTCTCTCC CGTTTCCTCA CGGCGTGCAG GAAGCGGGCA GA      42

(2) INFORMATION FOR SEQ ID NO:62:

(i) SEQUENCE CHARACTERISTICS:
            (A) LENGTH: 42 base pairs
            (B) TYPE: nucleic acid
            (C) STRANDEDNESS: double
            (D) TOPOLOGY: linear (xi) SEQUENCE DESCRIPTION: SEQ ID NO:62:

AGCTACTACT AGAAGCTTAC TCATCAGTGG CCTTCTAGCT GA                          42

(2) INFORMATION FOR SEQ ID NO:63:

(i) SEQUENCE CHARACTERISTICS:
            (A) LENGTH: 33 base pairs
            (B) TYPE: nucleic acid
            (C) STRANDEDNESS: double
            (D) TOPOLOGY: linear (ix) FEATURE:
            (A) NAME/KEY: CDS
            (B) LOCATION: 1..33

(xi) SEQUENCE DESCRIPTION: SEQ ID NO:63:

AGC TAC GGG CAG CAG AAT CCG TAT CAG ATC CTG                             33
Ser Tyr Gly Gln Gln Asn Pro Tyr Gln Ile Leu
 1               5                  10

(2) INFORMATION FOR SEQ ID NO:64:

(i) SEQUENCE CHARACTERISTICS:
            (A) LENGTH: 11 amino acids
            (B) TYPE: amino acid
            (D) TOPOLOGY: linear (ii) MOLECULE TYPE: protein (xi) SEQUENCE DESCRIPTION: SEQ ID NO:64:

Ser Tyr Gly Gln Gln Asn Pro Tyr Gln Ile Leu
 1               5                  10

(2) INFORMATION FOR SEQ ID NO:65:

(i) SEQUENCE CHARACTERISTICS:
            (A) LENGTH: 33 base pairs
            (B) TYPE: nucleic acid
            (C) STRANDEDNESS: double
            (D) TOPOLOGY: linear (ix) FEATURE:
            (A) NAME/KEY: CDS
            (B) LOCATION: 1..33

(xi) SEQUENCE DESCRIPTION: SEQ ID NO:65:

AGC TAC GGG CAG CAG AAC CCT TCT TAT GAC TCA                             33
Ser Tyr Gly Gln Gln Asn Pro Ser Tyr Asp Ser
 1               5                  10

(2) INFORMATION FOR SEQ ID NO:66:

(i) SEQUENCE CHARACTERISTICS:
            (A) LENGTH: 11 amino acids
            (B) TYPE: amino acid
            (D) TOPOLOGY: linear (ii) MOLECULE TYPE: protein (xi) SEQUENCE DESCRIPTION: SEQ ID NO:66:

Ser Tyr Gly Gln Gln Asn Pro Ser Tyr Asp Ser
 1               5                  10

-continued (2) INFORMATION FOR SEQ ID NO:67:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..33

(xi) SEQUENCE DESCRIPTION: SEQ ID NO:67:

```
AGC TAC GGG CAG CAG AGT TCA CTG CTG GCC TAT          33
Ser Tyr Gly Gln Gln Ser Ser Leu Leu Ala Tyr
 1               5                  10
```

(2) INFORMATION FOR SEQ ID NO:68:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO:68:

```
Ser Tyr Gly Gln Gln Ser Ser Leu Leu Ala Tyr
 1               5                  10
```

(2) INFORMATION FOR SEQ ID NO:69:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..33

(xi) SEQUENCE DESCRIPTION: SEQ ID NO:69:

```
TTC AAT AAG CCT GGT GGT CCT CCC CTT GGA GGG          33
Phe Asn Lys Pro Gly Gly Pro Pro Leu Gly Gly
 1               5                  10
```

(2) INFORMATION FOR SEQ ID NO:70:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO:70:

```
Phe Asn Lys Pro Gly Gly Pro Pro Leu Gly Gly
 1               5                  10
```

(2) INFORMATION FOR SEQ ID NO:71:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..33

```
    (xi) SEQUENCE DESCRIPTION: SEQ ID NO:71:

TTC AAT AAG CCT GGT GAC CCC ACA CTG TGG ACA                              33
Phe Asn Lys Pro Gly Asp Pro Thr Leu Trp Thr
 1               5                  10

(2) INFORMATION FOR SEQ ID NO:72:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO:72:

Phe Asn Lys Pro Gly Asp Pro Thr Leu Trp Thr
 1               5                  10

(2) INFORMATION FOR SEQ ID NO:73:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..33

(xi) SEQUENCE DESCRIPTION: SEQ ID NO:73:

CCA GAT CTT GAT CTA GAT CCG TAT CAG ATC CTG                              33
Pro Asp Leu Asp Leu Asp Pro Tyr Gln Ile Leu
 1               5                  10

(2) INFORMATION FOR SEQ ID NO:74:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO:74:

Pro Asp Leu Asp Leu Asp Pro Tyr Gln Ile Leu
 1               5                  10

(2) INFORMATION FOR SEQ ID NO:75:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..33

(xi) SEQUENCE DESCRIPTION: SEQ ID NO:75:

CCA GAT CTT GAT CTA GAC CCT TCT TAT GAC TCA                              33
Pro Asp Leu Asp Leu Asp Pro Ser Tyr Asp Ser
 1               5                  10

(2) INFORMATION FOR SEQ ID NO:76:

(i) SEQUENCE CHARACTERISTICS:
        (A) LENGTH: 11 amino acids
        (B) TYPE: amino acid
```

(D) TOPOLOGY: linear (ii) MOLECULE TYPE: protein (xi) SEQUENCE DESCRIPTION: SEQ ID NO:76:

Pro Asp Leu Asp Leu Asp Pro Ser Tyr Asp Ser
 1               5                  10

(2) INFORMATION FOR SEQ ID NO:77:

(i) SEQUENCE CHARACTERISTICS:
          (A) LENGTH: 33 base pairs
          (B) TYPE: nucleic acid
          (C) STRANDEDNESS: double
          (D) TOPOLOGY: linear (ix) FEATURE:
          (A) NAME/KEY: CDS
          (B) LOCATION: 1..33

(xi) SEQUENCE DESCRIPTION: SEQ ID NO:77:

CCA GAT CTT GAT CTA GGT TCA CTG CTG GCC TAT                               33
Pro Asp Leu Asp Leu Gly Ser Leu Leu Ala Tyr
 1               5                  10

(2) INFORMATION FOR SEQ ID NO:78:

(i) SEQUENCE CHARACTERISTICS:
          (A) LENGTH: 11 amino acids
          (B) TYPE: amino acid
          (D) TOPOLOGY: linear (ii) MOLECULE TYPE: protein (xi) SEQUENCE DESCRIPTION: SEQ ID NO:78:

Pro Asp Leu Asp Leu Gly Ser Leu Leu Ala Tyr
 1               5                  10

(2) INFORMATION FOR SEQ ID NO:79:

(i) SEQUENCE CHARACTERISTICS:
          (A) LENGTH: 78 base pairs
          (B) TYPE: nucleic acid
          (C) STRANDEDNESS: double
          (D) TOPOLOGY: linear (ix) FEATURE:
          (A) NAME/KEY: CDS
          (B) LOCATION: 1..78

(xi) SEQUENCE DESCRIPTION: SEQ ID NO:79:

GGA CGC GGT GGA ATG GGG TTC CTG GAG CTT AGG ATG TGT GAT GCA GAA           48
Gly Arg Gly Gly Met Gly Phe Leu Glu Leu Arg Met Cys Asp Ala Glu
 1               5                  10                  15

GAA GTC TGG AAA GGT CCT CCC CTT GGA GGG                                   78
Glu Val Trp Lys Gly Pro Pro Leu Gly Gly
                20                  25

(2) INFORMATION FOR SEQ ID NO:80:

(i) SEQUENCE CHARACTERISTICS:
          (A) LENGTH: 26 amino acids
          (B) TYPE: amino acid
          (D) TOPOLOGY: linear (ii) MOLECULE TYPE: protein (xi) SEQUENCE DESCRIPTION: SEQ ID NO:80:

Gly Arg Gly Gly Met Gly Phe Leu Glu Leu Arg Met Cys Asp Ala Glu
 1               5                  10                  15

```
Glu Val Trp Lys Gly Pro Pro Leu Gly Gly
         20                  25
```

(2) INFORMATION FOR SEQ ID NO:81:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..33

(xi) SEQUENCE DESCRIPTION: SEQ ID NO:81:

```
AGC TAC GGG CAG CAG AAC CCT TCT TAT GAC TCA                    33
Ser Tyr Gly Gln Gln Asn Pro Ser Tyr Asp Ser
 1               5                  10
```

(2) INFORMATION FOR SEQ ID NO:82:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO:82:

```
Ser Tyr Gly Gln Gln Asn Pro Ser Tyr Asp Ser
 1               5                  10
```

(2) INFORMATION FOR SEQ ID NO:83:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..27

(xi) SEQUENCE DESCRIPTION: SEQ ID NO:83:

```
GGA CGC GGT GGA ATG GGA CCC TTC TTA TGA                        30
Gly Arg Gly Gly Met Gly Pro Phe Leu
 1               5
```

(2) INFORMATION FOR SEQ ID NO:84:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO:84:

```
Gly Arg Gly Gly Met Gly Pro Phe Leu
 1               5
```

(2) INFORMATION FOR SEQ ID NO:85:

(i) SEQUENCE CHARACTERISTICS:
        (A) LENGTH: 33 base pairs
        (B) TYPE: nucleic acid
        (C) STRANDEDNESS: double
        (D) TOPOLOGY: linear

```
    (ix) FEATURE:
         (A) NAME/KEY: CDS
         (B) LOCATION: 1..33

(xi) SEQUENCE DESCRIPTION: SEQ ID NO:85:

TTC AAT AAG CCT GGT GGT CCT CCC CTT GGA GGG                        33
Phe Asn Lys Pro Gly Gly Pro Pro Leu Gly Gly
 1               5                  10

(2) INFORMATION FOR SEQ ID NO:86:

(i) SEQUENCE CHARACTERISTICS:
         (A) LENGTH: 11 amino acids
         (B) TYPE: amino acid
         (D) TOPOLOGY: linear (ii) MOLECULE TYPE: protein (xi) SEQUENCE DESCRIPTION: SEQ ID NO:86:

Phe Asn Lys Pro Gly Gly Pro Pro Leu Gly Gly
 1               5                  10

(2) INFORMATION FOR SEQ ID NO:87:

(i) SEQUENCE CHARACTERISTICS:
         (A) LENGTH: 51 base pairs
         (B) TYPE: nucleic acid
         (C) STRANDEDNESS: double
         (D) TOPOLOGY: linear (ix) FEATURE:
         (A) NAME/KEY: CDS
         (B) LOCATION: 1..48

(xi) SEQUENCE DESCRIPTION: SEQ ID NO:87:

GGA CGC GGT GGA ATG GGG TCC TCC CCT TGG AGG GGC ACA AAC GAT CAG    48
Gly Arg Gly Gly Met Gly Ser Ser Pro Trp Arg Gly Thr Asn Asp Gln
 1               5                  10                  15

TAA                                                                51

(2) INFORMATION FOR SEQ ID NO:88:

(i) SEQUENCE CHARACTERISTICS:
         (A) LENGTH: 16 amino acids
         (B) TYPE: amino acid
         (D) TOPOLOGY: linear (ii) MOLECULE TYPE: protein (xi) SEQUENCE DESCRIPTION: SEQ ID NO:88:

Gly Arg Gly Gly Met Gly Ser Ser Pro Trp Arg Gly Thr Asn Asp Gln
 1               5                  10                  15

(2) INFORMATION FOR SEQ ID NO:89:

(i) SEQUENCE CHARACTERISTICS:
         (A) LENGTH: 51 base pairs
         (B) TYPE: nucleic acid
         (C) STRANDEDNESS: double
         (D) TOPOLOGY: linear (ix) FEATURE:
         (A) NAME/KEY: CDS
         (B) LOCATION: 1..48

(xi) SEQUENCE DESCRIPTION: SEQ ID NO:89:

GGA CGC GGT GGA ATG GGG TCC TCC CCT TGG AGG GGC ACA AAC GAT CAG    48
Gly Arg Gly Gly Met Gly Ser Ser Pro Trp Arg Gly Thr Asn Asp Gln
 1               5                  10                  15
```

```
TAA                                                          51

(2) INFORMATION FOR SEQ ID NO:90:

(i) SEQUENCE CHARACTERISTICS:
        (A) LENGTH: 16 amino acids
        (B) TYPE: amino acid
        (D) TOPOLOGY: linear (ii) MOLECULE TYPE: protein (xi) SEQUENCE DESCRIPTION: SEQ ID NO:90:

Gly Arg Gly Gly Met Gly Ser Ser Pro Trp Arg Gly Thr Asn Asp Gln
 1               5                  10                  15

(2) INFORMATION FOR SEQ ID NO:91:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..27

(xi) SEQUENCE DESCRIPTION: SEQ ID NO:91:

GGA CGC GGT GGA ATG GGG ACC CAT GGA TGA                       30
Gly Arg Gly Gly Met Gly Thr His Gly
 1               5

(2) INFORMATION FOR SEQ ID NO:92:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO:92:

Gly Arg Gly Gly Met Gly Thr His Gly
 1               5

(2) INFORMATION FOR SEQ ID NO:93:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..33

(xi) SEQUENCE DESCRIPTION: SEQ ID NO:93:

CCA GAT CTT GAT CTA GAT CCG TAT CAG ATC CTG                   33
Pro Asp Leu Asp Leu Asp Pro Tyr Gln Ile Leu
 1               5                  10

(2) INFORMATION FOR SEQ ID NO:94:

(i) SEQUENCE CHARACTERISTICS:
        (A) LENGTH: 11 amino acids
        (B) TYPE: amino acid
        (D) TOPOLOGY: linear (ii) MOLECULE TYPE: protein
```

(xi) SEQUENCE DESCRIPTION: SEQ ID NO:94:

Pro Asp Leu Asp Leu Asp Pro Tyr Gln Ile Leu
 1               5                  10

(2) INFORMATION FOR SEQ ID NO:95:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..27

(xi) SEQUENCE DESCRIPTION: SEQ ID NO:95:

```
GGA CGC GGT GGA ATG GGG ACC CAT GGA TGA                          30
Gly Arg Gly Gly Met Gly Thr His Gly
 1               5
```

(2) INFORMATION FOR SEQ ID NO:96:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO:96:

Gly Arg Gly Gly Met Gly Thr His Gly
 1               5

(2) INFORMATION FOR SEQ ID NO:97:

(i) SEQUENCE CHARACTERISTICS:
        (A) LENGTH: 833 base pairs
        (B) TYPE: nucleic acid
        (C) STRANDEDNESS: double
        (D) TOPOLOGY: linear (xi) SEQUENCE DESCRIPTION: SEQ ID NO:97:

```
CTGCAGAGCG CGCCCAGGCA ACCCCGAAAG GCCGGTCGGG GACCCCGGCT GGGAGTCAGG     60
ACTCTAGCTC CCGGGCGCGA CCCGAGAACC CTGAATCCAT TCCGCGCACA CCCGGCACGC    120
GTGACCCCTG CCGACCGGCT GGCGCGCCAC CCATTCCCCG CGGCCCGCGG ATTAGTCAGC    180
AGTTGTTCTA GTCCGGGTCC CTTCCCCCAG CCCTCCCGCC GATCTCCGTC TCCCTGCAGG    240
GCCGACTCTT CAGCGACCGT CCCTAGAGCC AGCGGACGGA ACCATTCCAA ACAGCCTAGT    300
CTCGTGCTGA GAGCCTCTCC GGTTTCACGC TGAGACCCGC TCACCCCGC TCTGGCCCCT    360
TAGATGCTAT TTTGGCCCGA GTGTCACGTC GGGCGCTCTT TAGAGAGGAC TGGGACAAGA    420
GTTGCGGACG CGAAGAACGA GTAAGCGGTG GTTCATCCCT CCTGACCCCA CCCCGTGGC    480
CTGGCCCGAT GGTCGCGCCC GGGGTTGCGA GATTTGCGCC TGCGCAGTGC GGCGCCTAGA    540
GGGAAAGCGA GAGGGAGACG GACGTTGAGA GAACGAGGAG GAAGGAGAGA AAATGGCGTC    600
CACGGGTGAG TATGGTGGAA CTGCGGTCGC GCCGGCGGTA GCCGGAACGC CCAAACTGGG    660
GGTCGTTCGT CTCTGGGCTT GGCTGGGAAG ACTGAGTGGA GTTGCCGAGA GGGGGTTGAG    720
GCACCCGCCG CGGCCCGACG AGCTCGGGGA TCCGCATTCC TCTCCCCTCC CCAACCGGG    780
CGGGCCGGTT CTGGAATCTT CCCGCGCCCT CGCGCGCGGG GGGCTTTGCT TTT           833
```

(2) INFORMATION FOR SEQ ID NO:98:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..33

(xi) SEQUENCE DESCRIPTION: SEQ ID NO:98:

```
AGC TAC GGG CAG CAG AGC AGT GGC CAG ATC CAG                    33
Ser Tyr Gly Gln Gln Ser Ser Gly Gln Ile Gln
 1               5                  10
```

(2) INFORMATION FOR SEQ ID NO:99:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO:99:

```
Ser Tyr Gly Gln Gln Ser Ser Gly Gln Ile Gln
 1               5                  10
```

(2) INFORMATION FOR SEQ ID NO:100:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..33

(xi) SEQUENCE DESCRIPTION: SEQ ID NO:100:

```
AGC TAC GGG CAG CAG AAT CCT TAT CAG ATT CTT                    33
Ser Tyr Gly Gln Gln Asn Pro Tyr Gln Ile Leu
 1               5                  10
```

(2) INFORMATION FOR SEQ ID NO:101:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO:101:

```
Ser Tyr Gly Gln Gln Asn Pro Tyr Gln Ile Leu
 1               5                  10
```

(2) INFORMATION FOR SEQ ID NO:102:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..33

(xi) SEQUENCE DESCRIPTION: SEQ ID NO:102:

```
AGC TAC GGG CAG CAG AAT TTA CCA TAT GAG CCC                    33
Ser Tyr Gly Gln Gln Asn Leu Pro Tyr Glu Pro
 1               5                  10
```

(2) INFORMATION FOR SEQ ID NO:103:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO:103:

```
Ser Tyr Gly Gln Gln Asn Leu Pro Tyr Glu Pro
 1               5                  10
```

(2) INFORMATION FOR SEQ ID NO:104:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..33

(xi) SEQUENCE DESCRIPTION: SEQ ID NO:104:

```
CCA GAT CTT GAT CTA GAT TTA CCA TAT GAG CCC                    33
Pro Asp Leu Asp Leu Asp Leu Pro Tyr Glu Pro
 1               5                  10
```

(2) INFORMATION FOR SEQ ID NO:105:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO:105:

```
Pro Asp Leu Asp Leu Asp Leu Pro Tyr Glu Pro
 1               5                  10
```

(2) INFORMATION FOR SEQ ID NO:106:

(i) SEQUENCE CHARACTERISTICS:
        (A) LENGTH: 954 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..885

(xi) SEQUENCE DESCRIPTION: SEQ ID NO:106:

```
CCC ACT AGT TAC CCA CCC CAA ACT GGA TCC TAC AGC CAA GCT CCA AGT       48
Pro Thr Ser Tyr Pro Pro Gln Thr Gly Ser Tyr Ser Gln Ala Pro Ser
 1               5                  10                  15

CAA TAT AGC CAA CAG AGC AGC AGC TAC GGG CAG CAG AGT TCA TTC CGA       96
Gln Tyr Ser Gln Gln Ser Ser Ser Tyr Gly Gln Gln Ser Ser Phe Arg
                20                  25                  30

CAG GAC CAC CCC AGT AGC ATG GGT GTT TAT GGG CAG GAG TCT GGA GGA      144
Gln Asp His Pro Ser Ser Met Gly Val Tyr Gly Gln Glu Ser Gly Gly
```

```
                    35                     40                      45
TTT TCC GGA CCA GGA GAG AAC CGG AGC ATG AGT GGC CCT GAT AAC CGG     192
Phe Ser Gly Pro Gly Glu Asn Arg Ser Met Ser Gly Pro Asp Asn Arg
         50                      55                      60

GGC AGG GGA AGA GGG GGA TTT GAT CGT GGA GGC ATG AGC AGA GGT GGG     240
Gly Arg Gly Arg Gly Gly Phe Asp Arg Gly Gly Met Ser Arg Gly Gly
 65                      70                      75                  80

CGG GGA GGA GGA CGC GGT GGA ATG GGA AAA ATT TTG AAA GAC TTA TCT     288
Arg Gly Gly Gly Arg Gly Gly Met Gly Lys Ile Leu Lys Asp Leu Ser
                 85                      90                      95

TCT GAA GAT ACA CGG GGC AGA AAA GGA GAC GGA GAA AAT TCT GGA GTT     336
Ser Glu Asp Thr Arg Gly Arg Lys Gly Asp Gly Glu Asn Ser Gly Val
             100                     105                     110

TCT GCT GCT GTC ACT TCT ATG TCT GTT CCA ACT CCC ATC TAT CAG ACT     384
Ser Ala Ala Val Thr Ser Met Ser Val Pro Thr Pro Ile Tyr Gln Thr
         115                     120                     125

AGC AGC GGA CAG TAC ATT GCC ATT GCC CCA AAT GGA GCC TTA CAG TTG     432
Ser Ser Gly Gln Tyr Ile Ala Ile Ala Pro Asn Gly Ala Leu Gln Leu
 130                     135                     140

GCA AGT CCA GGC ACA GAT GGA GTA CAG GGA CTT CAG ACA TTA ACC ATG     480
Ala Ser Pro Gly Thr Asp Gly Val Gln Gly Leu Gln Thr Leu Thr Met
145                     150                     155                 160

ACA AAT TCA GGC AGT ACT CAG CAA GGT ACA ACT ATT CTT CAG TAT GCA     528
Thr Asn Ser Gly Ser Thr Gln Gln Gly Thr Thr Ile Leu Gln Tyr Ala
                165                     170                     175

CAG ACC TCT GAT GGA CAG CAG ATA CTT GTG CCC AGC AAT CAG GTG GTC     576
Gln Thr Ser Asp Gly Gln Gln Ile Leu Val Pro Ser Asn Gln Val Val
            180                     185                     190

GTA CAA ACT GCA TCA GGA GAT ATG CAA ACA TAT CAG ATC CGA ACT ACA     624
Val Gln Thr Ala Ser Gly Asp Met Gln Thr Tyr Gln Ile Arg Thr Thr
        195                     200                     205

CCT TCA GCT ACT TCT CTG CCA CAA ACT GTG GTG ATG ACA TCT CCT GTG     672
Pro Ser Ala Thr Ser Leu Pro Gln Thr Val Val Met Thr Ser Pro Val
    210                     215                     220

ACT CTC ACC TCT CAG ACA ACT AAG ACA GAT GAC CCC CAA TTG AAA AGA     720
Thr Leu Thr Ser Gln Thr Thr Lys Thr Asp Asp Pro Gln Leu Lys Arg
225                     230                     235                 240

GAA ATA AGG TTA ATG AAA AAC AGA GAA GCT GCT CGA GAA TGT CGC AGA     768
Glu Ile Arg Leu Met Lys Asn Arg Glu Ala Ala Arg Glu Cys Arg Arg
                245                     250                     255

AAG AAG AAA GAA TAT GTG AAA TGC CTG GAA AAC CGA GTT GCA GTC CTG     816
Lys Lys Lys Glu Tyr Val Lys Cys Leu Glu Asn Arg Val Ala Val Leu
            260                     265                     270

GAA AAT CAA AAT AAA ACT CTA ATA GAA GAG TTA AAA ACT TTG AAG GAT     864
Glu Asn Gln Asn Lys Thr Leu Ile Glu Glu Leu Lys Thr Leu Lys Asp
        275                     280                     285

CTT TAT TCC AAT AAA AGT GTT TGATTCCTAA GAAAGAAAAT ATTTTTGTGG        915
Leu Tyr Ser Asn Lys Ser Val
        290                     295

ACATGCATAA AAATTAAATG GATTTCCTAG TGGAGTTTT                           954

(2) INFORMATION FOR SEQ ID NO:107:

(i) SEQUENCE CHARACTERISTICS:
        (A) LENGTH: 295 amino acids
        (B) TYPE: amino acid
        (D) TOPOLOGY: linear (ii) MOLECULE TYPE: protein (xi) SEQUENCE DESCRIPTION: SEQ ID NO:107:
```

```
Pro Thr Ser Tyr Pro Gln Thr Gly Ser Tyr Ser Gln Ala Pro Ser
  1               5                  10                 15

Gln Tyr Ser Gln Gln Ser Ser Tyr Gly Gln Gln Ser Ser Phe Arg
             20                  25                  30

Gln Asp His Pro Ser Ser Met Gly Val Tyr Gly Gln Glu Ser Gly Gly
             35                  40                  45

Phe Ser Gly Pro Gly Glu Asn Arg Ser Met Ser Gly Pro Asp Asn Arg
 50                  55                  60

Gly Arg Gly Arg Gly Gly Phe Asp Arg Gly Gly Met Ser Arg Gly Gly
 65                  70                  75                  80

Arg Gly Gly Arg Gly Gly Met Gly Lys Ile Leu Lys Asp Leu Ser
                 85                  90                  95

Ser Glu Asp Thr Arg Gly Arg Lys Gly Asp Gly Glu Asn Ser Gly Val
                100                 105                 110

Ser Ala Ala Val Thr Ser Met Ser Val Pro Thr Pro Ile Tyr Gln Thr
                115                 120                 125

Ser Ser Gly Gln Tyr Ile Ala Ile Ala Pro Asn Gly Ala Leu Gln Leu
                130                 135                 140

Ala Ser Pro Gly Thr Asp Gly Val Gln Gly Leu Gln Thr Leu Thr Met
145                 150                 155                 160

Thr Asn Ser Gly Ser Thr Gln Gln Gly Thr Thr Ile Leu Gln Tyr Ala
                165                 170                 175

Gln Thr Ser Asp Gly Gln Gln Ile Leu Val Pro Ser Asn Gln Val Val
                180                 185                 190

Val Gln Thr Ala Ser Gly Asp Met Gln Thr Tyr Gln Ile Arg Thr Thr
                195                 200                 205

Pro Ser Ala Thr Ser Leu Pro Gln Thr Val Val Met Thr Ser Pro Val
210                 215                 220

Thr Leu Thr Ser Gln Thr Thr Lys Thr Asp Asp Pro Gln Leu Lys Arg
225                 230                 235                 240

Glu Ile Arg Leu Met Lys Asn Arg Glu Ala Ala Arg Glu Cys Arg Arg
                245                 250                 255

Lys Lys Lys Glu Tyr Val Lys Cys Leu Glu Asn Arg Val Ala Val Leu
                260                 265                 270

Glu Asn Gln Asn Lys Thr Leu Ile Glu Glu Leu Lys Thr Leu Lys Asp
                275                 280                 285

Leu Tyr Ser Asn Lys Ser Val
290                 295

(2) INFORMATION FOR SEQ ID NO:108:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (xi) SEQUENCE DESCRIPTION: SEQ ID NO:108:

GGACGCGGTG GAATGGGCAG CGCTGGA                                        27

(2) INFORMATION FOR SEQ ID NO:109:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ix) FEATURE:
```

```
            (A) NAME/KEY: CDS
            (B) LOCATION: 1..21

(xi) SEQUENCE DESCRIPTION: SEQ ID NO:109:

AAG CCT GGT GGA CCC ATG GAT                                        21
Lys Pro Gly Gly Pro Met Asp
 1               5

(2) INFORMATION FOR SEQ ID NO:110:

(i) SEQUENCE CHARACTERISTICS:
            (A) LENGTH: 7 amino acids
            (B) TYPE: amino acid
            (D) TOPOLOGY: linear (ii) MOLECULE TYPE: protein (xi) SEQUENCE DESCRIPTION: SEQ ID NO:110:

Lys Pro Gly Gly Pro Met Asp
 1               5

(2) INFORMATION FOR SEQ ID NO:111:

(i) SEQUENCE CHARACTERISTICS:
            (A) LENGTH: 30 base pairs
            (B) TYPE: nucleic acid
            (C) STRANDEDNESS: double
            (D) TOPOLOGY: linear (ix) FEATURE:
            (A) NAME/KEY: CDS
            (B) LOCATION: 1..30

(xi) SEQUENCE DESCRIPTION: SEQ ID NO:111:

GGA CGC GGT GGA ATG GGA AAA ATT TTG AAA                            30
Gly Arg Gly Gly Met Gly Lys Ile Leu Lys
 1               5                  10

(2) INFORMATION FOR SEQ ID NO:112:

(i) SEQUENCE CHARACTERISTICS:
            (A) LENGTH: 10 amino acids
            (B) TYPE: amino acid
            (D) TOPOLOGY: linear (ii) MOLECULE TYPE: protein (xi) SEQUENCE DESCRIPTION: SEQ ID NO:112:

Gly Arg Gly Gly Met Gly Lys Ile Leu Lys
 1               5                  10

(2) INFORMATION FOR SEQ ID NO:113:

(i) SEQUENCE CHARACTERISTICS:
            (A) LENGTH: 30 base pairs
            (B) TYPE: nucleic acid
            (C) STRANDEDNESS: double
            (D) TOPOLOGY: linear (ix) FEATURE:
            (A) NAME/KEY: CDS
            (B) LOCATION: 1..30

(xi) SEQUENCE DESCRIPTION: SEQ ID NO:113:

CGG CGC CCA TCT TAC AGA AAA ATT TTG AAA                            30
Arg Arg Pro Ser Tyr Arg Lys Ile Leu Lys
 1               5                  10

(2) INFORMATION FOR SEQ ID NO:114:
```

(i) SEQUENCE CHARACTERISTICS:
    (A) LENGTH: 10 amino acids
    (B) TYPE: amino acid
    (D) TOPOLOGY: linear (ii) MOLECULE TYPE: protein (xi) SEQUENCE DESCRIPTION: SEQ ID NO:114:

Arg Arg Pro Ser Tyr Arg Lys Ile Leu Lys
 1               5                  10

(2) INFORMATION FOR SEQ ID NO:115:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..27

(xi) SEQUENCE DESCRIPTION: SEQ ID NO:115:

CGG CGC CCA TCT TAC AGG ACC CAT GGA TGA                          30
Arg Arg Pro Ser Tyr Arg Thr His Gly
 1               5

(2) INFORMATION FOR SEQ ID NO:116:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO:116:

Arg Arg Pro Ser Tyr Arg Thr His Gly
 1               5

(2) INFORMATION FOR SEQ ID NO:117:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:117:

AGAAGGGTAC TTGTACATGG                                            20

(2) INFORMATION FOR SEQ ID NO:118:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (xi) SEQUENCE DESCRIPTION: SEQ ID NO:118:

ATCGTTGAGA CTCGTACCAG CAGAGTCACG AGAGAGACTA CACGGTACTG GTTTTTTTTT   60

TTTTT                                                              65

(2) INFORMATION FOR SEQ ID NO:119:

(i) SEQUENCE CHARACTERISTICS:
        (A) LENGTH: 20 base pairs
        (B) TYPE: nucleic acid (C) STRANDEDNESS: single
            (D) TOPOLOGY: linear (xi) SEQUENCE DESCRIPTION: SEQ ID NO:119:

CCCACTAGTT ACCCACCCCA                                                    20

(2) INFORMATION FOR SEQ ID NO:120:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:120:

CGTTGAGACT CGTACCAGCA G                                                  21

(2) INFORMATION FOR SEQ ID NO:121:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO:121:

TCCTACAGCC AAGCTCCAAG TC                                                 22

(2) INFORMATION FOR SEQ ID NO:122:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO:122:

TACCAGCAGA GTCACGAGAG AG                                                 22

(2) INFORMATION FOR SEQ ID NO:123:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO:123:

AACAGAGCAG CAGCTACGGG CA                                                 22

(2) INFORMATION FOR SEQ ID NO:124:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:124:

CGAGAGAGAC TACACGGTAC TGG                                                23

(2) INFORMATION FOR SEQ ID NO:125:

(i) SEQUENCE CHARACTERISTICS:
            (A) LENGTH: 24 base pairs
            (B) TYPE: nucleic acid
            (C) STRANDEDNESS: single
            (D) TOPOLOGY: linear

```
    (xi) SEQUENCE DESCRIPTION: SEQ ID NO:125:

AAAACTCCAC TAGGAAATCC ATTT                                                   24

(2) INFORMATION FOR SEQ ID NO:126:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:126:

CTGGGAGGGG GGAGTGGAAG                                                        20

(2) INFORMATION FOR SEQ ID NO:127:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:127:

GGGCCGATCT CTGCGCTCCT                                                        20

(2) INFORMATION FOR SEQ ID NO:128:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (xi) SEQUENCE DESCRIPTION: SEQ ID NO:128:

CCA GAT CTT GAT CTA GGT TCA CTG CTG GCC TAT                                  33
Pro Asp Leu Asp Leu Gly Ser Leu Leu Ala Tyr
 1               5

(2) INFORMATION FOR SEQ ID NO:129:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO:129:

Pro Asp Leu Asp Leu Gly Ser Leu Leu Ala Tyr
 1               5
```